US010238627B2

(12) United States Patent
Corson et al.

(10) Patent No.: US 10,238,627 B2
(45) Date of Patent: *Mar. 26, 2019

(54) COMPOUNDS FOR TREATMENT OF ANGIOGENESIS-MEDIATED DISEASES

(71) Applicants:Indiana University Research and Technology Corporation, Indianapolis, IN (US); Gachon University of Industry-Academic Cooperation Foundation, Seongnam-si, Gyeonggi-do (KR)

(72) Inventors: Timothy W. Corson, Fishers, IN (US); Halesha D. Basavarajappa, Indianapolis, IN (US); Seung-Yong Seo, Seongnam-si (KR); Bit Lee, Seongnam-si (KR); Xiang Fei, Seongnam-si (KR)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/889,409

(22) Filed: Feb. 6, 2018

(65) Prior Publication Data

US 2018/0177758 A1 Jun. 28, 2018

Related U.S. Application Data

(63) Continuation-in-part of application No. 14/888,117, filed as application No. PCT/US2014/036965 on May 6, 2014.

(60) Provisional application No. 61/819,895, filed on May 6, 2013.

(51) Int. Cl.
*A61K 31/352* (2006.01)
*A61K 9/00* (2006.01)
*A61P 35/00* (2006.01)

(52) U.S. Cl.
CPC .......... *A61K 31/352* (2013.01); *A61K 9/0019* (2013.01); *A61K 9/0048* (2013.01); *A61P 35/00* (2018.01)

(58) Field of Classification Search
CPC .......... A61K 31/352; A61K 9/00; A61P 35/00
See application file for complete search history.

(56) References Cited

U.S. PATENT DOCUMENTS

| | | | | |
|---|---|---|---|---|
| 2007/0161644 | A1* | 7/2007 | Stockwell | C07D 239/91 514/252.17 |
| 2016/0060241 | A1* | 3/2016 | Corson | C07D 311/22 514/456 |

FOREIGN PATENT DOCUMENTS

| | | |
|---|---|---|
| WO | 2008156654 A2 | 12/2008 |
| WO | 2013016441 A1 | 1/2013 |

OTHER PUBLICATIONS

Kim et al., 2008, caplus an 2008:527611.*
Desideri, N. et al., Homoisoflavonoids: Natural Scaffolds with Potent and Selective Monamine Oxidase-B Inhibition Properties; J. Med. Chem., 2011, vol. 54, pp. 2155-2164.
Farkas, L., et al., J. (1971) Synthesis of Homoisoflavanones—II Constituents of Eucomis autumn alis and E. Punctata. Tetrahedron, 27, 5049-5054.
Krishnamutry, H.G. et al., Synthesis of Eucomin, 4'-Demethyleucomin & 5,7-Di-O-methyleucomol; Indian Journal of Chemistry, 1974, vol. 12, pp. 554-556.
Mulvagh et al., Journal of Chemical Research, Synopses, 1979, No. 4, 1-page.
Sathyanarayana, S. et al., Chemistry of Homoisoflavonoids: Synthesis of Polyhydroxy 3-Benzylchromes & 3-Benzylchroman-4-ones without Protection & Deprotection of Hydroxyl Groups & a Convenient Preparation of Benzylidenechroman-4-ones; Indian Journal of Chemistry, 1988, vol. 27B, pp. 899-901.
Adinolfi et al., Absolute Configuratio of Homoisoflavanones from *Muscari* Species, Tetrahedron, 1988, vol. 44, No. 15, pp. 4981-4988.
Wood et al., Imperial Chemical Industries Ltd., UK, S. African, 49 pgs, 1981.
Basavaiah et al., A new protocol for the syntheses of (E)-3-benzylidenechroman-4-ones: a simple synthesis of the methyl ether of bonducellin; Chem. Commun. 1998, vol. 16, pp. 1639-1640.
Bezabih et al., HPLC Analysis and NMR Identification of Homoisoflavonoids and Stilbenoids from the Inter-bulb Surfaces of Scilla nervosa, NPC Natural Product Communications; 2009, pp. 1-4.
Bhaskar et al., Syntheses of Pashanone & Its Isomers & Their Derivatives, Indian Journal of Chemistry, 1974, vol. 12, No. 6, pp. 557-560.
Birch et al., Caplus, Synthesis of rotenone and its derivatives. X. 6,7-Dimethoxychroman-4-one; 1-page.
Borgonovo et al., Taste-Active Compounds in a Traditional Italian Food: Lampascioni, Chemistry & Biodiversity, 2008, vol. 5, pp. 1184-1194.
CAS Registry No. 1390966-54-7; SciFinder, pp. 1-3.
Du Toit et al., Anti-inflammatory activity and QSAR studies of compounds isolated from *Hyacinthaceae* species and Tachiadenus longiflorus Griseb (Gentianaceeae); Natural Products Research Group, School of Chemistry, University of KwaZulu-Natal, Durban, 4041, S. Africa; 2005, 2-pgs.
El-Rayyes et al., Heterocycles. Part XVII, Synthesis of New Substituted 2, 3, 3a, 4, 5, 6-Hexahydrobenzo[6,7]cyclohepta[1,2-clpyrazoles and related compounds; J. Heterocyclic Chem. 1989, vol. 26, pp. 209-214.

(Continued)

*Primary Examiner* — Sun Jae Yoo
(74) *Attorney, Agent, or Firm* — Stinson Leonard Street LLP

(57) ABSTRACT

Synthetic cremastranone and cremastranone analogs are disclosed. Additionally, methods for synthesizing cremastranone and cremastranone analogs are disclosed. Methods of treating ocular neovascularization disorders and treating angiogenesis-mediated disease are also disclosed.

11 Claims, 28 Drawing Sheets

(56) References Cited

OTHER PUBLICATIONS

Famuyiwa et al., Homoisoflavonoids from the inter-bulb surfaces of *Scilla nervosa* subsp.*rigidifolia*; Phytochemistry Letters, 2012, vol. 5, No. 3, pp. 591-595.
Farkas et al., The Synthesis of Eucomin and (±)-Eucomol1, Tetrahedron, 1970, vol. 26, No. 11, pp. 2787-2790.
Kim et al., Expedient Synthesis of 3-Benzoylflavones by PCC Oxidation of 3-Benzylideneflavanones; Bull. Korean Chem. Soc. 2008, vol. 29, No. 10, pp. 2039-2042.
Makrandi et al., CAPLUS, Indian Journal of Chemistry, Section B; Organic Chemistry Including Medicinal Chemistry, 1980-1981, pp. 739-743.
Pinkey et al., Phase Transfer Catalysed Hydroxymethylation of 2'-Hydroxydihydrochalcones: A New Synthesis of Homoisoflavonones, Indian Journal of Chemistry, 1986, vol. 25B, No. 4, pp. 365-367.
Pfeiffer et al., CAPLUS, 1918, 1 page.
PubChem Compound; Compound Summary for: CID 77052; Retrieved from the internet: <URL: http://pubchem.ncbi.nlm.nih.gov/search/search.cgi> Mar. 28, 2005. See the chemical structure of CID 77052.
PubChem Compound; Compound Summary for: CID 638276; Retrieved from the internet: <URL: http://pubchem.ncbi.nlm.nih.gov/search/search.cgi> Mar. 26, 2005. See the chemical structure of CID 638276.
PubChem Compound; Compound Summary for: CID 1241457; Retrieved from the internet: <URL: http://pubchem.ncbi.nlm.nih.gov/search/search.cgi> Jul. 10, 2005. See the chemical structure of CID 1241457.
Sarda et al., Solvent-free NaOH-Al2O3 supported synthesis of 1,3-diaryl-2-propene-1ones; International Journal of ChemTech Research; 2009, vol. 1, No. 2, pp. 265-269.
Shaikh et al., Synthesis and NMR elucidation of homoisoflavanone analogues, Struct. Chem. 2011, vol. 22, pp. 161-166.
Shim et al., Anti-angiogenic activity of a homoisoflavanone from Cremastra appendiculata; Planta Medica, vol. 70, No. 2, 2004, pp. 171-173.
Sidwell et al., The Homo-Isoflavones II; Isolation and Structure of 4'-O-Methyl-Punctatin, Autumnalin, and 3,9-Dihydro-Autumnalin, Tetrahedron Letters, 1970, pp. 475-478.
Whitelaw et al., Synthesis and Sensory Evaluation of Ring-Substituted Dihydrochalcone Sweeteners, J. of Agric. and Food Chem., 1991, vol. 39, No. 1, pp. 44-51.

\* cited by examiner

FIG. 19A  FIG. 19B  FIG. 19C  FIG. 19D
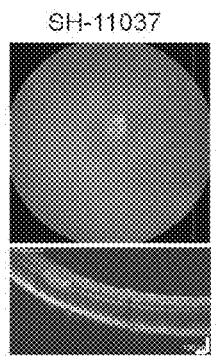 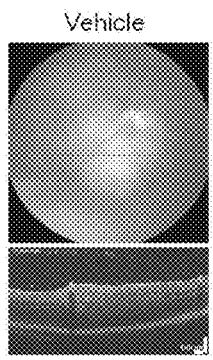 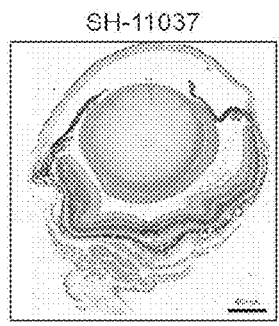 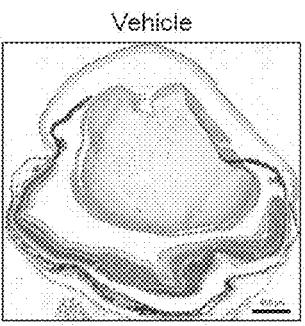
FIG. 19E
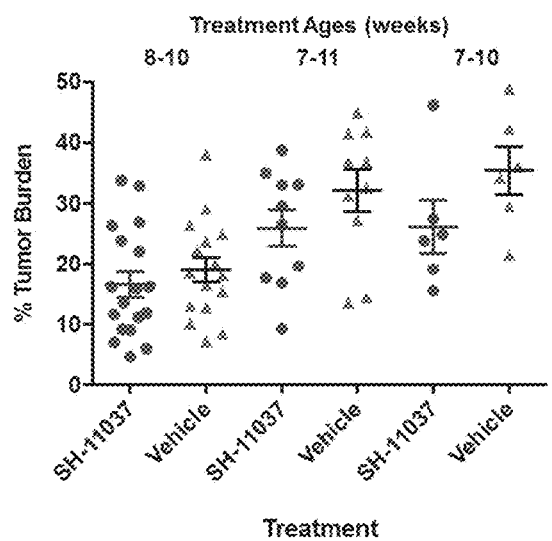
- Treatment effect $P<0.05$, two-way ANOVA
  - 8-10 weeks: 13% reduction
  - 7-11 weeks: 19% reduction
  - 7-10 weeks: 26% reduction

COMPOUNDS FOR TREATMENT OF ANGIOGENESIS-MEDIATED DISEASES

CROSS-REFERENCE TO RELATED APPLICATIONS

This application is a continuation-in-part of U.S. application Ser. No. 14/888,117 (U.S. Pub. No. 2016/0060241), filed on Oct. 30, 2015, which claims priority to International Publication Number WO 2014/182695, filed on May 6, 2014, which claims priority to U.S. Provisional Patent Application No. 61/819,895 filed on May 6, 2013, the disclosures of which are hereby expressly incorporated by reference in their entireties.

BACKGROUND

The present disclosure relates generally to compounds for the treatment of angiogenesis-mediated diseases. More particularly, the present disclosure relates to cremastranone analogs and methods for synthesizing cremastranone analogs.

Angiogenesis does not occur in the body, except during development and wound repair processes. However, during numerous pathological conditions, angiogenesis occurs, notably in many cancers.

Retinoblastoma, an angiogenesis-dependent tumor, is the most common ocular cancer in children without effective targeted treatment. Particularly, cytotoxic systemic or local chemotherapy is a mainstay of retinoblastoma therapy, but is associated with significant side effects, such as retinal toxicity, vascular events, ototoxicity, neutropenia and others.

Based on the foregoing, it would be highly advantageous to produce small molecule anti-angiogenic therapies to complement existing approaches for treatment of cancers, and in particular, retinoblastoma. It would be additionally beneficial, if these molecules performed as well, or better, than traditional therapies, and if these molecules could treat cancers without side effects.

BRIEF DESCRIPTION

The present disclosure is generally related to synthetic compounds, and in particular, organically synthesized cremastranone and cremastranone analogs. Additionally, the present disclosure relates to methods for organically synthesizing the compounds. The structure of homoisoflavanones includes a chromanone with a substituted benzyl group at the C-3 position in the C ring. Among them, cremastranone 1, as extracted from *C. appendiculata*, is a unique homoisoflavanone comprising dihydroxy at the C-5 and C-7 positions and methoxy at the C-6 position, respectively, with a 3'-hydroxy-4'-methoxybenzyl group at the C-3 position of chromanone. The present disclosure has now surprisingly found methods for organically synthesizing compounds such as cremastranone 1 and other cremastranone analogs having similar (e.g., SH-11037 (6c)), and in some embodiments, even greater, potency as compared to cremastranone 1 in its extracted natural form. As used herein, "synthetic" or "organically synthesized" or "chemically synthesized" or "organically synthesizing" or "chemically synthesizing" or "organic synthesis" or "chemical synthesis" are used to refer to preparing the compounds through a series of chemical reactions; this does not include extracting the compound, for example, cremastranone, from a natural source.

In one aspect, the present disclosure is directed to a synthetic compound comprising formula (I)

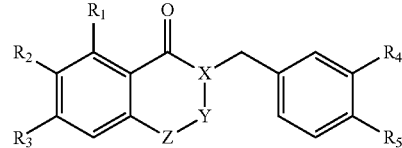

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen. In one particular aspect, the present disclosure is directed to the compound of formula (6c) (SH-11037):

In another aspect, the present disclosure is directed to a synthetic compound comprising formula (VI)

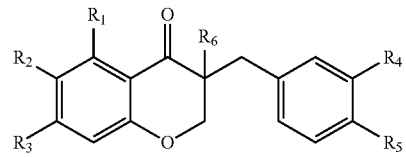

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl.

In another aspect, the present disclosure is directed to a method for synthesizing a compound of formula (I)

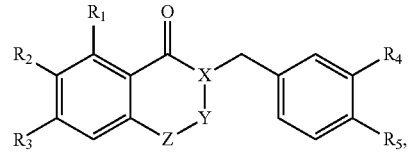

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen. The method comprises: condensing 6'hydroxy-2',3',4'-trimethoxy-acetophenone with a substituted or unsubstituted benzaldehyde to form a chalcone; reducing the chalcone under $H_2$ and Pd on activated charcoal to form a dihydrochalcone; hydroxymethylating and cyclizing the dihydrochalcone with formalin and NaOH to form a chromanone mixture; removing the hydroxymethyl group to form a monosubstituted chromanone comprising formula (IX)

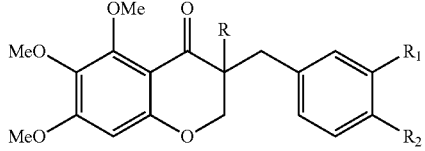

(IX)

wherein R is hydrogen or hydroxymethyl, and $R_1$ and $R_2$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and demethylating the chromanone of formula (IX).

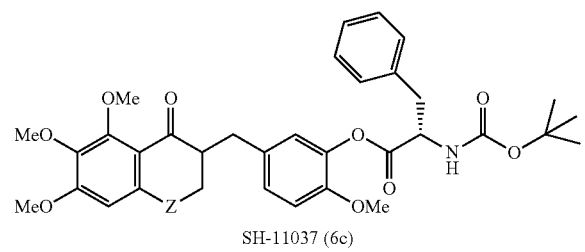

SH-11037 (6c)

prepared by the above-described method.

In yet another aspect, the present disclosure is directed to a method for synthesizing dihydrochalcone of formula (X)

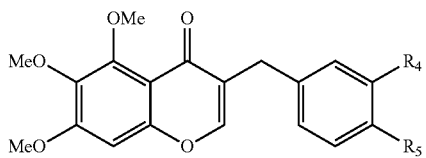

(X)

wherein $R_4$ and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl. The method comprises: condensing 6'-hydroxy-2',3',4'-trimethoxy-acetophenone with a substituted or unsubstituted benzaldehyde to form a chalcone; reducing the chalcone under $H_2$ and Pd on activated charcoal to form a dihydrochalcone; condensing the dihydrochalcone with N,N-dimethylformamide and a Lewis acid to form the chromone comprising formula (X); and demethylating the chromone of formula (X).

In yet another aspect, the present disclosure is directed to a method of treating retinoblastoma in a subject in need thereof. The method comprising administering a therapeutically effective amount of a synthetic compound comprising formula (I)

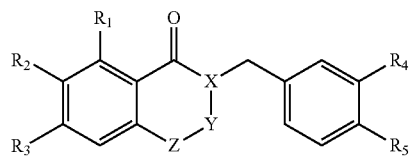

(I)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen, and a pharmaceutically acceptable carrier.

In yet another aspect, the present disclosure is directed to a method of treating neovascular eye disease in a subject in need thereof. The method comprising administering a therapeutically effective amount of a synthetic compound comprising formula (VI)

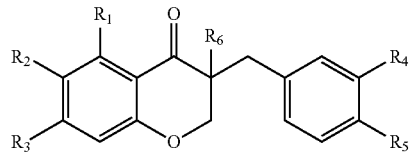

(VI)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl, and a pharmaceutically acceptable carrier.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 4:
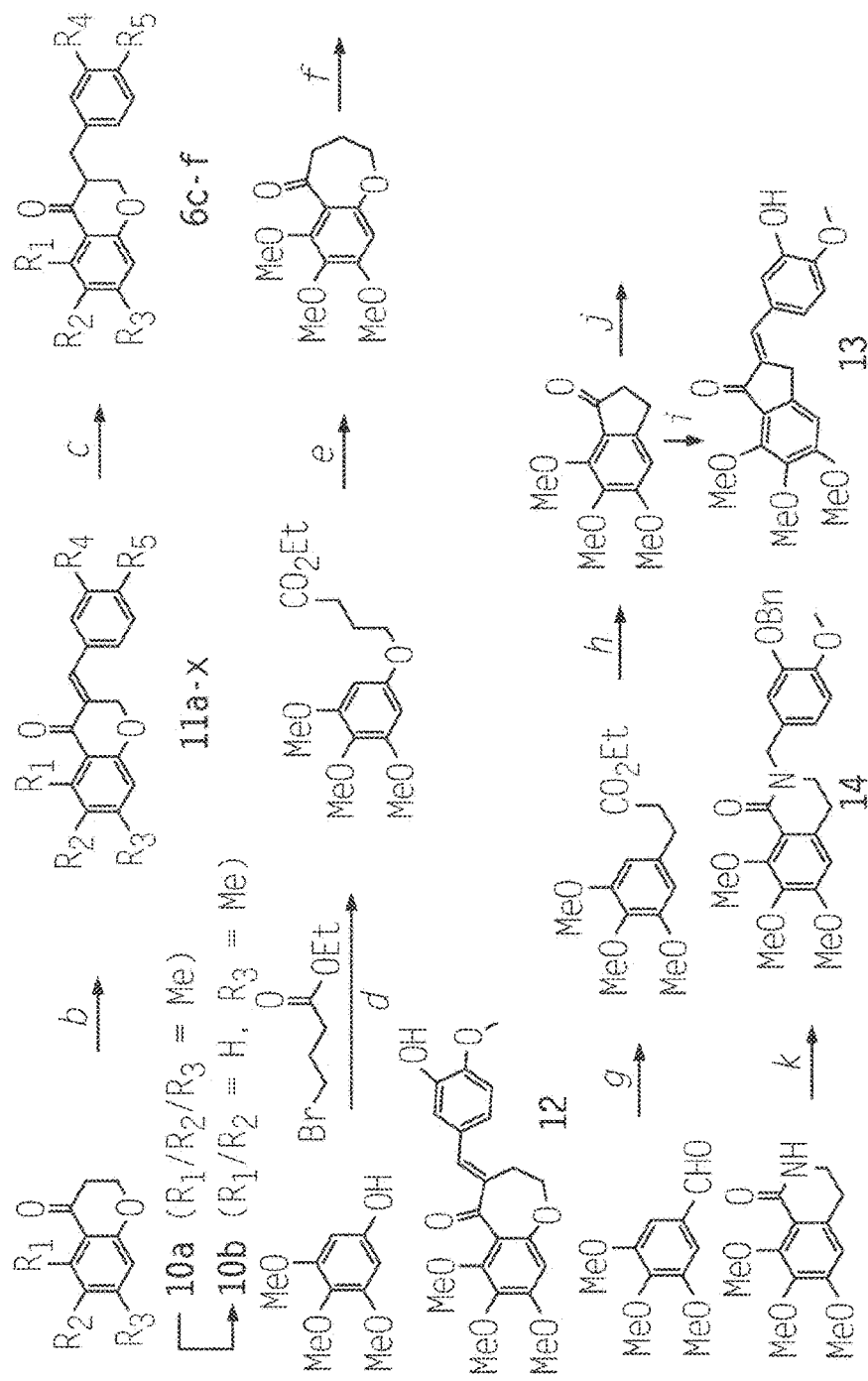

FIG. 4 is a schematic illustrating the synthesis of cremastranone analogs as discussed in Examples 5-7. Synthesis of cremastronone analogs. Reagents and conditions: a) TMSI, CHCl3; b) Arylaladehyde, PTSA, benzene, reflux; c) H$_2$, Pd/C, MeOH, rt; c) K$_2$CO$_3$, acetone, reflux; e) PPA; f) Isovanillin PTSA, benzene, reflux; g) Ph$_3$P=CHCO$_2$Et, toluene then H$_2$, Pd/C, MeOH, rt; h) PPA; i) Isovanillin, PTSA, benzene, reflux; f) NaN$_3$, CH$_3$SO$_3$H; k) Aryl bromide, NaH.

Figure 5:
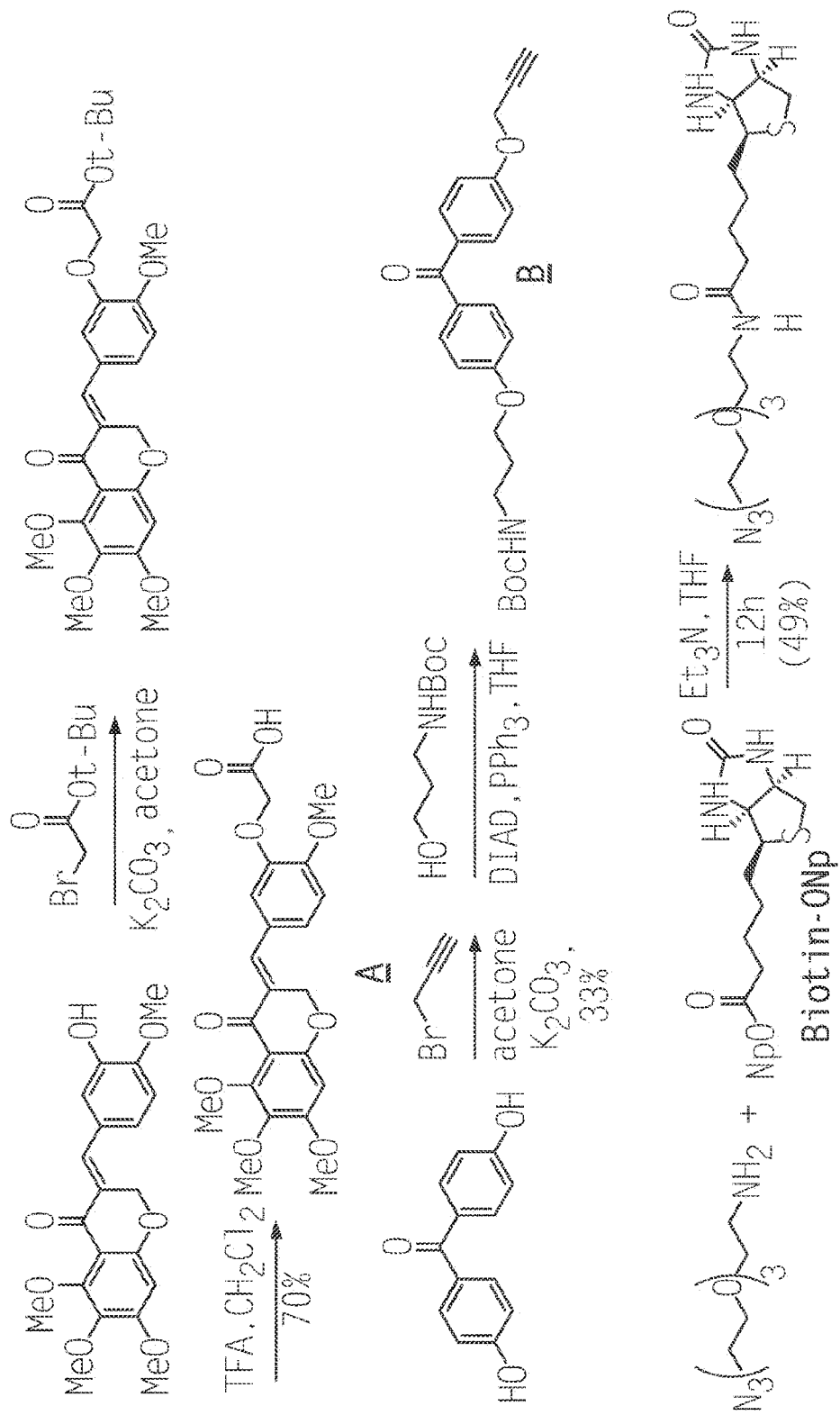
Figure 5:
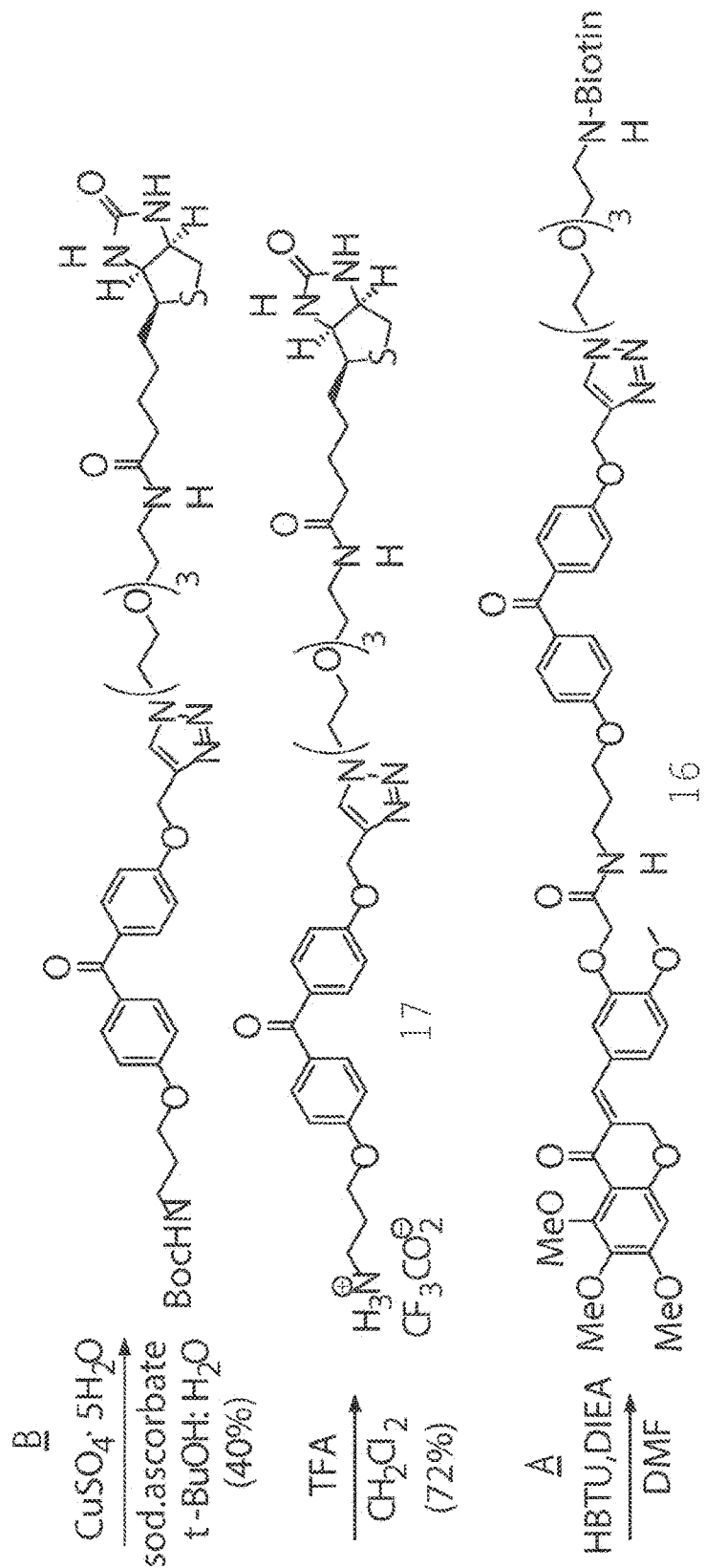
Figure 6A:
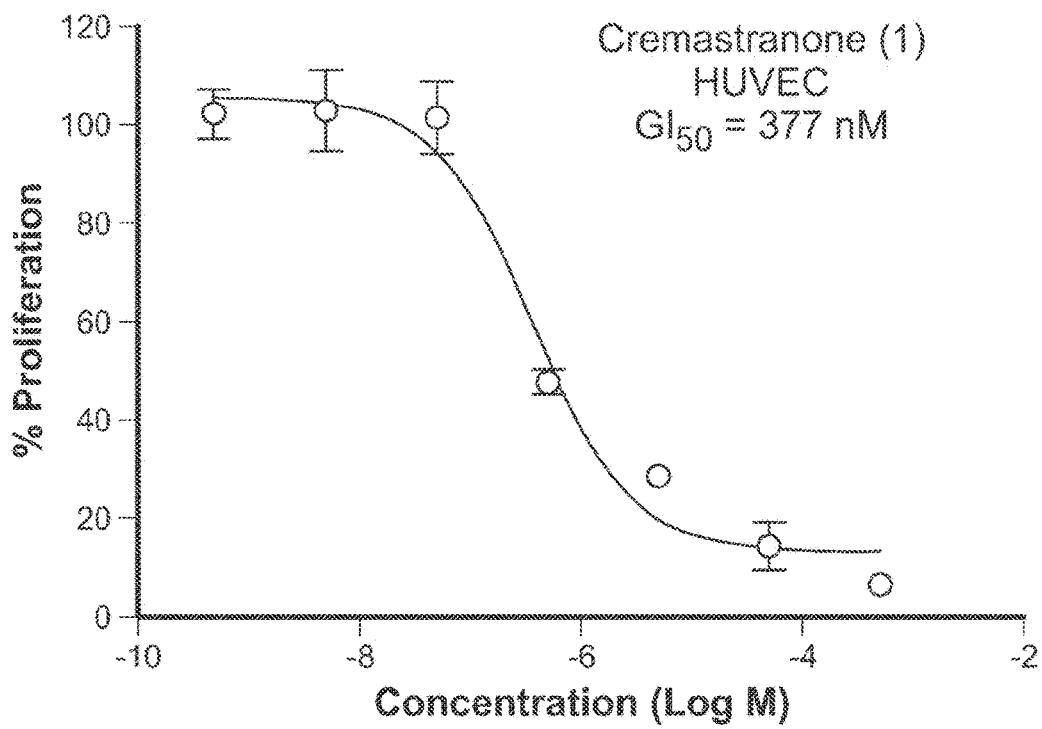
Figure 6B:
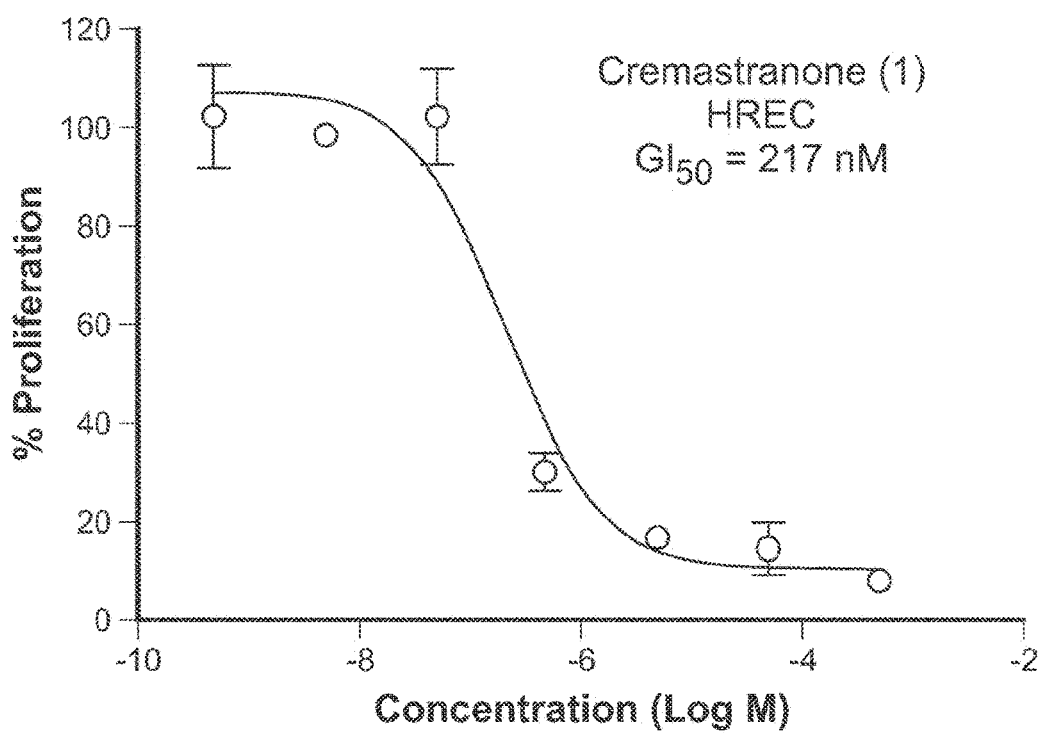
Figure 6C:
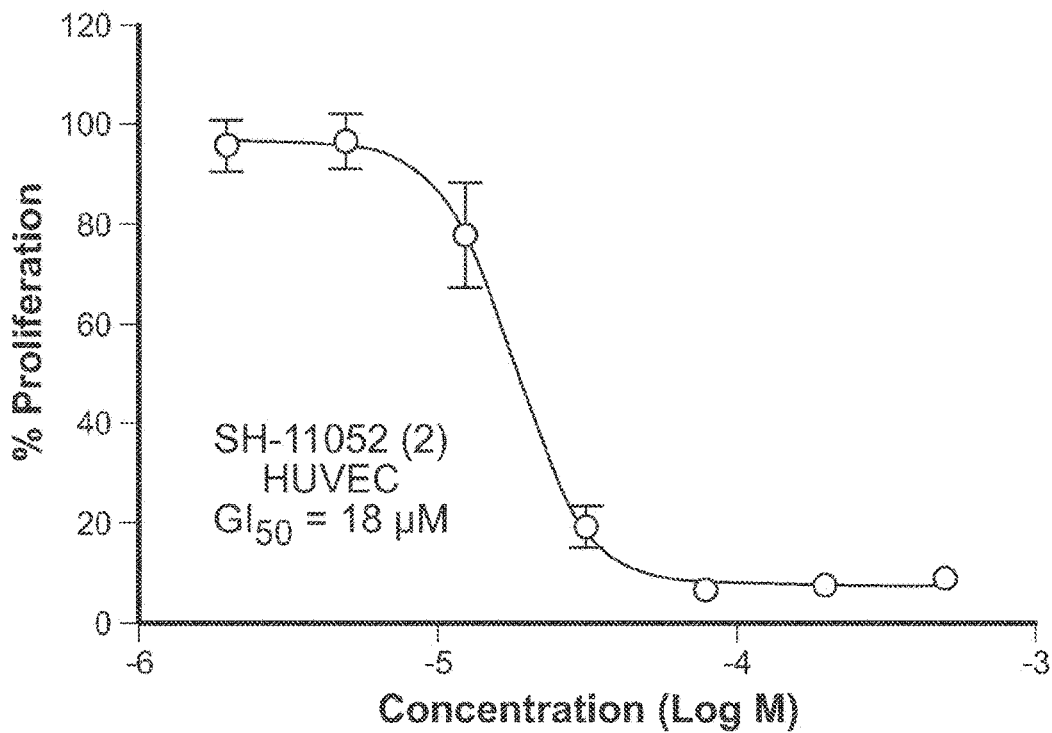
Figure 6D:
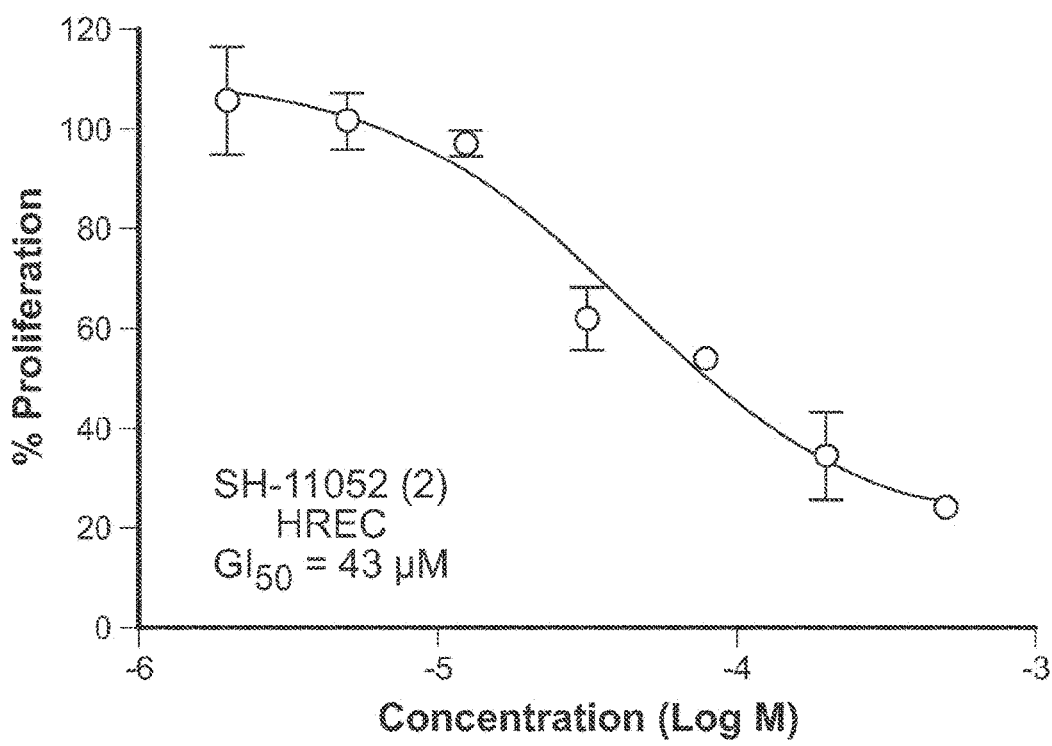
Figure 7A:
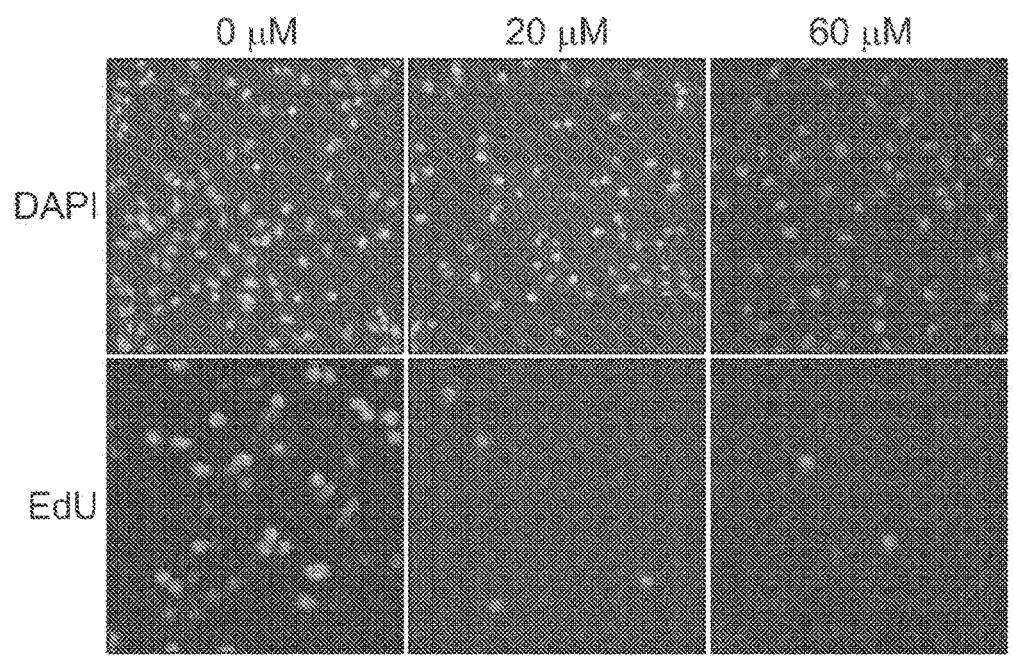
Figure 7B:
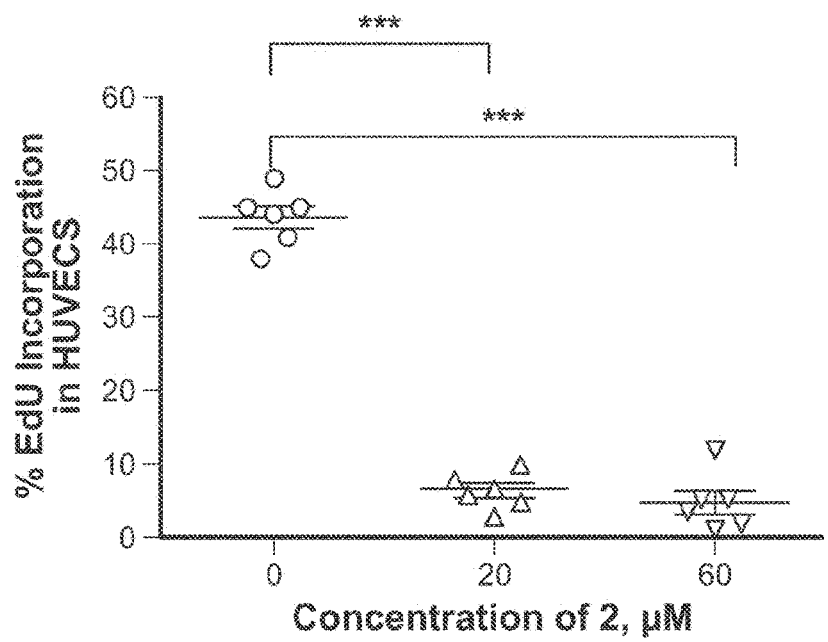
Figure 7C:
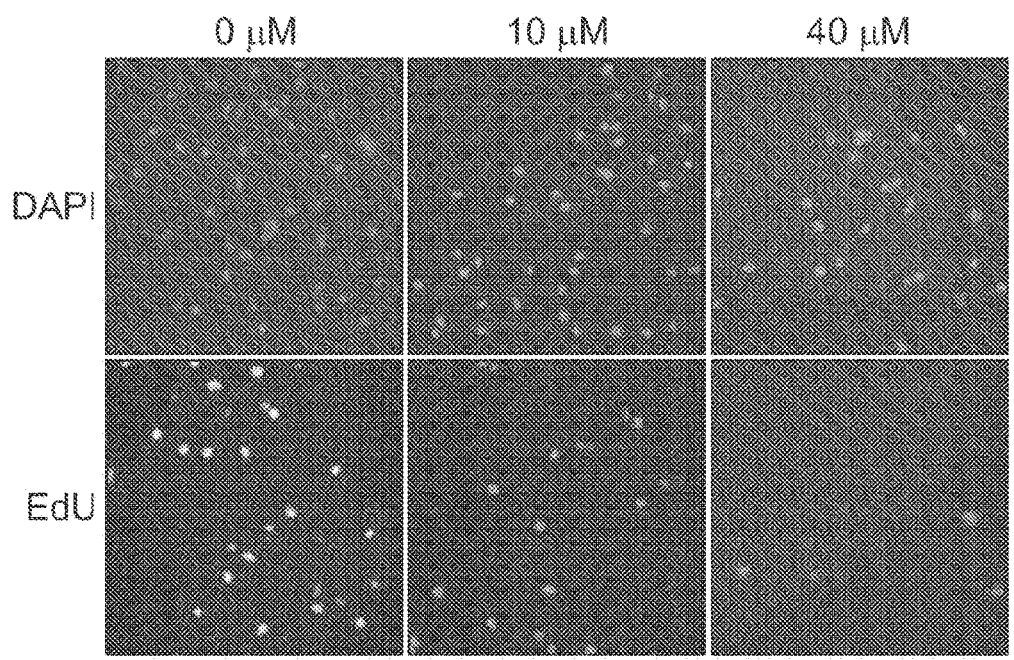
Figure 7D:
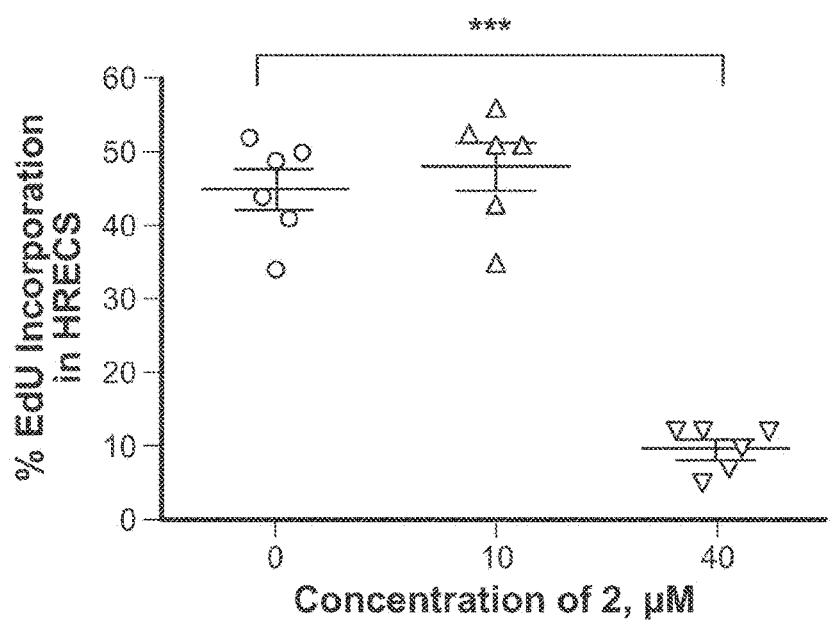

FIG. 5 is a schematic illustrating the synthesis of biotinylated compounds as discussed in Example 8.

FIGS. 6A-6D are graphs showing the effects of synthetic cremastranone (1) (FIG. 6A and FIG. 6B) and SH-11052 (2) (FIG. 6C and FIG. 6D) on the proliferation of HUVECs (FIG. 6A and FIG. 6C) and HRECs (FIG. 6B and FIG. 6D) as discussed in Example 9.

FIGS. 7A-7D show the effects of SH-11052 (2) on DNA synthesis in endothelial cells as discussed in Example 9. Specifically, after treatment with the indicated concentrations of SH-11052 (2) and an EdU pulse, the HUVECs (FIG. 7A, FIG. 7B) and HRECs (FIG. 7C, FIG. 7D) were stained with DAPI (for nucleus) and incorporated EdU (in proliferating cells) using a Click-iT kit. The cells were counted from six different fields of a coverslip and the percentage of proliferating HUVECs (FIG. 7B) and HRECs (FIG. 7D) was calculated from the ratio of EdU stained cells to DAPI stained cells in each section (dots in the graphs) using ImageJ analysis software. The lines indicated the mean+SEM and *** indicates $p<0.0001$ (ANOVA with Dunnett's post hoc test). Representative data from three independent experiments.

FIGS. 8A-8D show the effects of SH-11052 (2) on in vitro angiogenesis without causing apoptosis as discussed in Example 10. (FIG. 8A) Tube formulation on Matrigel by HRECs in the presence of the indicated concentrations of SH-11052 (2). (FIG. 8B) Polygons formed (open spaces) were counted. Mean+SEM of n=3 wells. *, $p<0.05$; *, $p<0.001$ compared to DMSO control (ANOVA with Dunnett's post hoc test). (FIG. 8C) HRECs were treated with indicated concentrations of SH-11052 (2) or staurosporine (SP) and stained with DAPI (for nucleus) and activated caspase-3 antibody. (FIG. 8D) Percentage of HRECs undergoing apoptosis was calculated by counting number of caspase (circled in FIG. 8C) stained cells compared to total cells using ImageJ software. Mean+SEM of cells from three different sections; representative data from two independent experiments. *$p<0.001$ compared to DMSO control (ANOVA with Dunnett's post hoc test).

FIGS. 9A-9E show the effects of SH-11052 (2) on TNF-α mediated NF-κB signaling as discussed in Example 11. (FIG. 9A) After treating HRECs with the indicatedconcentrations of SH-11052 (2), p65 was detected by immunofluorescence and nuclei stained with DAPI. Representative data from three independent experiments. (FIG. 9B) The protein levels of IκB-α were measured after TNF-α treatment in the presence of the indicated concentrations of SH-11052 (2) by imunoblot. (FIG. 9C & FIG. 9E) Densitometry was performed using Quantity One software and analyzed using GraphPad Prism. The lines indicate the mean+SEM of three biological replicates and * indicates $p<0.05$ compared to TNF-α treatment alone (ANOVA with Dunnett's post hoc test).

Figure 10A:
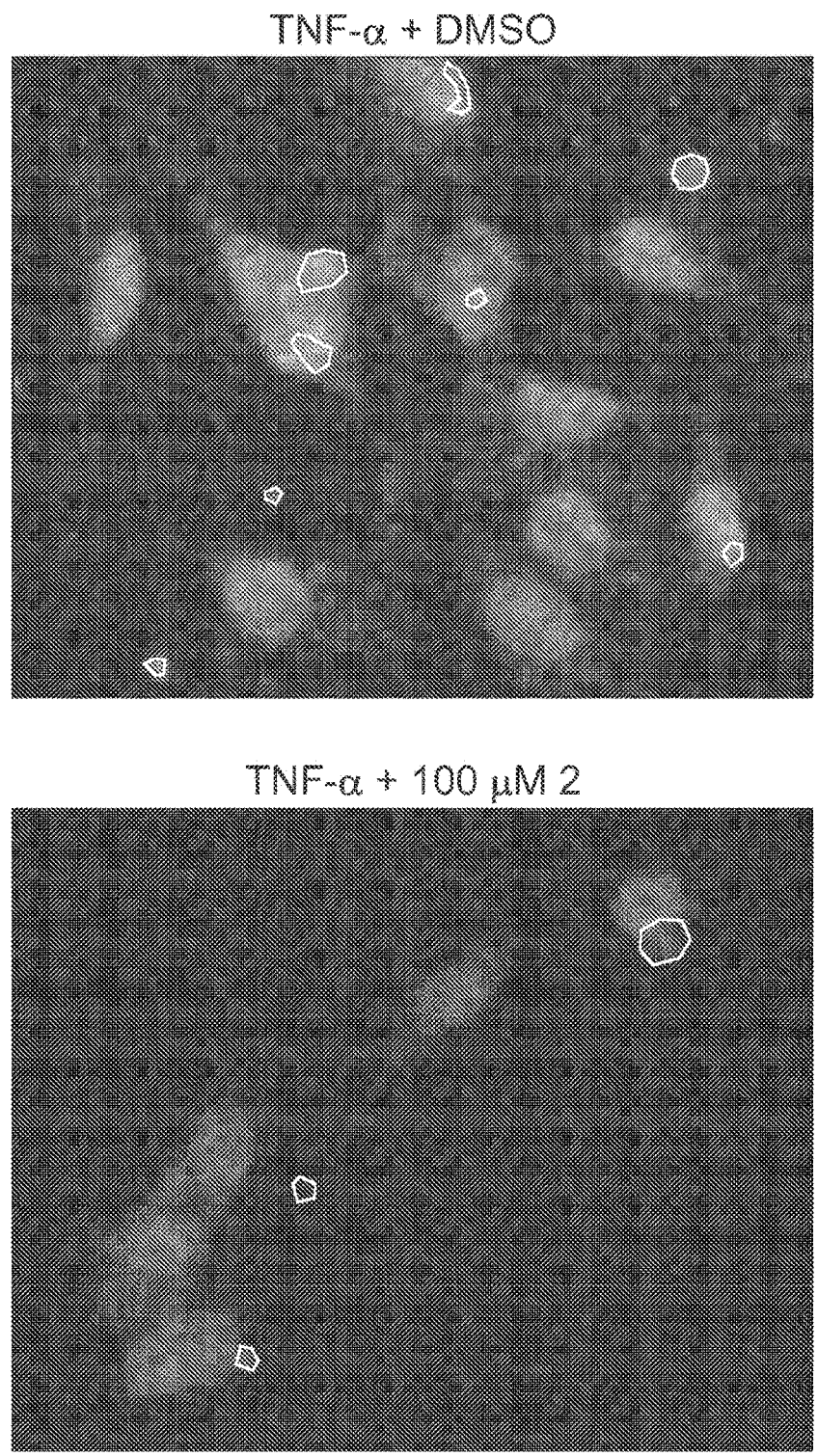
Figure 10B:
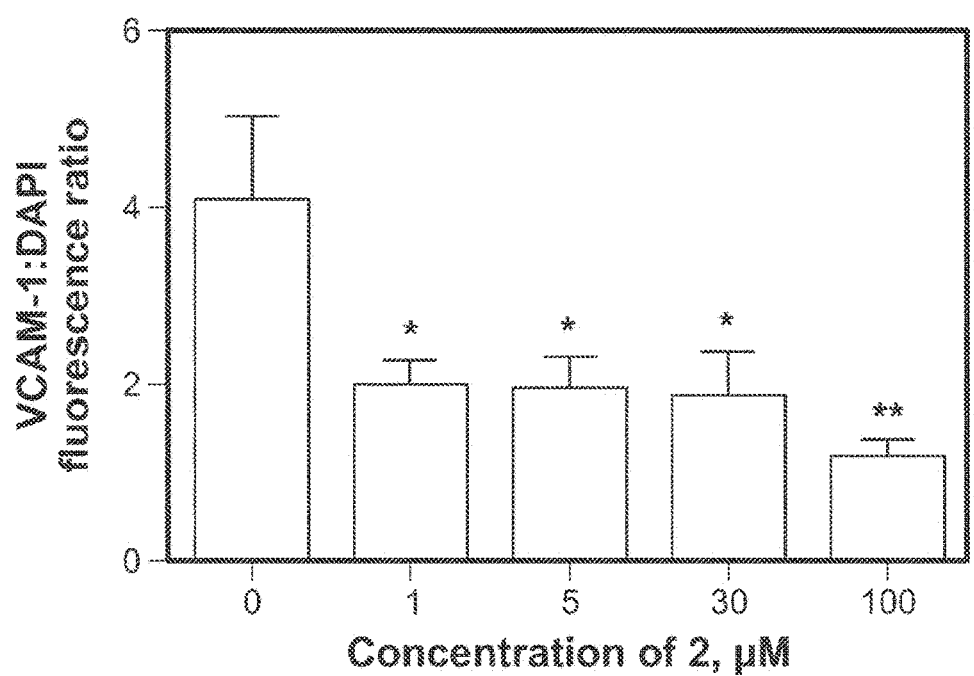
Figure 10C:
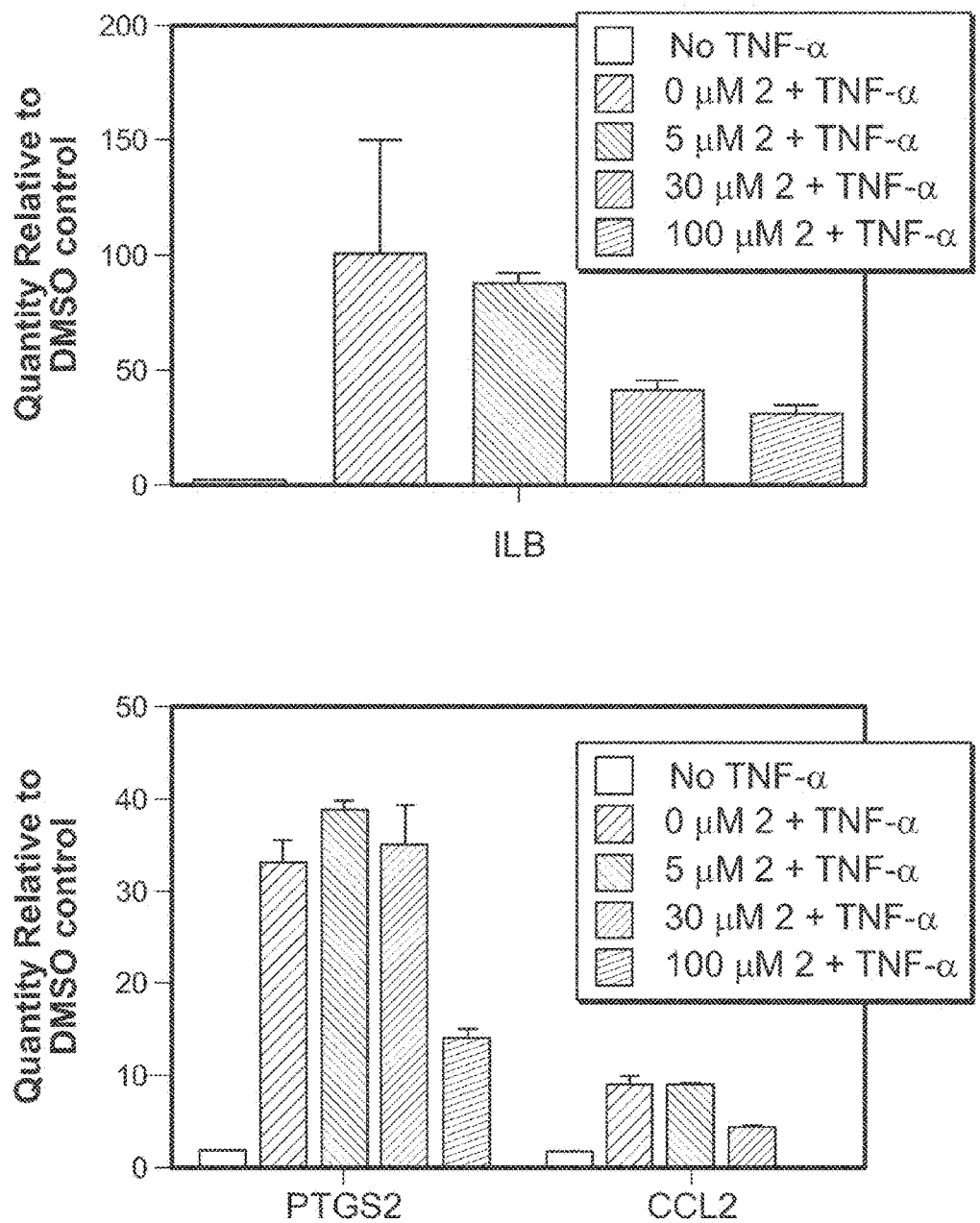
Figure 11A:
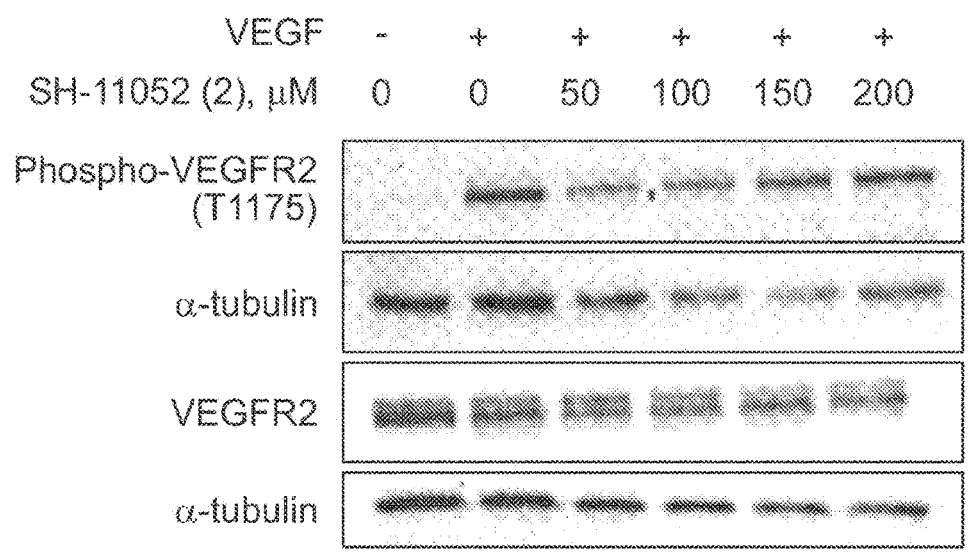
Figure 11B:
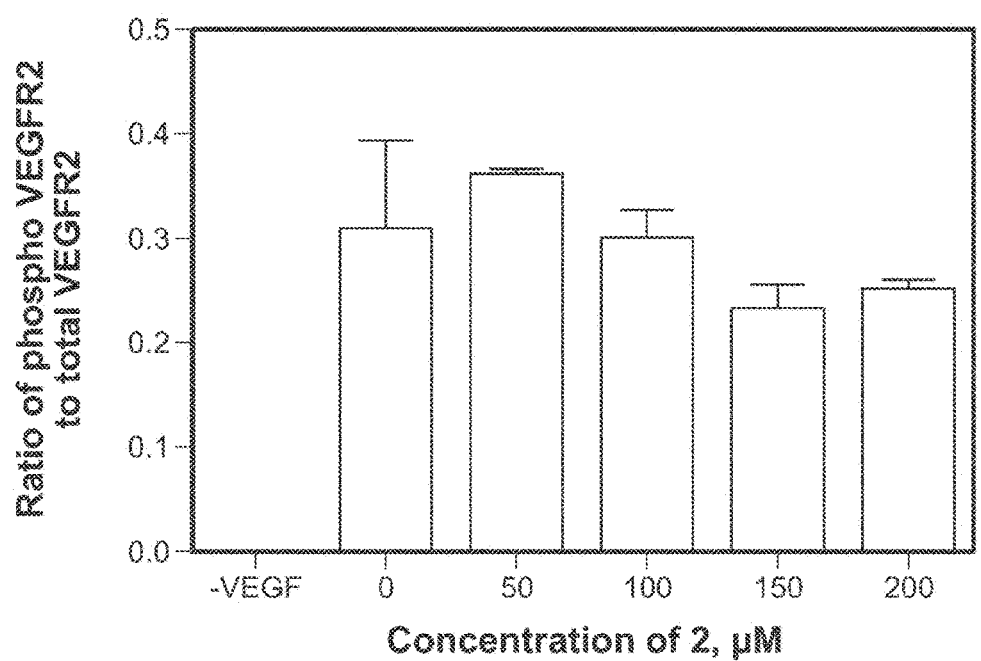
Figure 11C:
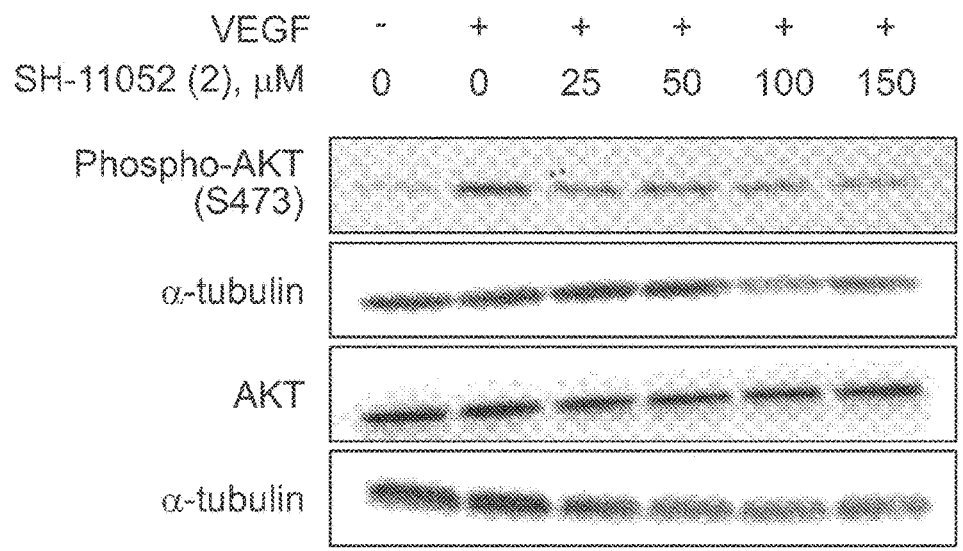
Figure 11D:
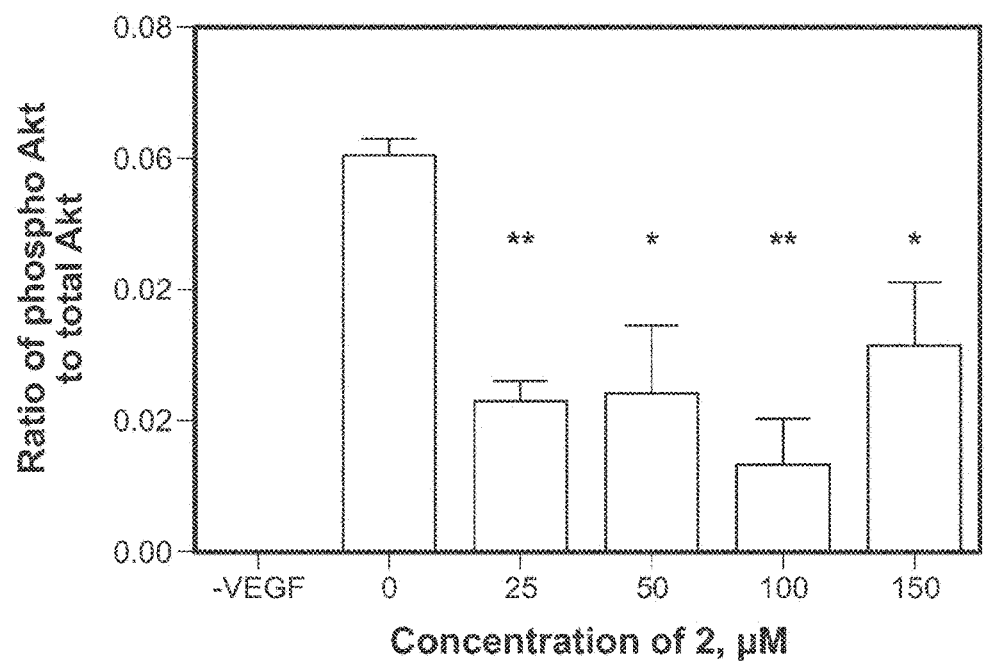

FIGS. 10A-10C show the effects of SH-11052 (2) on the expression of NF-κB target genes as discussed in Example 12. (FIG. 10A) Endothelial activation marker VCAM-1 (circled) was detected by immunofluorescence in HRECs exposed to TNF-α+SH-11052 (2). (FIG. 10B) MetaMorph fluorescence intensity analysis of VCAM-1 staining in the presence of TNF-α and the indicated concentrations of SH-11052 (2), mean+SEM of n=5 fields; *, $p<0.05$ , $p<0.01$ compared to DMSO control (ANOVA with Dunnett's post hoc test); representative data from two independent experiments. (FIG. 10C**) qRT-PCR using TaqMan probes showed that mRNA levels of NF-κB targets genes IL8 (interleukin-8) (top panel), CCL2 (MCP-1) and PTGS2 (COX2) (bottom panel), all induced by TNF-α, were decreased in the presence of SH-11052 (2) in a dose dependent manner. Note different y-axis scales. Mean+SEM of n=3 replicates shown; representative data from two independent experiments.

FIG. 11A-11D show the effects of SH-11052 (2) on VEGF mediated Akt signaling as discussed in Example 13. Phosphorylation of VEGFR2 (FIG. 11A) and Akt (FIG. 11C) was monitored in HRECs upon VEGF stimulation in the presence of varying concentrations of SH-11052 (2). (FIG. 11B & FIG. 11D) Densitometry was performed using Quantity One software and analyzed using GraphPad Prism. The lines indicated the mean+SEM of three biological replicates, * indicates $p<0.05$ and ** indicates $p<0.01$ compared to VEGF treatment alone (ANOVA with Dunnett's post hoc test).

Figure 12:
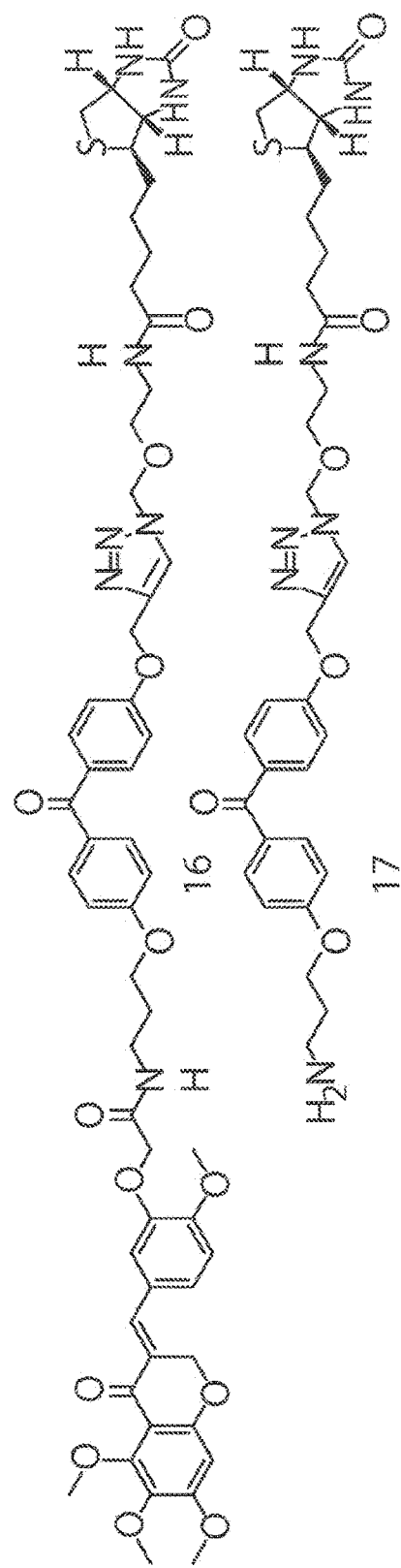

FIG. 12 depicts chemical structures for cremastranone affinity reagent 16 or control compound 17 as discussed in Example 14.

Figure 13:
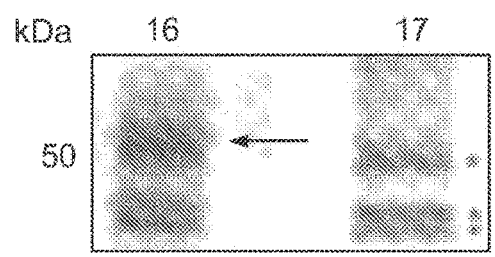

FIG. 13 is a silver-stained SDS-gel of a cremastranone affinity pulldown as discussed in Example 14.

Figure 14:
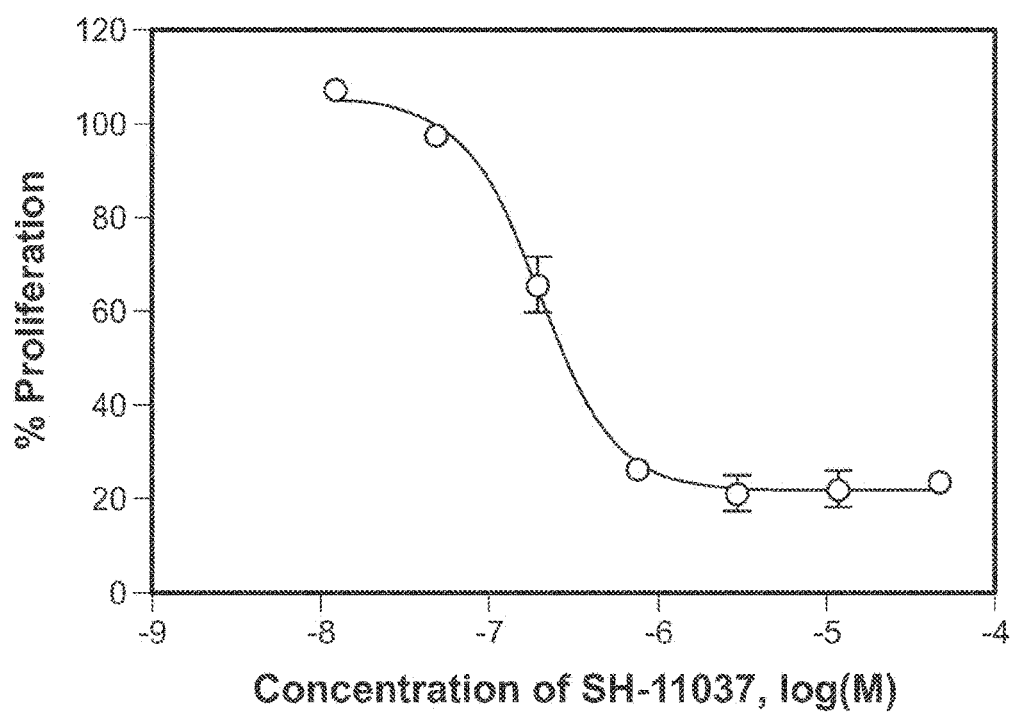

FIG. 14 is a graph showing inhibition of proliferation of HRECs by the cremastranone analog, SH-11037 (6c), as discussed in Example 15.

Figure 15A:
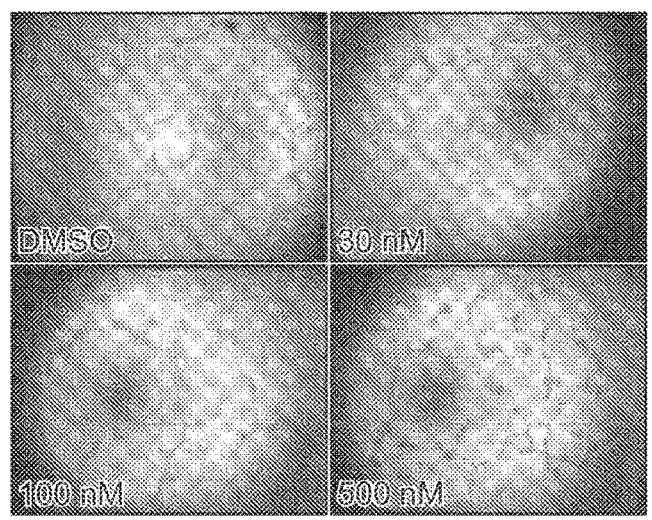

FIG. 15A is a montage of photomicrographs showing that tube formation of HRECs is inhibited by the cremastranone analog, SH-11037 (6c) (% polygons from n=3 wells indicated) as discussed in Example 15.

Figure 15B:
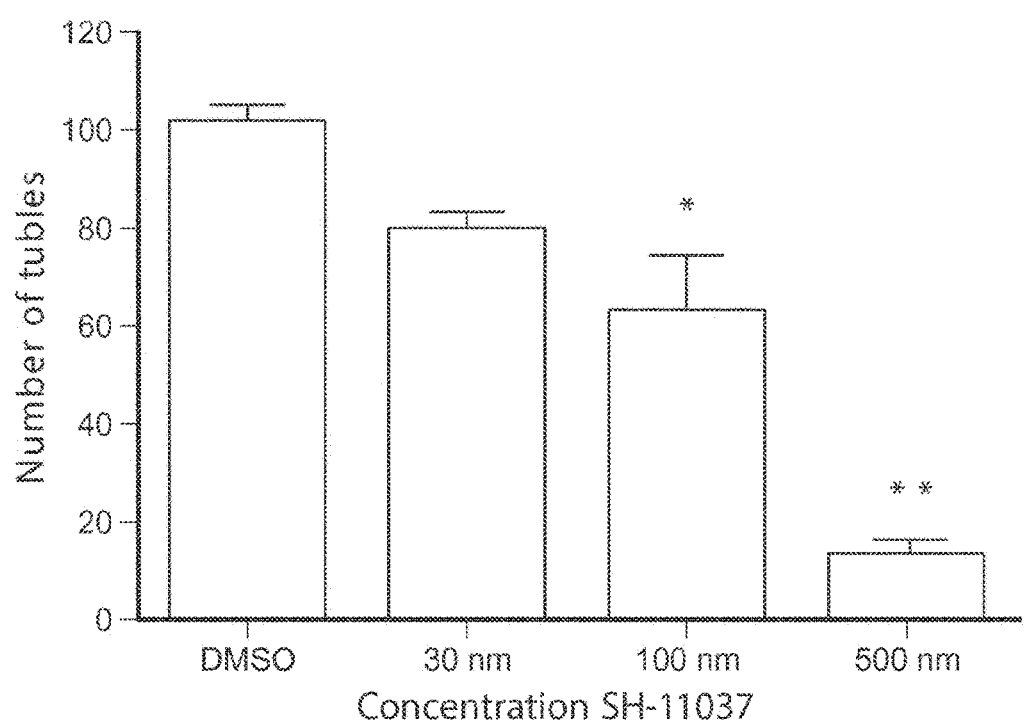

FIG. 15B is a graphic showing tube formation of HRECs is inhibited by the cremastranone analog, SH-11037 (6c) (% polygons from n=3 wells indicated) as discussed in Example 15.

Figure 16A:
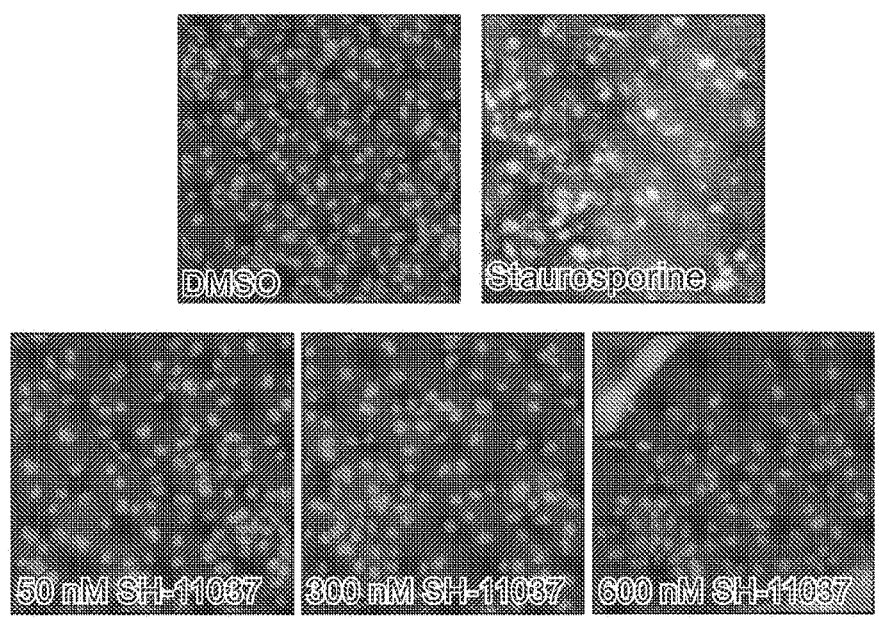
Figure 16B:
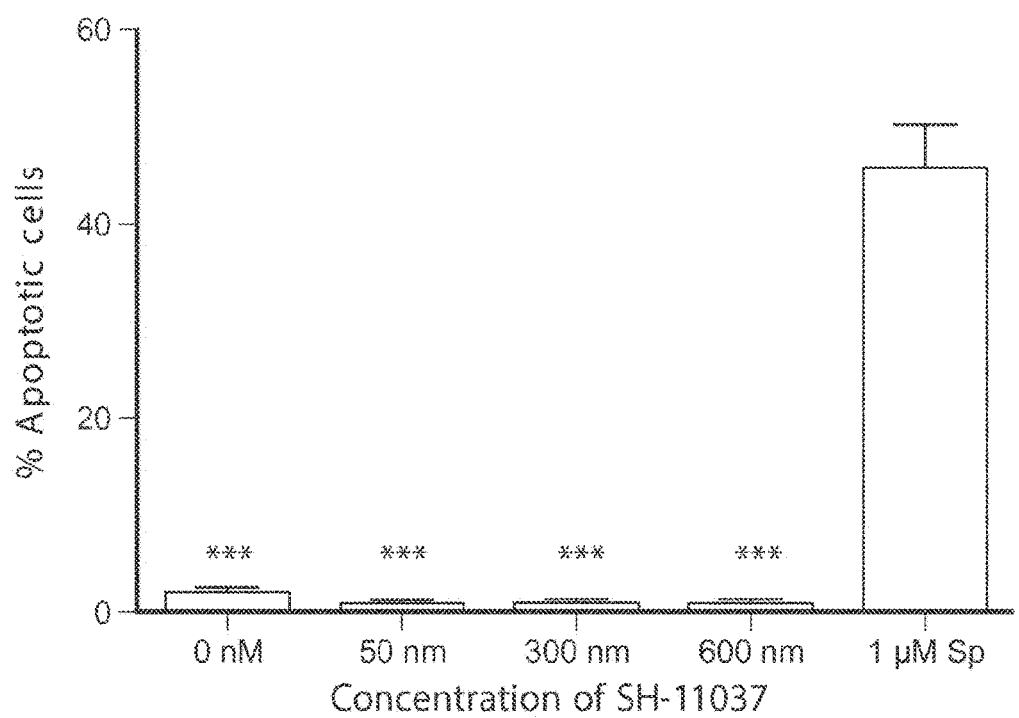

FIGS. 16A & 16B illustrate that the cremastranone analog, SH-11037 (6c), did not cause apoptosis of HREC as discussed in Example 15.

Figure 17:
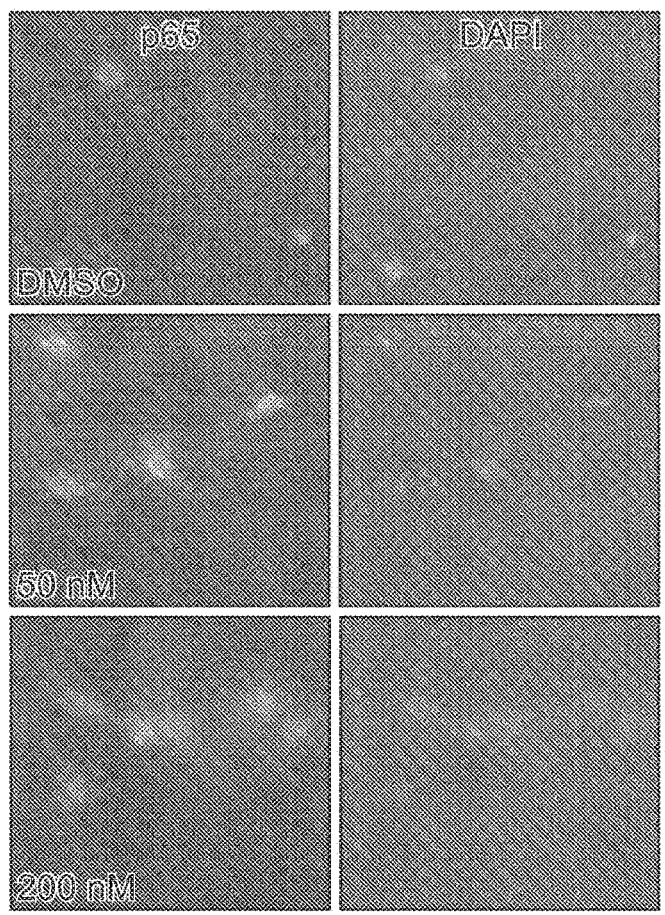

FIG. 17 are immunofluorescent micrographs showing that the cremastranone analog, SH-11037 (6c), did not inhibit NF-KB signaling as discussed in Example 15.

Figure 18A:
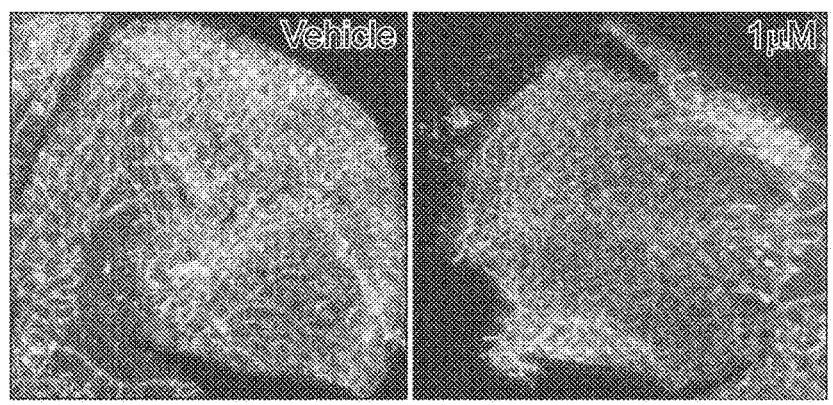

FIG. 18A are photomicrographs showing that the cremastranone analog, SH-11037 (6c), blocked neovascularization in vivo as discussed in Example 16.

Figure 18B:
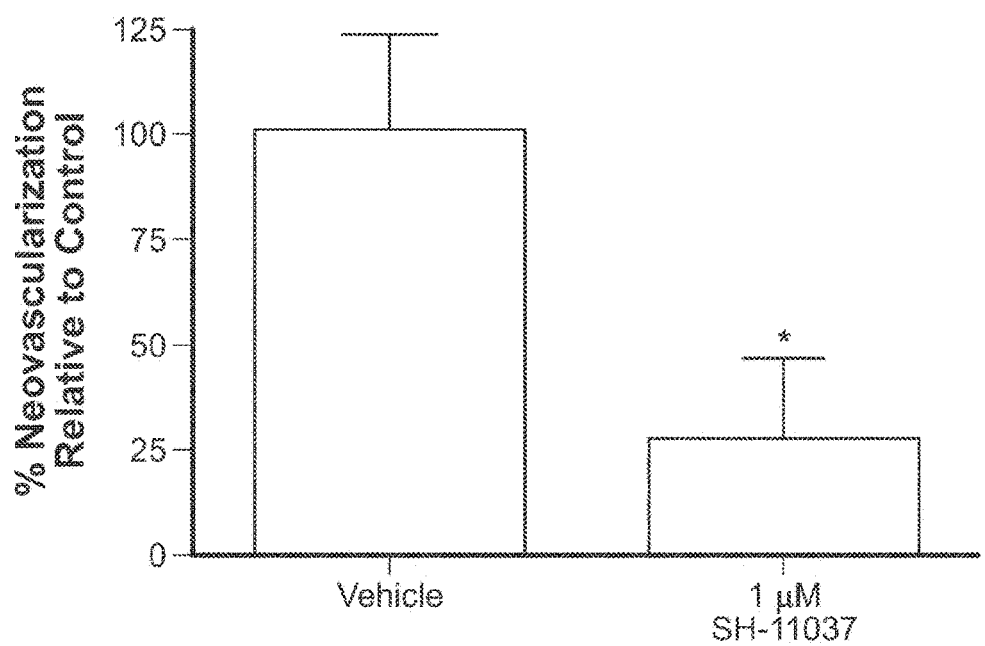

FIG. 18B is a graph showing that the cremastranone analog, SH-11037 (6c), decreased neovascular area as determined by SWIFT_NV analysis as discussed in Example 16.

FIGS. 19A-19E depict the effects of SH-11037 (6c) on the growth of retinoblastoma tumors. Tumors were evaluated using fundus photography, optical coherence tomography, and ex vivo quantification of tumor volume as described in Example 17.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, pentyl, hexyl and the like.

The term "amino" as used herein, alone or as part of another group, shall denote a primary, secondary or tertiary amine which may optionally be hydrocarbyl, substituted hydrocarbyl or heteroatom substituted.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aromatic" as used herein alone or as part of another group denote optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used interchangeably herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, amino, amido, nitro, cyano, ketals, acetals, esters and ethers.

The terms "angiogenesis-mediated disease", "angiogenesis-mediated disorder", or "angiogenesis-mediated condition" are used interchangeably herein to refer to a disease, disorder, or condition affecting angiogenesis, typically characterized by either poor vascularization or abnormal vasculature. "Treatment of angiogenesis-mediated diseases" refers to inhibiting or inducing the creation of new blood vessels in the body to combat, alleviate, or mediate the symptoms of the particular disease.

The terms "inflammation-mediated disease", "inflammation-mediated disorder", or "inflammation-mediated condition" are used interchangeably herein to refer to a disease, disorder, or condition result in abnormal inflammation of tissues and organs. Inflammation-mediated diseases include diseases, disorders, or conditions resulting from allergic reactions and myopathies. "Treatment of inflammation-mediated diseases" refers to inhibiting alleviating, or mediating the inflammatory symptoms of the particular disease.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Synthetic Cremastranone and Cremastranone Analogs

In accordance with the present disclosure, synthetic compounds, and in particular, organically synthesized racemates and enantiomers of cremastranone, as well as cremastranone analogs, and methods for organically synthesizing the compounds have been discovered. The chemically synthesized cremastranone, indicated herein as cremastranone 1, is a racemate and has an optical rotation of [α]D=0, as compared to cremastranone extracted from a natural source, which has an optical rotation of [α]D=−16. Cremastranone 1 and its isomer 2 have the formula

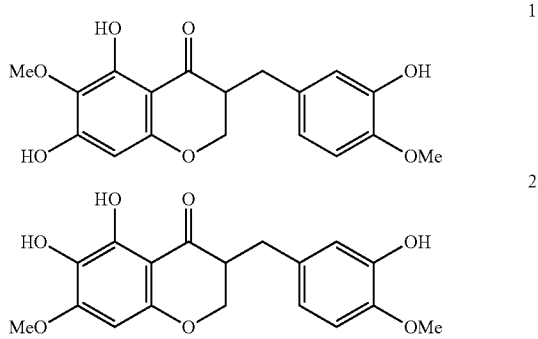

The synthetic compounds have been surprisingly found to show in vitro antiproliferative activity comparable to the natural extracted cremastranone, (see Table 1 below). As further discussed in the Examples below, organically synthesized SH-11052 (2) additionally blocked EdU incorporation during DNA synthesis in human umbilical vein endothelial cells (HUVECs) and human retinal microvascular endothelial cells (HRECs), caused similar gene expression changes as the natural extracted cremastranone (FIGS. 10A-10C), inhibited tube formation of HRECs (FIGS. 8A-8B), and blocked NF-κB signaling in HRECs (FIGS. 9A-9E).

Additionally, as discussed more fully in the Examples below, some of the cremastranone analogs of the present disclosure can increase potency, while promoting greater than 100-fold selectivity for HRECs over ocular tumor cell lines (Table 1).

Accordingly, in one aspect, the present disclosure is directed to a synthetic compound of formula (I)

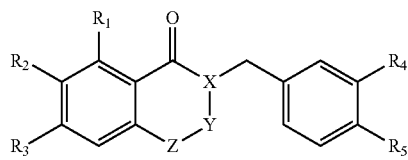

(I)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen, and racemates and enantiomers thereof.

Exemplary alkoxy groups include, for example, methoxy, ethoxy, and the like. Exemplary substitutions for use with the alkoxy groups include, for example, alkyl, aryl (e.g., phenyl), carboxy, and carbonyl.

Typically, R1, R2, R3 are independently selected from the group consisting of hydroxyl and alkoxy. In one particularly suitable embodiment, R1 and R2 are each hydroxyl and R3 is a methoxy. In another suitable embodiment, R1, R2, and R3 are independently methoxy. In yet another embodiment, R1 is a hydroxyl and R2 and R3 are each methoxy.

Typically, R4 and R5 are independently selected from the group consisting of hydroxyl, alkoxy and substituted alkoxy. Exemplary substitutions for alkoxy groups for use as R4 and R5 include alkyl (linear and branched) and aryl. In one particularly suitable embodiment, the substituted alkoxy is OBn. In another suitable embodiment, the substituted alkoxy is vinyl methoxy.

In particularly suitable embodiments, the chemically synthesized compounds include cremastranone 1 and its isomer 2

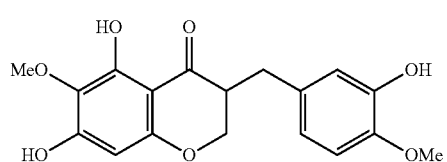

1

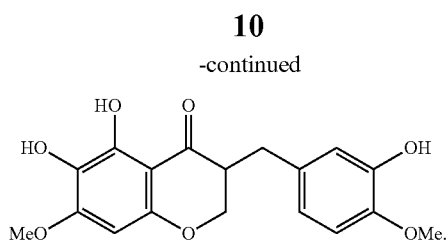

2

Suitably, the chemically synthesized cremastranone 1 and its isomer 2 have a purity of at least 60%, including at least 70%, including at least 80%, including at least 90% or greater.

In another particularly suitable embodiment, the organically synthesized compound is SH-11037 (6c)

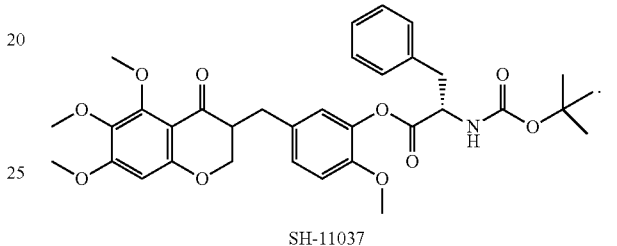

(6c)

SH-11037

In another aspect, the present disclosure is directed to a synthetic compound of formula (VI)

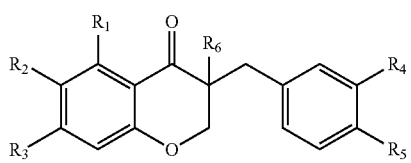

(VI)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl. In particularly suitable embodiments, $R_6$ is selected from the group consisting of hydrogen and a hydroxymethyl.

Methods for Synthesizing Cremastranone and Cremastranone Analogs

In another aspect, the present disclosure is directed to methods for chemically synthesizing the compounds, and in particular, cremastranone 1 and cremastranone analogs. The substantial challenge associated with total synthesis of cremastranone 1 was to uncover three phenolic groups on the C-5, C-7 (in A ring) and C-3' (in B ring) positions. For the formation of chromanone in cremastranone 1 and its isomer 2, dihydrochalcones were treated with formaldehyde or formamide dimethylacetal followed by reduction of chromone. And the regioselective demethylation among methoxy groups of the A and B rings was undertaken.

Accordingly, in one embodiment, the present disclosure is generally directed to methods for synthesizing a compound of formula (I)

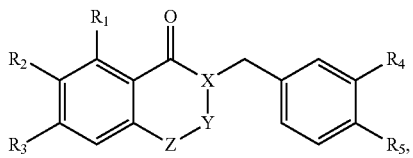

(I)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen. The method is generally initiated by condensing 4'-benzyloxy-6'-hydroxy-2',3'-dimethoxyacetophenone or 6'-hydroxy-2',3',4'-trimethoxy-acetophenone with a substituted or unsubstituted benzaldehyde to form a chalcone and reducing the chalcone under $H_2$ and Pd on activated charcoal to form a dihydrochalcone. To construct the chromanone from the dihydrochalcone, N,N-dimethylformamide dimethyl acetal was used in toluene, followed by the reduction of the resulting chromone. In the second method for the synthesis of the chromanone, the dihydrochalcone is then hydroxymethylated and cyclized with formalin and NaOH to form a chromanone mixture. Typically, the dihydrochalcone is hydroxymethylated and cyclized with approximately 3 equivalents of formalin and 8 equivalents of 50% NaOH. The C3 hydroxymethyl group is removed using approximately 2 equivalents of $K_2CO_3$ in EtOH to form a monosubstituted chromanone comprising formula (IX)

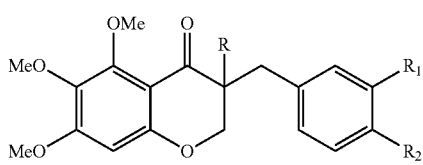

(IX)

wherein R is hydrogen or hydroxymethyl, and $R_1$ and $R_2$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and demethylating the chromanone of formula (IX) using approximately 6 to 8 equivalents of TMSI at 60° C. In one embodiment, the compound of formula (I) is SH-11037 (6c).

Figure 1:
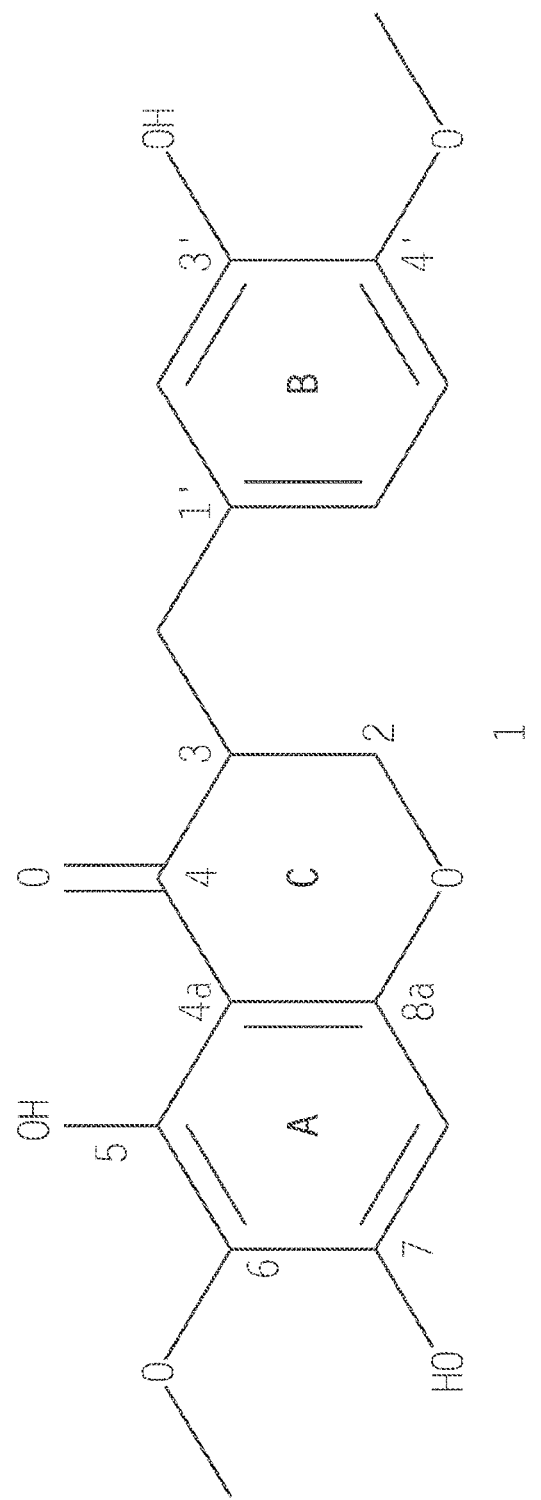
FIG. 1 depicts the chemical structure of natural cremastranone 1 as extracted from *C. appendiculata* and made synthetically using one synthesis method of the present disclosure.
Figure 2:
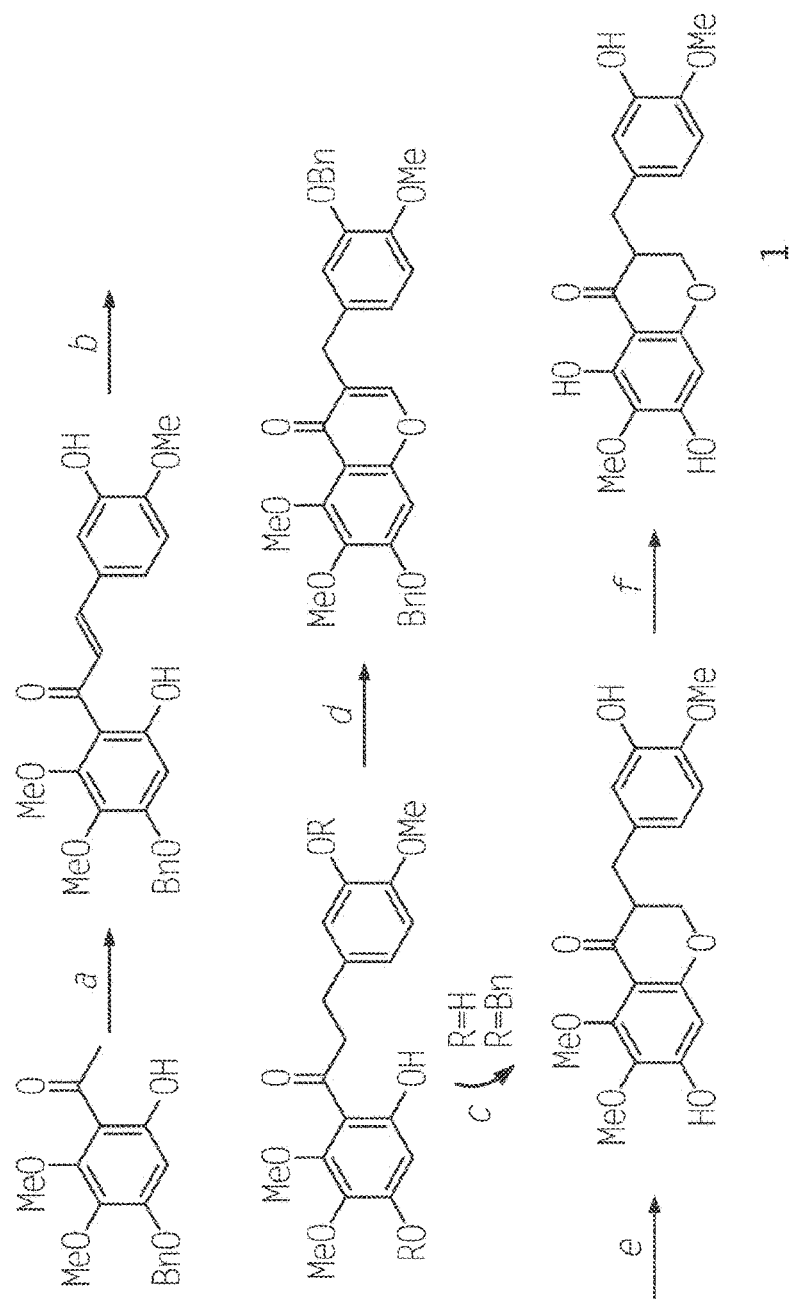
FIG. 2 is a schematic illustrating the synthesis of cremastranone 1 as discussed in Example 1. Synthesis of (±)-cremastranone (1). Reagents and conditions: a) isovanillin, KOH, EtOH, rt, 53%; b) $H_2$, Pd/C, MeOH, 98%; c) $K_2CO_3$, benzyl bromide, acetone, 35%; d) $(CH_3)_2$ $NCH(OCH_3)_2$, DMF, 80%; e) $H_2$, Pd/C, MeOH, 87%; f) TMSI, $CHCl_3$, 60β° C., 74%.
Figure 3:
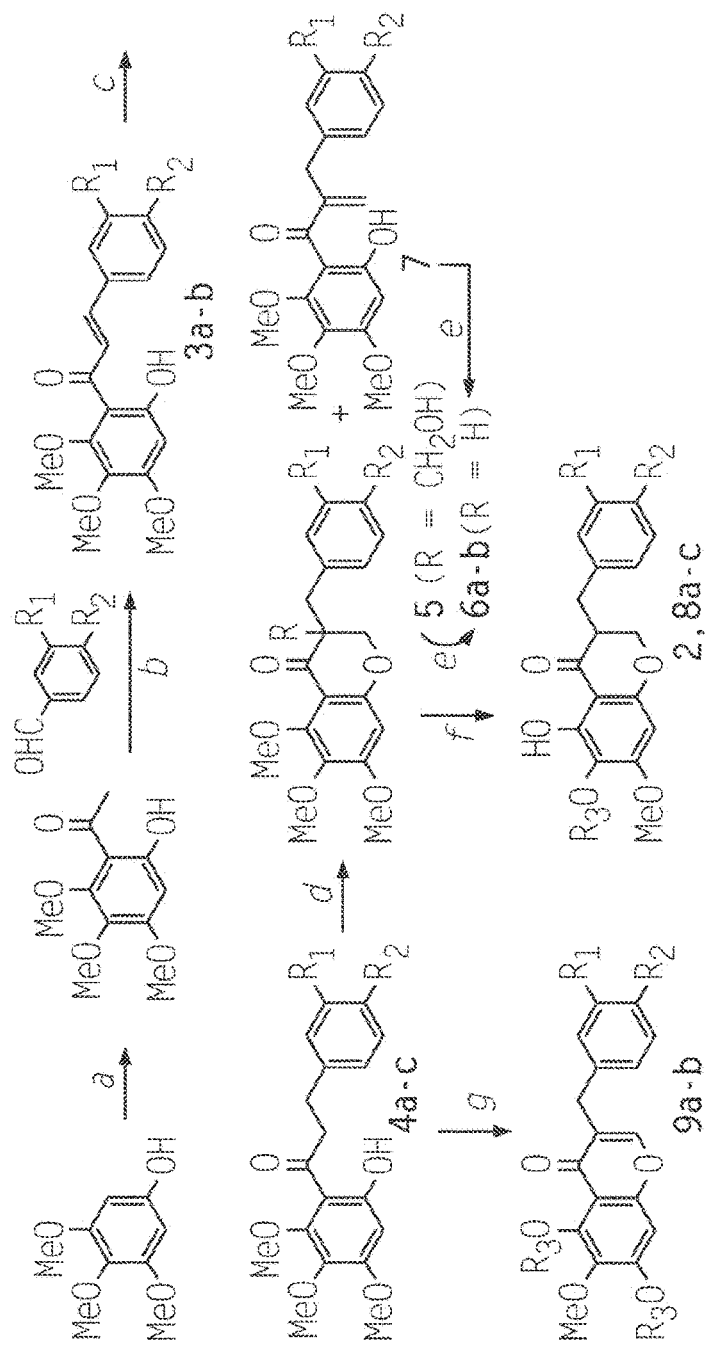
FIG. 3 is a schematic illustrating the synthesis of cremastranone isomer 2 and other analogs as discussed in Examples 2-4. Synthesis of cremastranone isomer (2) and analogs. Reagents and conditions: a) acetic anhydride, $BF_3$—$OEt_2$: b) arylaldehyde, KOH, MeOH, 0° C.; c) Pd/C, $HCO_2Na$, $HCO_2H$, 60° C.; d) formalin, NaOH, 60° C., 54% for 5, 10% for 6a, and 15% for 7; e) K$_2$CO$_3$, EtOH, 49% from 5, 72% from 7; f) TMSI, CHCl$_3$: g) PCl$_5$, BF$_3$—OEt$_2$, DMF or PCl$_5$, BF$_3$—OEt$_2$, DMF, then HBr, AcOH, reflux.

More particularly, the synthesis of cremastranone 1 and its isomer 2 is illustrated in FIGS. 2 and 3, respectively. The method for the synthesis of cremastranone 1 includes aldol condensation of 4'-benzyloxy-6'-hydroxy-2',3'-dimethoxyacetophenone with isovanillin, catalytic hydrogenation of the chalcone under H2 and Pd/C affording the dihydrochalcone which is treated with benzyl bromide to afford the dibenzyl ether. With the dibenzyl ether in hand, N,N-dimethylformamide dimethyl acetal is used generate to the corresponding chromone. After catalytic hydrogenation, the resulting chromanone is treated with 2 equivalents of TMSI to give cremasatranone (1).

In another embodiment, the present disclosure is directed to methods for synthesizing dihydrochalcone of formula (X)

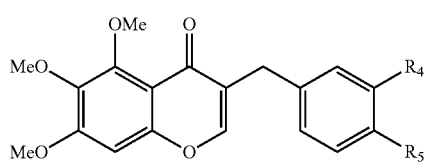

(X)

wherein $R_4$ and $R_5$ are independently selected from the group consisting of independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl. In this embodiment, the method includes: condensing 6'-hydroxy-2',3',4'-trimethoxy-acetophenone with a substituted or unsubstituted benzaldehyde to form a chalcone and reducing the chalcone under $H_2$ and Pd on activated charcoal to form a dihydrochalcone as described above, and further requires condensing the dihydrochalcone with excess N,N-dimethylformamide (DMF) and a Lewis acid to form the chromone of formula (X) and demethylating the chromone of formula (X). In one embodiment, the dihydrochalcone is condensed in a solution of excess DMF, 1.5 equivalents of $PCl_5$ and 3 equivalents of $BF_3$—$OEt_2$ at 20° C.

Pharmaceutical Compositions Including Cremastranone and Cremastranone Analogs and Uses Thereof The present disclosure is further directed to administering the synthetic compounds, and in particular, synthetic cremastranone 1, SH-11037 (6c) and other cremastranone analogs described herein, in a pharmaceutical composition for treating various diseases, disorders and conditions. In one embodiment, the synthetic compounds are administered for treating neovascular eye disease in a subject in need thereof. Generally, a therapeutically effective amount of a synthetic compound comprising formula (I)

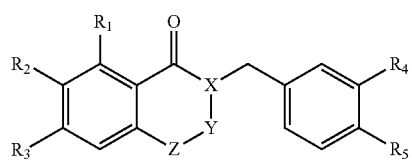

(I)

wherein $R_1$, $R_2$, $R_3$, $R_4$, and $R_5$ are independently selected from the group consisting of independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen and a pharmaceutically acceptable carrier are administered to a subject in need thereof. More particularly, the pharmaceutical compositions including the synthetic compounds and a pharmaceutically acceptable carrier can be administered to treat diseases such as retinopathy of prematurity, neovascular age-related macular degeneration, diabetic retinopathy, corneal graft rejection, neovascular glaucoma, rubeosis, and the like.

In yet another embodiment, the synthetic compounds are administered for treating angiogenesis and/or inflammation-mediated diseases in a subject in need thereof. Exemplary angiogenesis and/or inflammation-mediated diseases capable of being treated include non-ocular hemorrhage, myocardial infarction, stroke, cancer, atherosclerosis, ischaemic heart disease, coronary heart disease, peripheral arterial disease, wound healing disorders, and the like.

In yet another embodiment, the synthetic compounds are administered for treating retinoblastoma in a subject in need thereof.

The synthetic compounds are administered in a therapeutically effective amount to provide treatments of the above-described diseases and disorders. The phrase "therapeutically effective amount" of the compound of the disclosure means a sufficient amount of the compound to treat disorders, at a reasonable benefit/risk ratio applicable to any medical treatment. It can be understood, however, that the total daily usage of the compounds of the disclosure can be decided by the attending physician within the scope of sound medical judgment. The specific therapeutically effective dose level for any particular patient can depend upon a variety of factors including the disorder being treated and the severity of the disorder; activity of the specific synthetic compound employed; the specific pharmaceutical composition employed; the age, body weight, general health, sex and diet of the patient; the time of administration, route of administration, and rate of excretion of the specific synthetic compound employed; the duration of the treatment; drugs used in combination or coincidental with the specific synthetic compound employed; and like factors well-known in the medical arts. For example, it is well within the skill of the art to start doses of the synthetic compound at levels lower than required to achieve the desired therapeutic effect and to gradually increase the dosage until the desired effect is achieved.

Actual dosage levels of synthetic compounds in the pharmaceutical compositions of this disclosure can be varied so as to obtain an amount of the compound(s) that is effective to achieve the desired therapeutic response for a particular patient, compositions and mode of administration. The selected dosage level can depend upon the activity of the particular synthetic compound, the route of administration, the severity of the condition being treated and the condition and prior medical history of the patient being treated. However, it is within the skill of the art to start doses of the synthetic compound at levels lower than required to achieve the desired therapeutic effect and to gradually increase the dosage until the desired effect is achieved.

In on particular embodiment, the synthetic compound is administered via intravitreal injection. For example, the synthetic compound (e.g., SH-11037 (6c)) can be administered via intrvitreal injection in amounts ranging from about 0.1 µM to about 100 µM final intravitreal concentration.

The synthetic compounds of the disclosure can be administered as a pharmaceutical composition comprising the synthetic compound of interest in combination with one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the composition (e.g., synthetic compound) and not injurious to the subject. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal, subretinal, subconjunctival), drop infusion preparations, or suppositories. For application by the ophthalmic mucous membrane route, they may be formulated as eye drops or eye ointments. These compositions can be prepared by conventional means, and, if desired, the active compound (i.e., synthetic compound) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein.

The pharmaceutical compositions including the synthetic active compounds and pharmaceutical carriers used in the methods of the present disclosure can be administered to a subset of subjects in need of treatment for neovascular eye disease and treatment for angiogenesis and/or inflammation-mediated diseases. Some subjects that are in specific need of treatment for neovascular eye disease and/or treatment for angiogenesis and/or inflammation-mediated diseases may include subjects who are susceptible to, or at elevated risk of, experiencing neovascular eye disease (e.g., retinopathy of prematurity, diabetic retinopathy, "wet" age-related macular degeneration, etc.), angiogenesis (e.g., cancers, and in particular, retinoblastoma) and/or inflammation-mediated diseases, and the like. Subjects may be susceptible to, or at elevated risk of, experiencing neovascular eye disease and/or angiogenesis and/or inflammation-mediated diseases due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

The disclosure will be more fully understood upon consideration of the following non-limiting Examples.

EXAMPLES

Materials and Methods

All starting materials and reagents used in the Examples below were obtained commercially and were used without further purification. Tetrahydrofuran was distilled from sodium benzophenone ketyl. Dichloromethane and acetonitrile were freshly distilled from calcium hydride. All solvents used for routine product isolation and chromatography were of reagent grade and glass distilled. Reaction flasks were dried at 100° C. before use, and air- and moisture-sensitive reactions were performed under argon. Flash column chromatography was performed using silica gel 60 (230-400 mesh, Merck) with the indicated solvents. Thin-layer chromatography was performed using 0.25 mm silica gel plates (Merck & Co., Whitehouse Station, N.J.). Mass spectra were obtained using a Waters Auto Purification instrument, and high resolution mass spectra were obtained using a JEOL JMS-AX 505WA unit. $^1$H and $^{13}$C spectra were recorded on either a Bruker AVANCE III 400 MHz, or a Bruker AVANCE III 600 MHz spectrometer as solutions in deuteriochloroform (CDCl$_3$) and methanol-d4. $^1$H NMR data were reported in the order of chemical shift, multiplicity (s, singlet; d, doublet; t, triplet; m, multiplet and/or multiple resonances), number of protons, and coupling constant (J) in hertz (Hz).

HRECs and Attachment Factor were purchased from Cel Systems (Kirkland, Wash.). CLONETICS® HUVECs were purchased from Lonza (Walkersville, Md.). All cells were used between passages 5 and 7. Endothelial Growth Medium (EGM-2) was prepared by mixing the contents of an EGM-2 "Bullet Kit" (Cat no. CC-4176) with Endothelial Basal Medium (EBM) (Lonza). The EGM-2 "Bullet Kit" contains hydrocortisone, human fibroblast growth factor (hFGF), VEGF, R3-insulin like growth factor (R3-IGF-1), ascorbic acid, human epidermal growth factor (hEGF), gentamycin and heparin along with 2% fetal bovine serum (FBS). TNF-α and α-tubulin antibody were from Sigma (St. Louis, Mo.), and human VEGF-165 was from BioLegend (San Diego, Calif.). The antibodies for p38 MAPK, NF-κB p65 and VCAM-1 were obtained from Santa Crux (Dallas, Tex.) while the cleaved caspase-3, phospho-p38 MAPK, Akt, phospho-Akt, VEGFR2, phospho-VEGFR2, and IκB-α antibodies were from Cell Signaling (Danvers, Me.). Secondary antibodies were from Thermo Fisher Scientific (Pittsburgh, Pa.). The TaqMan probes and 5'-ethynyl-2'-deoxyuridine (EdU) incorporation assay kit were procured from Life Technologies (Carlsbad, Calif.). AbD Serotec (Kidlington, UK) was the source of the alamarBlue, while BD Biosciences (San Jose, Calif.) supplied the Matrigel. The Bradford reagent for protein estimation was prepared by dissolving 0.3 g of Coomassie G-250 (Pierce, Thermo Scientific, Life Technologies) in 500 mL of 3% perchloric acid.

Example 1

In this Example, the synthesis of cremastranone 1 is described, as diagrammed in FIG. 2.

(E)-1-(4-(benzyloxy)-6-hydroxy-2,3-dimethoxyphenyl)-3-(3-hydroxy-4-methoxyphenyl)prop-2-en-1-one. To a solution of 4'-benzyloxy-6'-hydroxy-2',3'-dimethoxyacetophenone (104 mg, 0.34 mmol) in EtOH (6 mL) was added KOH (95 mg, 1.7 mmol) and isovanillin (62 mg, 0.41 mmol) at room temperature (rt). The reaction mixture was stirred for 48 hours at rt. Evaporation of ethanol and extraction with ethyl acetate, washing with 2 N HCl solution and brine, drying over MgSO$_4$ and removal of the solvent followed by column chromatography on silica gel using hexane/ethyl acetate gave the chalcone (67 mg, 53%) as a yellow solid. $^1$H-NMR (600 MHz, CDCl$_3$) δ 13.68 (s, 1H), 7.81 (d, J=15.6 Hz, 1H), 7.75 (d, J=15.6 Hz, 1H), 7.42 (d, J=6.6 Hz, 2H), 7.38 (t, J=7.8 Hz, 2H), 7.33 (t, J=7.2 Hz, 1H), 7.26 (d, J=2.4 Hz, 1H), 7.11 (dd, J=8.4 and 2.4 Hz, 1H), 6.85 (d, J=8.4 Hz, 1H), 6.32 (s, 1H), 5.12 (s, 2H), 3.92 (s, 3H), 3.91 (s, 3H), 3.83 (s, 3H); $^{13}$C-NMR (150 MHz, CDCl$_3$) δ 192.8, 162.4, 159.1, 155.1, 148.7, 145.9, 143.5, 135.8, 135.5, 129.0, 128.7, 128.2, 127.3, 124.6, 122.8, 113.0, 110.5, 109.0, 97.7, 70.6, 61.9, 61.3, 56.0; LRMS (ESI) m/z 437 (M+H$^+$).

1-(4,6-dihydroxy-2,3-dimethoxyphenyl)-3-(3-hydroxy-4-methoxyphenyl)propan-1-one. A solution of the chalcone (40 mg, 0.11 mmol) and 10% Pd/C (20 mg) in anhydrous MeOH was placed under an atmosphere of hydrogen. After stirring for 1 hour, the reaction mixture was diluted with ethyl acetate, filtered through a Celite pad and concentrated under reduced pressure. The residue was purified by flash column chromatography on silica gel (ethyl acetate: hexanes=1:2) to afford the dihydrochalcone (30 mg, 98%) as a solid. $^1$H-NMR (600 MHz, CDCl$_3$) δ 13.23 (s, 1H), 6.81 (d, J=2.4 Hz, 1H), 6.77 (d, J=7.8 Hz , 1H), 6.71 (dd, J=8.4 and 2.4 Hz , 1H), 6.27 (s, 1H), 5.60 (s, 1H), 3.90 (s, 3H), 3.85 (s, 3H), 3.80 (s, 3H), 3.3 (t, J=7.8 Hz, 2H), 2.92 (t, J=7.8 Hz, 2H); $^{13}$C-NMR (150 MHz, CDCl$_3$) δ 207.6, 161.8, 156.2, 154.4, 145.5, 144.8, 134.7, 132.7, 119.8, 114.56, 110.7, 108.5, 99.1, 60.9, 60.6, 56.0, 44.9, 29.8; LRMS (ESI) m/z 371 (M+Na$^+$).

3-(3-(benzyloxy)-4-methoxyphenyl)-1-(4-(benzyloxy)-6-hydroxy-2,3 dimethoxyphenyl)propan-1-one. To an acetone (5 mL) solution of the dihydrochalcone (250 mg, 0.72 mmol) were added benzyl bromide (270 mg, 1.6 mmol) and K$_2$CO$_3$ (300 mg, 2.2 mmol). After refluxing for 3 hours, the reaction mixture was diluted with ethyl acetate and the organic phase was washed with water and brine, dried over MgSO$_4$ and concentrated under reduced pressure. The residue was purified by flash column chromatography on silica gel (ethyl acetate/n-hexane=1:2) to afford the dibenzylated compound (118 mg, 35%). $^1$H-NMR (600 MHz, CDCl$_3$) δ 13.29 (s, 1H), 7.42 (m, 4H), 7.38 (t, J=7.2 Hz, 2H), 7.33 (t, J=7.2 Hz, 3H), 7.26 (t, J=7.2 Hz, 1H), 6.83 (d, J=9 Hz, 1H), 6.78 (dd, J=6.0 and 1.8 Hz, 2H), 6.27 (s, 1H), 5.12 (s, 2H), 5.10 (s, 2H), 3.87 (s, 3H), 3.84 (s, 3H), 3.76 (s, 3H), 3.25 (t, J=7.2 Hz, 2H), 2.89 (t, J=7.8 Hz, 2H); $^{13}$C-NMR (150 MHz, CDCl$_3$) δ 204.8, 159.0, 155.2, 148.0, 137.2, 135.7, 134.9, 134.0, 128.7, 128.5, 128.2, 127.7, 127.3, 127.2, 120.9, 114.7, 111.9, 108.4, 97.3, 71.0, 70.5, 6101, 61.0, 56.1, 45.0, 29.9; LRMS (ESI) m/z 527 (M−H$^+$).

7-(benzyloxy)-3-(3-(benzyloxy)-4-methoxybenzyl)-5,6-dimethoxy-4H-chromen-4-one. To a solution of the dibenzylated dihydrochalcone (93 mg, 0.2 mmol) in toluene (5 mL) was added N,N-dimethylformamide dimethyl acetal (43 mg, 0.36 mmol). After refluxing for 6 hours, the reaction mixture was cooled and concentrated under reduced pressure. The residue was purified by flash column chromatography on silica gel (ethyl acetate/n-hexane=1:2) to afford the chromone (76 mg, 80%) as a solid. $^1$H-NMR (600 MHz, CDCl$_3$) δ 7.44(d, J=8.4 Hz, 2H), 7.40(t, J=7.2. Hz, 4H), 7.34(t, J=6 Hz, 1H), 7.29(t, J=7.2 Hz, 2H), 7.22(m, 2H), 6.80(s, 2H), 6.77(s, 1H), 6.63(s, 1H), 5.16(s, 2H), 5.09(s, 2H), 3.95(s, 3H), 3.89(s, 3H), 3.93(s, 3H), 3.62(s, 2H); $^{13}$C-NMR (150 MHz, CDCl$_3$) δ 175.9, 156.6, 154.5, 152.8, 151.0, 148.3, 148.0, 140.6, 137.1, 135.6, 131.2, 128.7, 128.4, 128.3, 127.7, 127.4, 127.2, 125.0, 121.8, 115.3, 113.1, 112.0, 97.4, 71.0, 70.8, 62.1, 61.5, 56.1, 30.8; LRMS (ESI) m/z 561 (M+Na$^+$).

7-hydroxy-3-(3-hydroxy-4-methoxybenzyl)-5,6-dimethoxychroman-4-one. A solution of the chromone (35 mg, 0.07 mmol) and 10% Pd/C (10 mg) in anhydrous MeOH was placed under an atmosphere of hydrogen. After stirring for 1 hour, the reaction mixture was diluted with ethyl acetate, filtered through a Celite pad and concentrated under reduced pressure. The residue was purified by flash column chromatography on silica gel (ethyl acetate:hexanes=1:1) to afford the chromanone (19 mg, 87%) as a solid.; $^1$H-NMR (600 MHz, CD$_3$OD) δ 6.82(d, J=14.4 Hz, 1H), 6.67(d, J=1.8 Hz, 1H), 6.63(dd, J=8.4 and 2.4 Hz, 1H), 6.16(s, 1H), 4.21(dd, J=11.4 and 4.2 Hz, 1H), 4.04(dd, J=11.4 and 7.2 Hz, 1H), 3.82(s, 3H), 3.79(s, 3H), 3.75(s, 3H), 3.00(dd, J=13.2 and 4.2 Hz, 1H), 2.66(m, 1H), 2.58(dd, J=13.8 and 10.8 Hz, 1H); $^{13}$C-NMR (150 MHz, CD$_3$OD) δ 192.4, 160.0, 158.5, 154.4, 146.3, 146.2, 136.4, 131.2, 119.9, 115.6, 111.5, 107.3, 99.1, 68.6, 60.4, 60.1, 55.0, 48.2, 32.0; LRMS (ESI) m/z 383 (M+Na$^+$).

Cremastranone (1). To a solution of 7-hydroxy-3-(3-hydroxy-4-methoxybenzyl)-5,6-dimethoxychroman-4-one (17 mg, 0.047 mmol) in CHCl$_3$ (2 mL) was added TMSI (15 μL) at 0° C. and the reaction mixture was heated at 60° C. for 4 hours. The mixture was concentrated in vacuo. The residue was purified by flash column chromatography on silica gel (Ethyl acetate/n-hexane=1:1) to afford cremastranone (1) (12 mg, 74%). $^1$H-NMR (600 MHz, CD$_3$OD) δ 6.85 (d, J=8.4 Hz, 1H), 6.70 (d, J=1.8 Hz, 1H), 6.68 (dd, J=8.4 and 2.4 Hz, 1H), 5.91 (s, 1H), 4.23 (dd, J=11.4 and 4.2 Hz, 1H), 4.06 (dd, J=11.4 and 7.2 Hz, 1H), 3.82 (s, 3H), 3.77 (s, 3H), 3.08 (dd, J=13.8 and 4.8 Hz, 1H), 2.82 (m, 1H), 2.63 (dd, J=13.8 and 4.2 Hz, 1H); $^{13}$C-NMR (150 MHz, CD$_3$OD) δ 200.1, 160.6, 160.1, 156.8, 147.8, 147.6, 132.2, 130.4, 121.3, 117.0, 112.9, 102.9, 95.7, 70.3, 60.9, 56.4, 47.9, 33.1; LRMS (ESI) m/z 345 (M−H$^+$).

Example 2

In this Example, the synthesis of SH-11052 (2) and cremastranone analogs 3a-b, 4a-c, 5, 6a-b, 7, 8a-d, and 9a-b is described.

More specifically, as illustrated in the schematic shown in FIG. 3, and discussed more fully herein, the synthesis of SH-11052 (2) commenced with aldol condensation of the 6'-hydroxy-2',3',4'-trimethoxy-acetophenone, which was prepared from 3',4',5'-trimethoxyphenol by ortho-acetylation (discussed below).

1-(6-hydroxy-2,3,4-trimethoxyphenyl)ethanone. To an acetic anhydride (2 mL) solution of 3,4,5-trimethoxyphenol (1.2 g, 6.6 mmol), BF$_3$-Et$_2$O (0.07 mL) was added at 0° C. After stirring at 60° C. for 3 hours, the reaction mixture was diluted with ethyl acetate and the reaction mixture was cooled to ca. 0° C. for 2 hours and the crystallized cake filtered with ethyl acetate. H$_2$O (10 mL) and Et$_3$N (1 mL) were added. After stirring for 1 hour at room temperature, the reaction mixture was diluted with ethyl acetate and the organic phase was washed with water and brine, dried over MgSO$_4$ and concentrated under reduced pressure. The residue was purified by flash column chromatography (Ethyl acetate/n-hexanes=1:1) to afford the methyl ketone (1.4 g, 95%).

The aldol condensation of the 6'-hydroxy-2',3',4'-trimethoxy-acetophenone includes aldol condensation with 3-benzyloxy-4-methoxybenzaldehyde to afford the resulting chalcone in moderate yield.

(E)-3-(3'-benzyloxy-4'-methoxyphenyl)-1-(6-hydroxy-2,3,4-trimethoxyphenyl)prop-2-en-1-one (3a). To a solution of methyl ketone (1.5 g, 6.5 mmol) in MeOH (10 mL) was added 3-benzyloxy-4-methoxybenzaldehyde (2.0 g, 8.0 mmol) and KOH (1.5 g, 25 mmol) at 0° C., then warmed to room temperature. The reaction mixture was stirred at 35° C. for 72 hours followed by the addition of water and dilution with CH$_2$Cl$_2$. The organic layer was washed with water and brine, dried over MgSO$_4$, and concentrated in vacuo. The residue was purified by silica gel column chromatography (Ethyl acetate/n-hexane=1:3) to afford 3'-benzyloxy-4'-methoxychalcone (3a) (1.6 g, 56%). $^1$H-NMR (600 MHz, CDCl$_3$) δ 13.7 (s,1H), 7.74 (s, 2H), 7.47 (d, 2H, J=7.2 Hz); 7.40 (t, 2H, J=7.2 Hz); 7.33 (d, 1H, J=7.2 Hz); 7.24 (dd, 1H, J=8.4 and 2.4 Hz); 7.17 (d, 1H, J=1.2 Hz); 6.92 (d, 1H, J=8.4 Hz); 6.28 (s, 1H), 5.22 (s, 2H), 3.94 (s, 3H), 3.89 (s, 3H), 3.84 (s, 3H), 3.83 (s, 3H); $^{13}$C-NMR (150 MHz, CDCl$_3$) δ 192.7, 162.6, 159.9, 154.9, 151.9, 148.3, 143.5, 136.7, 135.2, 128.7, 128.2, 128.0, 127.2, 124.2, 123.5, 113.0, 111.5, 108.7, 96.6, 71.12, 61.9, 61.32, 56.12, 29.7; LRMS (ESI) m/z 315 (M+H).

Catalytic hydrogenation of the chalcone (3a) under HCO$_2$Na and Pd/C afforded the dihydrochalcone (4a). The chromanone ring was constructed by hydroxymethylation and cyclization. To this end, the desired chromanone 6a was obtained in good yield by aldol reaction with formaldehyde under basic conditions, and subsequent treatment with K$_2$CO$_3$ of the concomitant compounds 5 and 7.

1-(6-hydroxy-2,3,4-trimethoxyphenyl)-3-(3'-hydroxy-4'-methoxyphenyl)propan-1-one (4a). To 3'-(benzyloxy)-4'-methoxychalcone (3a) (850 mg, 1.9 mmol) in isopropanol (10 mL) was added HCO$_2$Na (513 mg, 7.5 mmol), Pd/C (195 mg, 1.8 mmol) and HCO$_2$H (1 mL) at 0° C. The reaction mixture was stirred at 60° C. for 6 hours. The mixture was filtered through a short pad of silica gel. After the filtrate was concentrated in vacuo, purification of the residue via flash column chromatography on silica gel (Ethyl acetate/n-hexane=1:3) afforded dihydrochalcone (4a) (517 mg, 79%). $^1$H-NMR (400 MHz, CDCl$_3$) δ 13.38 (s, 1H), 6.82 (d, 1H, J=8.28 Hz); 6.73 (s, 2H), 6.21 (s, 1H), 5.53 (s, 1H), 3.93 (s, 3H), 3.85 (d, 6H, J=1.96 Hz); 3.74 (s, 3H), 3.31 (m, 2H), 2.94 (d, 2H, J=7.8 Hz); $^{13}$C-NMR (100 MHz, CDCl$_3$) δ 204.8, 161.7, 159.8, 155.0, 146.3, 143.7, 134.6, 133.3, 120.7, 114.2, 111.1, 108.1, 96.1, 61.0, 60.9, 55.9, 55.7, 45.1, 30.2; LRMS (ESI) m/z 317 (M+H).

3-(3'-hydroxy-4'-methoxybenzyl)-3-(hydroxymethyl)-5,6,7-trimethoxychroman-4-one (5) and 1-(6-hydroxy-2,3,4-trimethoxyphenyl)-2-(3'-hydroxy-4'-methoxybenzyl)prop-2-en-1-one (7). The dihydrochalcone (4a) (700 mg, 1.9 mmol) was dissolved in 50% aqueous NaOH (0.96 mL), H$_2$O (3.8 mL) and stirred with formalin (0.16 mL, 5.8 mmol) at 60° C. for 3 hours. After stirring for 3 hours, the reaction mixture was diluted with ethyl acetate and washed with NH$_4$Cl and brine, dried over MgSO$_4$ and concentrated under reduced pressure. The residue was purified by flash column chromatography on silica gel (Ethyl acetate/nhexane=1:2) to afford a mixture of compound (5) (383 mg, 54%), (6a) (71 mg, 10%) and (7) (106 mg, 15%), respectively. For compound (5), $^1$H-NMR (400 MHz, CDCl$_3$) δ 6.83-6.80 (m, 2H), 6.75-6.73 (m, 1H), 6.28 (s, 1H), 5.78 (bs, 1H), 4.04-4.03 (m, 2H), 3.91 (s,3H), 3.88 (s, 3H), 3.84 (s, 3H), 3.79 (s, 2H), 3.58-3.50 (m, 2H), 3.21 (bs, 1H), 2.98 (d,1H, J=13 Hz); 2.85 (d, 1H, J=14 Hz); $^{13}$C-NMR (100 MHz, CDCl$_3$) δ 196.1, 159.7, 159.4, 154.5, 146.3, 144.5, 137.5, 126.7, 123.3, 114.1, 113.0, 107.8, 95.9, 69.6, 62.2, 61.4, 61.2, 56.0, 55.8, 49.9, 34.8. LRMS (ESI) m/z 405 (M+H); For compound (7), $^1$H-NMR (400 MHz, CDCl$_3$) δ 11.7 (s, 1H), 7.29 (s, 1H), 7.18 (s, 1H), 6.79 (d, 1H, J=7.8 Hz); 6.67-6.65 (m, 2H), 6.19 (s, 1H), 5.44 (s, 1H), 5.10 (s, 1H), 4.96 (s, 1H), 3.82 (s,3H), 3.79 (s, 3H), 3.71 (s, 3H), 3.66 (s, 3H), 3.56 (s, 2H); $^{13}$C-NMR (100 MHz, CDCl$_3$) δ 201.7, 160.6, 160.2, 151.8, 146.4, 144.1, 134.9, 129.7, 128.3, 122.2, 115.3, 114.2, 112.0, 108.3, 95.9, 61.4, 61.0, 56.1, 55.8, 38.6; LRMS (ESI) m/z 375 (M+H).

3-(3'-hydroxy-4'-methoxybenzyl)-5,6,7-trimethoxychroman-4-one (6a). The compound (5) (100 mg, 0.25 mmol)

was dissolved in ethanol (2 mL), and stirred with $K_2CO_3$ (54 mg, 0.49 mmol) at 90° C. for 3 hours. After stirring for 3 hours, the reaction mixture was diluted with ethyl acetate and washed with 1 N HCl and brine, dried over $MgSO_4$ and concentrated under reduced pressure. The residue was purified by flash column chromatography on silica gel (Ethyl acetate/n-hexane=1:2) affording 5,6,7-trimethoxychromanone (6a) (45 mg, 49%). $^1$H-NMR (400 MHz, $CDCl_3$) δ 7.24 (s, 1H), 6.83 (d, 1H, J=7.8 Hz); 6.71 (d, 2H, J=1.9 Hz); 6.23 (s, 1H), 5.53 (s, 1H), 4.23 (m, 1H), 4.10 (m, 1H), 3.91 (s, 3H), 3.85 (d, 6H, J=1.9 Hz); 3.79 (s, 3H), 3.16 (m, 1H), 2.70 (m, 1H), 2.63 (m, 1H); $^{13}$C-NMR (100 MHz, $CDCl_3$) δ 191.3, 159.6, 159.2, 154.4, 146.5, 144.2, 137.4, 130.2, 121.8, 114.3, 111.4, 108.6, 95.9, 69.0, 61.5, 61.2, 56.0, 55.9, 48.5, 32.5; LRMS (ESI) m/z 375 (M+H). From the compound (7) (100 mg, 0.27 mmol), the same reaction conditions afforded 5,6,7-trimethoxychromanone (6a) (72 mg, 72%).

SH-11052 (2). To a solution of 5,6,7-trimethoxychromanone (6a) (37 mg, 0.10 mmol) in $CHCl_3$ (1 mL) was added TMSI (113 μL, 0.80 mmol) at 0° C. and the reaction mixture was heated at 60° C. for 4 hours. The mixture was concentrated in vacuo. The residue was purified by flash column chromatography on silica gel (Ethyl acetate/n-hexane=1:1) to afford SH-11052 (2) (17 mg, 49%). $^1$H-NMR (600 MHz, $CD_3OD$) δ 6.85 (d, 1H, J=8.4 Hz), 6.70 (d, 1H, J=2.4 Hz), 6.67 (dd, 1H, J=2.4 and 8.4 Hz), 6.13 (s, 1H), 4.25 (dd, 1H, J=4.2 and 11.4 Hz), 4.09 (dd, 1H, J=7.8 and 11.4 Hz), 3.87 (s, 3H), 3.82 (s, 3H), 3.08 (dd, 1H, J=4.8 and 13.8 Hz), 2.84-2.79 (m, 1H), 2.64 (dd, 1H, J=10.2 and 13.8 Hz); $^1$H-NMR (600 MHz, $CDCl_3$) δ 11.7 (s, 1H), 6.78 (d, 1H, J=2.4 Hz), 6.78 (d, 1H, J=9.6 Hz), 6.67 (dd, 1H, J=2.4 and 8.4 Hz), 6.02 (s, 1H), 5.60 (s, 1H), 5.02 (s, 1H), 4.25 (dd, 1H, J=4.2 and 11.4 Hz), 4.10 (dd, 1H, J=7.8 and 11.4 Hz), 3.88 (s, 3H), 3.85 (s, 3H), 3.15 (dd, 1H, J=4.8 and 13.8 Hz), 2.82-2.78 (m, 1H), 2.64 (dd, 1H, J=10.8 and 14.4 Hz); $^{13}$C-NMR (150 MHz, $CD_3OD$) δ 200.7, 157.6, 157.6, 150.4, 148.0, 147.8, 132.4, 128.7, 121.4, 117.1, 113.0, 103.5, 92.25, 70.63, 56.82, 56.58, 33.26; $^{13}$C-NMR (150 MHz, $CDCl_3$) δ 200.7, 158.0, 156.6, 150.1, 147.7, 147.4, 133.0, 129.2, 122.6, 117.1, 112.8, 104.4, 93.0, 71.4, 58.3, 58.0, 48.8, 34.1; LRMS (EI) m/z 346 (M+); HRMS (EI) m/z 346.1057 (M+) [calc. $C_{18}H_{18}O_7$ 346.1053].

To a solution of 5,6,7-trimethoxychromanone (6a) (37 mg, 0.1 mmol) in $CHCl_3$ (1 mL) 2 equivalents of TMSI was added at 0° C. and the reaction mixture was heated at 60° C. for 4 hours to selectively remove a methyl group at C-5. The mixture was concentrated in vacuo. The residue was purified by flash column chromatography on silica gel (Ethyl acetate/n-hexane=1:1) to afford compound (8a) ($R_1$=OH, $R_2$ and $R_3$=OMe).

5,6,7-trihydroxy-3-(3-hydroxy-4-methoxybenzyl)chroman-4-one (8d). To a $CHCl_3$ solution (2 mL) of 5,6,7-trimethoxychromanone (37 mg, 0.10 mmol) was added TMSI (1.1 mL) at 0° C. After heating at 60° C. for 6 hours, the reaction mixture was cooled to room temperature, and concentrated under reduced pressure. The residue was purified by flash column chromatography on silica gel (Ethyl acetate/n-hexane=1:1) to afford the tridemethylated homoisoflavanone (8d) (12 mg, 36%). $^1$H-NMR (600 MHz, $CD_3OD$) δ 6.70 (d, 1H, J=8.4 Hz), 6.67 (d, 1H, J=1.8 Hz), 6.55 (dd, 1H, J=8.1 and 2.4 Hz), 6.13 (s, 1H), 4.25 (dd, 1H, J=11 and 4.2 Hz), 4.08 (dd, 1H, J=7.8 and 4.8 Hz), 3.87 (s, 3H), 3.05 (dd, 1H, J=14 and 4.8 Hz), 2.78 (m, 1H), 2.61 (dd, 1H, J=14 and 10 Hz).

Example 3

In this Example, the synthesis of cremastranone analogs (analog compounds 6b and 8b) is described, as diagrammed in FIG. 3.

3-(3,4-dimethoxyphenyl)-1-(6-hydroxy-2,3,4-trimethoxyphenyl)propan-1-one (4b). A solution of chalcone (3b) (102 mg, 0.32 mmol) and 10% Pd/C (16 mg) in anhydrous EtOH (3 mL) was placed under an atmosphere of hydrogen. After stirring for 4 hours, the reaction mixture was diluted with ethyl acetate, filtered through a short pad of silica gel and concentrated in vacuo. The residue was purified by flash column chromatography on silica gel (Ethyl acetate/n-hexane=1:1) to afford dihydrochalcone (4b) (115 mg, 96%). $^1$H-NMR (400 MHz, $CDCl_3$) δ 13.33 (s, 1H), 7.21 (m, 4H), 7.18 (s, 1H), 6.17 (s, 1H), 3.88 (s, 3H), 3.81 (s, 3H), 3.69 (s, 3H), 3.31 (m, 2H), 2.97 (d, 2H, J=7.8 Hz); $^{13}$C-NMR (100 MHz, $CDCl_3$) δ 204.7, 161.8, 159.9, 155.0, 141.4, 134.7, 128.4, 125.9, 108.2, 96.1, 61.0, 60.9, 56.0, 44.7, 30.4. IR (neat) $v_{max}$ 2960, 2924, 2852 $cm^{-1}$; LRMS (ESI) m/z 317 (M+H).

3-benzyl-5,6,7-trimethoxychroman-4-one (6b). The dihydrochalcone (4b) (100 mg, 0.31 mmol) was dissolved in 50% aqueous NaOH (2 mL), $H_2O$ (6 mL) and stirred with formalin (0.04 mL, 1.61 mmol) at 60° C. for 3 hours. After stirring for 3 hours, the reaction mixture was diluted with ethyl acetate and washed with $NH_4Cl$ and brine, dried over $MgSO_4$ and concentrated under reduced pressure. The residue was purified by flash column chromatography on silica gel (Ethyl acetate/n-hexane=1:4) to afford compound 6b (44 mg, 42%), $^1$H-NMR (400 MHz, $CDCl_3$) δ 7.31-7.28 (m, 2H), 7.22-7.20 (m, 3H), 6.23 (s, 1H), 4.27 (dd, 1H, J=11 and 3.9 Hz), 4.09 (dd, 1H, J=11 and 7.8 Hz), 3.91 (s, 3H), 3.86 (s, 3H), 3.79 (s, 3H), 3.28 (dd, 1H, J=14 and 3.9 Hz), 2.80-2.73 (m, 1H), 2.68 (dd, 1H, J=14 and 11 Hz); $^{13}$C-NMR (100 MHz, $CDCl_3$) δ 191.1, 159.6, 159.2, 154.4, 138.5, 137.4, 129.1, 128.6, 126.5, 108.6, 95.9, 69.0, 61.5, 61.3, 56.0, 48.2, 32.7.

3-benzyl-5-hydroxy-6,7-dimethoxychroman-4-one (8b). To a solution of 3-benzyl-5,6,7-methoxychromanone (6b) (15 mg, 0.046 mmol) in AcOH (0.75 mL) was added HBr (0.5 mL) at 0° C. The reaction mixture was refluxed for 2 hours. After cooling to room temperature, the reaction mixture was diluted with ethyl acetate and the organic phase was washed with water and brine, dried over $MgSO_4$ and concentrated under reduced pressure. The residue was purified by flash column chromatography on silica gel (Ethyl acetate/n-hexane=1:2) to afford 3-benzyl-6,7-dimethoxychromanone (8b) (5 mg, 35%). $^1$H-NMR (400 MHz, $CDCl_3$) δ 11.96 (s, 1H), 7.35-7.31 (m, 2H), 7.27-7.22 (m, 3H), 6.02 (s, 1H), 4.29 (dd, 1H, J=11 and 4.4 Hz), 4.13 (dd, 1H, J=11 and 7.3 Hz), 3.88 (s, 3H), 3.83 (s, 3H), 3.29 (dd, 1H, J=14 and 4.4 Hz), 2.90-2.83 (m, 1H), 2.76 (dd, 1H, J=14 and 11 Hz); LRMS (ESI) m/z 315 (M+H).

Example 4

In this Example, the synthesis of cremastranone analogs (analog compounds 9a-b) is described. Analog (9a) was prepared from compound (4a) and analog (9b) was prepared from compound (4b) as described below.

3-(3'-hydroxy-4'-methoxybenzyl)-5,6,7-trimethoxy-4H-chromen-4-one (9a). A solution of $PCl_5$ (180 mg, 0.86 mmol) in DMF (2.5 mL) was stirred at 20° C. for 20 minutes. To the reaction mixture was added $BF_3-Et_2O$ (0.22 mL, 1.73 mmol) and the dihydrochalcone (4a) (prepared as described above) (200 mg, 0.58 mmol) at 20° C., then stirred 4 hours followed by the addition of 1 N HCl (2 mL) and dilution with ethyl acetate. The organic layer was washed with water and brine, dried over $MgSO_4$, and concentrated in vacuo. The residue was purified by silica gel column chromatography (Ethyl acetate/n-hexane=1:4) to afford chromone (9a) (110 mg, 51%). $^1$H-NMR (400 MHz, $CDCl_3$) δ 7.34 (s, 1H), 6.83-$_6$.79 (m, 2H), 6.74-6.73 (m, 1H), 6.59 (s, 1H), 5.49 (s, 1H), 3.94 (s, 3H), 3.90 (s, 3H), 3.86 (s, 3H), 3.67 (s, 2H); $^{13}$C-NMR (100 MHz, $CDCl_3$) δ 175.9, 157.5, 154.7, 152.6, 151.0, 146.5, 144.1, 140.2, 130.6, 125.2, 121.6, 114.3, 112.9, 111.7, 95.9, 62.0, 61.4, 56.2, 55.9, 31.1. LRMS (ESI) m/z 373 (M+H).

3-benzyl-5,6,7-trimethoxy-4H-chromen-4-one. A solution of $PCl_5$ (50 mg, 0.24 mmol) in DMF (1.2 mL) was stirred at 20° C. for 20 minutes. To the reaction mixture was added $BF_3$-$Et_2O$ (0.06 mL, 0.48 mmol) and the dihydrochalcone (4b) (prepared as described above) (51 mg, 0.16 mmol) at 20° C., then stirred 4 hours followed by the addition of 1 N HCl (2 mL) and dilution with ethyl acetate. The organic layer was washed with water and brine, dried over $MgSO_4$, and concentrated in vacuo. The residue was purified by silica gel column chromatography (Ethyl acetate/n-hexane=1:4) to afford the chromone (31 mg, 59%). $^1$H-NMR (400 MHz, $CDCl_3$) δ 7.38 (s, 1H), 7.26 (d, 5H, J=10.72 Hz); 6.61 (s, 1H), 3.97 (s, 3H), 3.92 (s, 3H), 3.88 (s, 3H), 3.76 (s, 2H); $^{13}$C-NMR (100 MHz, $CDCl_3$) δ 191.1, 159.6, 159.2, 154.4, 138.5, 137.4, 129.1, 128.6, 126.5, 108.6, 95.9, 69.0, 61.5, 61.3, 56.0, 48.2, 32.7.

3-benzyl-5,7-dihydroxy-6-methoxy-4H-chromen-4-one (9b). To a solution of the chromone prepared above (20 mg, 0.061 mmol) in acetic acid (1 mL) was added dropwise of 47% HBr (0.5 mL) at 0° C. The reaction mixture was refluxed for 2 hours then dried over $MgSO_4$, and concentrated in vacuo. The residue was purified by silica gel column chromatography (Ethyl acetate/n-hexane=1:2) to afford the demethylated chromone (9b) (10 mg, 55%). $^1$H-NMR (400 MHz, $CDCl_3$) δ 12.42 (s, 1H), 7.51 (s, 1H), 7.30 (d, 4H, J=10.72 Hz); 6.42 (s, 1H), 5.28 (s, 1H), 4.12 (dd, 1H, J=6.84 and 7.32 Hz); 3.94 (s, 3H), 3.75 (s, 2H). LRMS (ESI) m/z 299 (M+H).

Example 5

In this Example, the method for synthesizing cremastranone analogs (analog compounds 10b, 11a-k and 6c) is described.

5,7-dihydroxy-6-methoxychroman-4-one (10b). As illustrated in the schematic shown in FIG. 4, to a $CHCl_3$ (2 mL) solution of 5,6,7-trimethoxychromanone 10a (commercially available from Netchem, Inc.) (20 mg, 0.08 mmol) TMSI (97 μL, 0.48 mmol) was added at 0° C. After stirring for 3 hours at 60° C., the reaction mixture was diluted with ethyl acetate and the organic phase was washed with water and brine, dried over $MgSO_4$ and concentrated in vacuo. The residue was purified by flash column chromatography on silica gel (Ethyl acetate/n-hexane=1:1) to afford the demethylated chromanone (10b) (14 mg, 85%). $^1$H-NMR (400 MHz, $CDCl_3$) δ 11.69 (s, 1H), 6.03 (s, 1H), 5.01 (s, 1H), 4.43 (t, 2H, J=6.3 Hz); 3.88 (s, 3H), 2.77 (t, 2H, J=6.3 Hz); $^{13}$C-NMR (100 MHz, $CDCl_3$) δ 196.6, 156.1, 154.6, 147.9, 127.1, 103.2, 91.1, 66.8, 56.2, 36.6; LRMS (ESI) m/z 211 (M+H).

(E)-3-(3'-hydroxy-4'-methoxybenzylidene)-5,6,7-trimethoxychroman-4-one (11a). As illustrated in the schematic shown in FIG. 4, to a solution of 5,6,7-trimethoxychromanone (10a) (commercially available from Netchem, Inc.) (238 mg, 1 mmol) in benzene (25 mL) was added isovanillin (170 mg, 1.1 mmol) and PTSA (20 mg, 0.1 mmol) at 0° C. The reaction mixture was refluxed for 12 hours. After cooling to room temperature, the reaction mixture was concentrated in vacuo. The residue was purified by flash column chromatography on silica gel (Ethyl acetate/n-hexane=1:1) to afford 4-benzylidene-5,6,7-trimethoxychromanone (11a) (215 mg, 58%). $^1$H-NMR (600 MHz, $CDCl_3$) δ 7.74 (s, 1H), 6.91-6.84 (m, 3H), 6.26 (s, 1H), 5.67 (s, 1H), 5.24 (d, 2H, J=1.8 Hz); 3.98 (s, 3H), 3.94 (s, 3H), 3.88 (s, 3H), 3.83 (s, 3H); $^{13}$C-NMR (100 MHz, $CDCl_3$) δ 179.5, 159.3, 159.1, 154.7, 147.5, 145.5, 137.8, 136.2, 130.1, 128.1, 123.2, 115.7, 110.5, 96.1, 67.6, 61.6, 61.3, 60.3, 60.3, 56.0, 55.9; LRMS (ESI) m/z 373 (M+H).

(E)-3-(3'-benzyloxy-4'-methoxybenzylidene)-5,6,7-trimethoxychroman-4-one (11b). As illustrated in the schematic shown in FIG. 4, to an acetone (5 mL) solution of 4-benzylidenechromanone (11a) (124 mg, 0.33 mmol) benzyl bromide (70 mg, 0.4 mmol) and $K_2CO_3$ (144 mg, 0.80 mmol) were added. After stirring for 3 hours at room temperature, the reaction mixture was diluted with ethyl acetate and the organic phase was washed with water and brine, dried over $MgSO_4$ and concentrated under reduced pressure. The residue was purified by flash column chromatography on silica gel (Ethyl acetate/n-hexane=1:1) to afford benzylated chromanone (11b) (120 mg, 79%). $^1$H-NMR (400 MHz, $CDCl_3$) δ 7.67 (s, 1H), 7.42-7.24 (m, 5H), 6.93 (d, 1H, J=8.3 Hz); 6.87 (dd, 1H, J=8.3 and 2.0 Hz); 6.75 (d, 1H, J=2.0 Hz); 6.22 (s, 1H), 5.17 (s, 2H), 5.03 (d, 2H, J=1.5 Hz); 3.95 (s, 3H), 3.92 (s, 3H), 3.86 (s, 3H), 3.81 (s, 3H), $^{13}$C-NMR (100 MHz, $CDCl_3$) δ 179.4, 159.3, 159.1, 154.7, 150.8, 147.8, 137.8, 136.7, 136.2, 129.9, 128.6, 128.0, 127.3, 127.1, 124.0, 115.9, 111.5, 110.5, 96.1, 71.1, 67.4, 61.6, 61.3, 56.1, 56.0; LRMS (ESI) m/z 463 (M+H).

(E)-3-(3'-allyloxy-4'-methoxybenzylidene)-5,6,7-trimethoxychroman-4-one (11). To an acetone (2 mL) solution of 4-benzylidenechromanone (11a) (9.9 mg, 0.02 mmol) allyl bromide (2.5 μL, 0.02 mmol) and $K_2CO_3$ (18 mg, 0.10 mmol) were added. After stirring for 3 hours at room temperature, the reaction mixture was diluted with ethyl acetate and the organic phase was washed with water and brine, dried over $MgSO_4$ and concentrated under reduced pressure. The residue was purified by flash column chromatography (Ethyl acetate/hexanes=1:1) to afford the allylated chromanone (11c) (6.8 mg, 83%). $^1$H-NMR (600 MHz, $CDCl_3$) δ 7.75 (s, 1H), 6.93 (d, 1H, J=8.4 Hz), 6.88 (dd, 1H, J=8.4 and 1.8 Hz), 6.83 (d, 1H, J=1.8 Hz), 6.25 (s, 1H), 6.11-6.04 (m, 1H), 5.43-5.40 (m, 1H), 5.33-5.31 (m, 1H), 5.23 (d, 1H, J=1.8), 4.64 (m, 2H), 3.97 (s, 3H), 3.91(s, 3H), 3.88 (s, 3H), 3.83 (s, 3H); $^{13}$C-NMR (150 MHz, $CDCl_3$) δ 179.51, 159.32, 159.19, 154.78, 150.57, 147.82, 137.88, 136.36, 133.05, 130.01, 127.41, 123.76, 118.32, 115.26, 111.36, 110.64, 96.15, 69.99, 67.70, 61.66, 61.35, 56.13, 56.01; LRMS (ESI) m/z 413 (M+H).

(E)-5,6,7-trimethoxy-3-(4-methoxy-3-(2-(pyrrolidin-1-yl)ethoxy)benzylidene)chroman-4-one (11k). To an acetone solution (5 mL) of 4-benzylidenechromanone (11a) (22 mg, 0.059 mmol) were added 1-(2-chloroethyl)pyrrolidine hydrochloride (9.4 mg, 0.071 mmol) and $K_2CO_3$ (41 mg, 0.30 mmol). After refluxing for 3 hours, the reaction mixture was diluted with ethyl acetate and the combined organic phase was washed with water and brine, dried over $MgSO_4$ and concentrated under reduced pressure. The residue was purified by flash column chromatography on silica gel (Ethyl acetate/n-hexane=1:1) to afford the alkylated 4-benzylidenechromanone (11k) (8 mg, 29% and BRSM 52%). $^1$H-NMR (600 MHz, $CDCl_3$) δ 7.75 (s, 1H), 6.92 (d, 1H, J=8.4 Hz), 6.89 (d, 1H, J=1.8 Hz), 6.87 (d, 1H, J=1.8 Hz), 6.25 (s, 1H), 5.24 (d, 2H, J=1.8 Hz), 4.21 (bs, 2H), 3.98 (s, 3H), 3.90 (s, 3H), 3.88 (s, 3H), 3.83 (s, 3H), 3.03 (bs, 2H), 2.74 (bs, 2H), 1.85 (bs, 4H); $^{13}$C-NMR (150 MHz, CDCl$_3$) δ 179.4, 178.8, 163.4, 162.9, 162.8, 162.7, 158.0, 154.8, 152.5, 151.1, 150.9, 149.2, 145.5, 145.3, 142.6, 141.9, 140.2, 139.6, 134.1, 130.3, 129.4, 121.9, 109.7, 96.1, 67.6, 62.0, 61.6, 61.4, 61.3, 56.2, 56.1, 55.9; LRMS (ESI) m/z 470 (M+H).

(2S)-2-methoxy-5-((5,6,7-trimethoxy-4-oxochroman-3-yl)methyl)phenyl 2-((tert-butoxycarbonyl)amino)-3-phenylpropanoate (6c, SH-11037). To a CH$_2$Cl$_2$ solution (2 mL) of 5,6,7-trimethoxyhomoisoflavanone (12 mg, 0.032 mmol) were added Boc-Phe-OH (10 mg, 0.035 mmol), EDCI (6.7 mg, 0.035 mmol) and DMAP (0.8 mg, 0.006 mmol). After stirring for 3 hours, the reaction mixture was diluted with ethyl acetate and washed with water and brine, dried over MgSO$_4$ and concentrated under reduced pressure. The residue was purified by flash column chromatography on silica gel (ethyl acetate/n-hexane=1:2) to afford the acylated chromanone (6c) (12 mg, 60%). $^1$H-NMR (600 MHz, CDCl$_3$) δ 7.34 (m, 2H), 7.29 (m, 3H), 7.08 (dd, 1H, J=8.4 and 1.8 Hz), 6.92 (d, 1H, J=8.4 Hz), 6.83 (bs, 1H), 6.25 (s, 1H) 4.88 (m, 1H), 4.29 (dd, 1H, J=14 and 4.2 Hz), 4.10 (m, 1H), 4.13.4.07 (m, 2H), 3.93 (s, 3H), 3.88(s, 3H), 3.81 (s, 3H), 3.80 (s, 3H), 3.35 (m, 1H), 3.23 (m, 1H), 3.19 (m,1H), 2.72 (m, 1H), 2.64 (m, 1H), 1.42 (s, 9H); $^{13}$C-NMR (150 MHz, CDCl$_3$) δ 191.0, 170.2, 159.7, 159.4, 154.4, 150.9, 137.5, 136.0, 131.0, 129.6, 128.5, 127.0, 122.6, 121.$_3$,$_1$13.1, 112.6, 108.6, 96.0, 79.9, 69.0, 61.6, 61.3, 56.1,55.8, 54.3, 48.2, 38.2, 32.7, 31.8, 28.3; LRMS (ESI) m/z 644 (M+Na).

Example 6

In this Example, the method for synthesizing cremastranone analog 12 is described, as diagrammed in FIG. 4.

Ethyl 4-(3,4,5-trimethoxyphenoxy)butanoate. To an acetone solution (10 mL) of 3,4,5-trimethoxyphenol (500 mg, 2.7 mmol) was added K$_2$CO$_3$ (1.5 g, 11 mmol) and ethyl 4-bromobutyrate (1.3 mL, 7.9 mmol). After refluxing for 12 hours, the reaction mixture was cooled to room temperature and then filtered via a short pad of silica gel to remove excess K$_2$CO$_3$. The filtrate was concentrated under reduced pressure and the resulting residue was purified by flash column chromatography on silica gel (Ethyl acetate/n-hexane=1:3) to afford ethyl 4-(3,4,5-trimethoxyphenoxy) butanoate (829 mg, 92%). $^1$H-NMR (600 MHz, CDCl$_3$) δ 6.06 (q, 1H), 4.08-4.02 (m, 2H), 3.90-3.87 (m, 2H), 3.76-3.73 (m, 6H), 3.70-3.67 (m, 3H), 3.40-3.35 (m, 1H), 2.44-2.38 (m, 2H), 2.09-2.04 (m, 2H), 2.01-1.96 (m, 3H); $^{13}$C-NMR (150 MHz, CDCl$_3$) δ 173.1, 154.4, 153.5, 132.1, 92.0, 66.9, 60.8, 60.4, 60.3, 55.9, 30.5, 24.5, 14.1; LRMS: (ESI) m/z 321 (M+Na).

6,7,8-Trimethoxy-3,4-dihydrobenzo[b]oxepin-5(211)-one. To a 50 mL round-bottom flask were added ethyl 4-(3,4,5-trimethoxyphenoxy)butanoate (460 mg, 1.7 mmol) and polyphosphoric acid (6.0 g). After stirring for 2 hours at 130° C., the reaction mixture was poured into 250 mL of ice and stirred until the polyphosphoric acid was dissolved. The reaction mixture was extracted with ethyl acetate (100 mL×3), the combined organic phase was dried over anhydrous MgSO$_4$, and concentrated under reduced pressure. The residue was purified by flash column chromatography on silica gel (Ethyl acetate/n-hexane=1:2), to afford 6,7,8-trimethoxy-3,4-dihydrobenzo[b]oxepin-5(2H)-one (188 mg, 44%). $^1$H-NMR (600 MHz, CDCl$_3$) δ 6.42 (s, 1H), 4.19 (t, 2H, J=6.0 Hz), 3.94 (s, 3H), 3.89 (s, 3H), 3.85 (s, 3H), 2.81 (t, 2H, J=6.6 Hz), 2.17-2.12 (m, 2H); $^{13}$C-NMR (150 MHz, CDCl$_3$) δ 200.3, 156.4, 156.2, 152.7, 138.7, 118.7, 100.0, 72.1, 62.4, 61.0, 56.0, 41.4, 25.9. LRMS: (ESI) m/z 253 (M+H).

(E)-4-(3-hydroxy-4-methoxybenzylidene)-6,7,8-trimethoxy-3,4-dihydrobenzo[b]oxepin-5(2H)-one (12). To a benzene solution (6.5 mL) of 6,7,8-trimethoxy-3,4-dihydrobenzo[b]oxepin-5(2H)-one (65 mg, 0.26 mmol) were added isovanillin (47 mg, 0.31 mmol) and p-toluenesulfonic acid (71 mg, 0.41 mmol). After refluxing for 1.5 hours with a Dean-Stark apparatus, the reaction mixture was cooled and quenched with saturated NaHCO$_3$. The reaction mixture was diluted with ethyl acetate (30 mL×3) and washed with water and the combined organic phases were dried over MgSO$_4$, and concentrated under reduced pressure. The residue was purified by flash column chromatography on silica gel (Ethyl acetate:n-hexane=1:2) to afford the benzylidne (12) (16 mg, 16%). $^1$H-NMR (600 MHz, CDCl$_3$) δ; 7.68 (s, 1H), 6.95-6.87 (m, 2H), 6.25 (d, 2H, J=6.0 Hz), 5.65 (s, 1H), 4.26 (t, 2H, J=6.6 Hz), 3.88-3.81 (m, 12H), 2.96 (t, 2H, J=6.6 Hz); $^{13}$C-NMR (150 MHz, CDCl$_3$) δ 192.2, 156.4, 151.9, 147.1, 145.4, 137.6, 134.2, 129.0, 121.0, 115.0, 110.6, 101.3, 71.9, 61.0, 56.0, 55.9, 26.8; LRMS (ESI) m/z 387 (M+H).

Example 7

In this Example, the method for synthesizing cremastranone analogs 13 and 14 is described, as diagrammed in FIG. 4.

(E)-ethyl 3-(3,4,5-trimethoxyphenyl)acrylate. To a CH$_2$Cl$_2$ solution (6 mL) of 3,4,5-trimethoxybenzaldehyde (1.0 g, 5.1 mmol) was added (ethoxycarbonylmethylene) triphenylphosphorane (2.1 g, 6.1 mmol) at 0° C. After stirring overnight at room temperature, the reaction mixture was concentrated under reduced pressure and the residue was purified by flash column chromatography on silica gel (Ethyl acetate/n-hexane=1:6) to afford (E)-ethyl 3-(3,4,5-trimethoxyphenyl)acrylate (460 mg, 34%). The compound was reported in the following reference, Kumar et al. *Biochemistry* 44, 15944-15952, (2005).

Ethyl 3-(3,4,5-trimethoxyphenyl)propanoate. To a methanol solution (4 mL) of (E)-Ethyl 3-(3,4,5-trimethoxyphenyl) acrylate (460 mg, 1.7 mmol) was added 10% palladium on carbon. The reaction mixture was stirred under H$_2$ atmosphere using a balloon for 24 hours and filtered through a pad of Celite. The filtrate was concentrated under reduced pressure and the residue was purified by flash column chromatography on silica gel to afford ethyl 3-(3,4,5-trimethoxyphenyl)propanoate (460 mg, 82%). $^1$H-NMR (600 MHz, CDCl$_3$) δ 6.3 (s, 1H), 4.11 (q, 2H), 3.81-3.78 (m, 9H), 2.86 (t, 2H, J=1.8 Hz), 2.58 (t, 2H, J=1.8 Hz).

5,6,7-Trimethoxy-2,3-dihydro-1H-inden-1-one. To a 25 mL round-bottom flask were added ethyl 3-(3,4,5-trimethoxyphenyl)propanoate (460 mg, 1.7 mmol) and polyphosphoric acid (5 g, 16 mmol). After heating at 150° C. for 5 hours, the reaction mixture was poured into ice and neutralized to pH 7 with saturated NaHCO$_3$ solution. The reaction mixture was extracted with ethyl acetate (50 mL×3) and the combined organic phase was dried over MgSO$_4$, and concentrated under reduced pressure. The residue was purified by flash column chromatography on silica gel (ethyl acetate/n-hexane=1:3) to afford 5,6,7-trimethoxy-2,3-dihydro-1H-inden-1-one (85 mg, 22%) as a yellow solid. $^1$H-NMR (600 MHz, CDCl$_3$) δ 6.60 (s, 1H), 3.97 (s, 3H), 3.86 (s, 3H), 3.78 (s, 3H), 2.95 (t, 2H, J=6.0 Hz), 2.59 (t, 2H, J=6.0 Hz); $^{13}$C-NMR (150 MHz, CDCl$_3$) δ 203.1, 159.6, 153.2, 151.5, 140.6, 122.9, 103.7, 61.9, 61.4, 56.2, 37.2, 25.7; LRMS (ESI) m/z 223 (M+H).

(E)-2-(3-hydroxy-4-methoxybenzylidene)-5,6,7-trimethoxy-2,3-dihydro-1H-inden-1-one (13). To a benzene solution (6.0 mL) of 5,6,7-trimethoxy-2,3-dihydro-1H-inden-1-one (40 mg, 0.2 mmol) were added isovanillin (61 mg, 0.4 mmol) and p-toluenesulfonic acid (54 mg, 0.3 mmol). After refluxing for 2.5 hours with a Dean-Stark apparatus, the reaction mixture was cooled and quenched with saturated $NaHCO_3$. The reaction mixture was diluted with ethyl acetate (30 mL×3), washed with water and the combined organic phases were dried over $MgSO_4$, then concentrated under reduced pressure. The residue was purified by flash column chromatography on silica gel (Ethyl acetate/n-hexane=2:3) to afford the (E)-2-(3-hydroxy-4-methoxybenzylidene)-5,6,7-trimethoxy-2,3-dihydro-1H-inden-1-one (13) (39 mg, 54%). $^1$H-NMR (600 MHz, $CDCl_3$) δ 7.47 (t, 1H, J=1.8 Hz), 7.26 (d, 1H, J=2.4 Hz), 7.15 (dd, 1H, J=8.4 and 1.8 Hz), 6.91 (d, 1H, J=8.4 Hz), 6.76 (s, 1H), 5.71 (d, 1H, J=2.4 Hz), 4.10 (s, 3H), 3.96 (s, 3H), 3.94 (s, 3H), 3.92 (s, 2H), 3.88 (s, 3H); $^{13}$C-NMR (150 MHz, $CDCl_3$) δ 191.0, 159.4, 152.4, 147.6, 147.5, 145.7, 141.0, 133.6, 131.9, 129.2, 124.6, 124.2, 115.3, 110.6, 103.5, 62.2, 61.5, 56.3, 56.0, 32.4; LRMS (ESI) m/z 357 (M+H).

6,7,8-Trimethoxy-3,4-dihydroisoquinolin-1(2H)-one. To a $CH_2Cl_2$ solution (1 mL) of 5,6,7-trimethoxy-2,3-dihydro-1H-inden-1-one (37 mg, 0.16 mmol) were added methanesulfonic acid (1 mL, 15 mmol) and sodium azide (25 mg, 0.38 mmol) at 0° C. After stirring for 2 hours at 0° C. and overnight at room temperature, the reaction mixture was poured into ice and extracted with $CH_2Cl_2$. The combined organic phase was dried over $MgSO_4$ and concentrated under reduced pressure. The residue was purified by flash column chromatography on silica gel (MeOH/$CH_2Cl_2$=1:15) to afford 6,7,8-trimethoxy-3,4-dihydroisoquinolin-1(2H)-one (36 mg, 90%). $^1$H-NMR (600 MHz, $CDCl_3$) δ 6.50 (s, 1H), 5.74 (s, 1H), 3.95 (s, 3H), 3.89 (s, 3H), 3.87 (s, 3H), 3.44 (dt, 2H, J=6.6 and 3.0 Hz), 2.88 (t, 2H, J=6.6 Hz); LRMS (ESI) m/z 238 (M+H).

2-(3-(Benzyloxy)-4-methoxybenzyl)-6,7,8-trimethoxy-3,4-dihydroisoquinolin-1(2H)-one (14). To a DMF solution (1 mL) of 6,7,8-trimethoxy-3,4-dihydroisoquinolin-1(2H)-one (10 mg, 0.04 mmol) was added sodium hydride (26 mg, 0.4 mmol) at 0° C. After stirring for 30 minutes at room temperature, the reaction mixture was treated with 2-(benzyloxy)-4-(bromomethyl)-1-methoxybenzene (16 mg, 0.05 mmol) at 0° C. and stirred at room temperature for 16 hours. The reaction mixture was quenched with water and extracted with $CH_2Cl_2$. The combined organic phase was dried over $MgSO_4$, and concentrated under reduced pressure. The residue was purified by column chromatography on silica gel (ethyl acetate/n-hexane=1:1) to afford the 2-(3-(benzyloxy)-4-methoxybenzyl)-6,7,8-trimethoxy-3,4-dihydroisoquinolin-1(2H)-one (14) (17 mg, 87%). $^1$H-NMR (600 MHz, $CDCl_3$) δ 7.37 (d, 2H, J=7.2 Hz), 7.18-7.16 (m, 3H), 6.87 (d,1H), 6.88-6.70 (m, 2H), 6.40 (s, 1H), 5.13 (s, 2H), 4.62 (s, 2H), 4.02 (s, 3H), 3.88 (t, 9H, J=4.2 Hz), 3.21 (t, 2H, J=6.6 Hz), 2.54 (t, 2H, J=6.6 Hz); LRMS (ESI) m/z 464 (M+H).

Example 8

In this Example, the synthesis of the biotinylated compounds (16 and 17) is described, as diagrammed in FIG. 5.

(E)-tert-butyl 2-(2-methoxy-5-((5,6,7-trimethoxy-4-oxochroman-3-ylidene)methyl)phenoxy)acetate. To an acetone solution (5 mL) of 4-benzylidenechromanone (16 mg, 0.043 mmol) were added tent-butyl bromoacetate (17 mg, 0.086 mmol) and $K_2CO_3$ (18 mg, 0.13 mmol). After refluxing for 3 hours, the reaction mixture was diluted with ethyl acetate and the combined organic phase was washed with water and brine, dried over $MgSO_4$ and concentrated under reduced pressure. The residue was purified by flash column chromatography on silica gel (Ethyl acetate/n-hexane=1:1) to afford the tert-butoxyacetate (20 mg, 95%). $^1$H-NMR (600 MHz, $CDCl_3$) δ 7.72 (s, 1H), 6.94 (d, 1H, J=8.4 Hz), 6.92 (dd, 1H, J=8.4 and 1.2 Hz), 6.75 (d, 1H, J=1.8 Hz), 6.25 (s, 1H), 5.22 (d, 2H, J=1.2 Hz), 4.59 (s, 2H), 3.98 (s, 3H), 3.92 (s, 3H), 3.88 (s, 3H), 3.83 (s, 3H), 1.48 (s, 9H); $^{13}$C-NMR (150 MHz, $CDCl_3$) δ 179.4, 167.6, 159.3, 159.2, 154.7, 150.6, 147.2, 137.8, 136.0, 127.3, 124.6, 115.5, 111.7, 110.5, 96.1, 82.5, 67.5, 66.5, 61.6, 61.3, 60.3, 56.1, 56.0, 28.0; LRMS (ESI) m/z 487 (M+H).

(E)-2-(2-methoxy-5-((5,6,7-trimethoxy-4-oxochroman-3-ylidene)methyl)phenoxy)acetic acid (A in FIG. 5). To a $CH_2Cl_2$ solution (2 mL) of the tert-butoxyacetate (11 mg, 0.023 mmol) was added TFA. After stirring for 2.5 hours at room temperature, the reaction mixture was concentrated under reduced pressure. The residue was purified by flash column chromatography on silica gel (MeOH/$CH_2Cl_2$=1:10) to afford the aryloxyacetic acid (A) (7 mg, 70%). $^1$H-NMR (600 MHz, $CD_3OD$) δ 7.65 (s, 1H), 7.08 (d, 1H, J=6.6 Hz), 6.97 (m, 1H), 6.91 (s, 1H), 6.37 (d, 1H, J=1.8 Hz), 5.22 (s, 2H), 4.57 (s, 2H), 3.92 (s, 3H), 3.89 (s, 3H), 3.87 (s, 3H), 3.76 (s, 3H); LRMS (ESI) m/z 429 (M−H).

(4-hydroxyphenyl)(4-(prop-2-yn-1-yloxy)phenyl)methanone. To an acetone solution (5.0 mL) of 4,4'-dihydroxybenzophenone (512 mg, 2.4 mmol) were added propargyl bromide (0.21 mL, 2.4 mmol) and $K_2CO_3$ (495 mg, 3.6 mmol). After refluxing for 5 hours, the reaction mixture was diluted with ethyl acetate and the combined organic phase was washed with water and brine, dried over $MgSO_4$ and concentrated under reduced pressure. The residue was purified by flash column chromatography on silica gel (Ethyl acetate/n-hexane=1:2) to afford the propargylated benzophenone (197 mg, 33%).

tert-butyl (3-(4-(4-(prop-2-yn-1-yloxy)benzoyl)phenoxy)propyl)carbamate (B in FIG. 5). To a THF solution (2 mL) of N-Boc 3-aminopropanol (117 mg, 0.76 mmol) were added the propargylated benzophenone (140 mg, 0.56 mmol), $PPh_3$ (150 mg, 0.76 mmol), and DIAD (130 μL, 0.56 mmol) at room temperature. After stirring for 3 hours at room temperature, the reaction mixture was diluted with ethyl acetate and the combined organic phase was washed with water and brine, dried over $MgSO_4$ and concentrated under reduced pressure. The residue was purified by flash column chromatography on silica gel (Ethyl acetate/n-hexane=1:3) to afford the dialkylated dihydroxybenzophenone (B) (160 mg, 70%). $^1$H-NMR (600 MHz, $CDCl_3$) δ 7.77 (dd, 4H, J=9.0 and 5.0 Hz), 7.03 (d, 2H, J=9.0 Hz), 6.93 (d, 2H, J=9.0 Hz), 4.82 (bs, 1H), 4.75 (d, 2H, J=1.2 Hz), 4.09 (t, 2H, J=6.0 Hz), 3.33 (m, 2H), 2.56 (t, 1H, J=2.4 Hz), 2.01 (m, 1H), 1.42 (s, 9H), 1.25 (m, 1H); $^{13}$C-NMR (150 MHz, $CDCl_3$) δ 194.3, 162.1, 160.6, 156.0, 132.2, 132.1, 131.5, 130.6, 114.3, 113.9, 77.8, 76.1, 65.9, 55.8, 37.8, 29.5, 28.4, 14.2; LRMS (ESI) m/z 432 (M+H).

N-(2-(2-(2-(2-azidoethoxy)ethoxy)ethoxy)ethyl)-5-((3aS,4S,6aR)-2-oxohexahydro-1H-thieno[3,4-d]imidazol-4-yO-pentanamide. To a THF solution (1 mL) of Biotin-ONp (50 mg, 0.14 mmol) were added 11-azido-3,6,9-trioxaundecan-1-amine (27 μL, 0.14 mmol) and $Et_3N$ (57 μL, 0.41 mmol) at room temperature. After stirring for 12 hours at room temperature, the reaction mixture was quenched with $H_2O$ (1 mL). The reaction mixture was extracted three times with ethyl acetate and the combined organic phase was washed with brine, dried over $MgSO_4$, concentrated under reduced pressure. The residue was purified by flash column chromatography on silica gel (MeOH/CH$_2$Cl$_2$=1:10) to afford the azide (30 mg, 49%) $^1$H-NMR (600 MHz, CDCl$_3$) δ 6.83 (m, 1H), 6.73 (m, 1H), 5.78 (m, 1H), 4.50 (m, 1H), 4.30 (m,1H), 3.65 (m, 8H), 3.62 (m, 2H), 3.56 (m, 2H), 3.42-3.37 (m, 4H), 3.13 (m, 1H), 2.90 (m, 1H), 2.74 (d, 1H, J=13 Hz), 2.22 (t, 2H, J=7.8 Hz), 1.75-1.62 (m, 4H), 1.44-1.41 (m, 2H); LRMS (ESI) m/z 467 (M+H).

Boc-protected Benzophenone-Biotin. To a t-BuOH/H$_2$O solution (2 mL, 1:1) of the benzophenone (B) (35 mg, 0.086 mmol) and the PEG-Biotin (38 mg, 0.086 mmol) were added CuSO$_4$.5H$_2$O (2 mg, 0.086 mmol) and sodium ascorbate (1.0 M in H$_2$O, 2 drops) at room temperature. After stirring at room temperature for 24 hours, the reaction mixture was diluted with H$_2$O (1 mL) and extracted with ethyl acetate and the combined organic phase was washed with brine, dried over MgSO$_4$, and concentrated under reduced pressure. The residue was purified by flash column chromatography on silica gel (MeOH/CH$_2$Cl$_2$=1:10) to afford the 1,2,3-triazole (30 mg, 40%) $^1$H-NMR (600 MHz, CDCl$_3$) δ 7.86 (s, 1H), 7.77 (dd, 4H, J=8.4 and 2.4 Hz), 7.06 (d, 2H, J=9.0 Hz), 6.94 (d, 2H, J=8.4 Hz), 6.67 (bs, 1H), 6.45 (bs, 1H), 5.49 (bs, 1H), 5.28 (s, 2H), 4.82 (bs, 1H), 4.57 (t, 2H, J=4.8 Hz), 4.47 (m, 1H), 4.28 (m, 1H), 4.10 (t, 2H, J=6.0 Hz), 3.89 (t, 2H, J=4.8 Hz), 3.65 (m, 2H), 3.60 (m, 2H), 3.56 (m, 6H), 3.52 (t, 2H, J=4.8 Hz), 3.41-3.33 (m, 4H), 3.12 (m, 1H), 2.88 (m, 1H), 2.73 (m, 1H), 2.19 (t, 2H, J=7.2 Hz), 2.03 (m, 2H), 1.75-1.58 (m, 6H), 1.43 (s, 9H), 1.41 (m, 2H); $^{13}$C-NMR (150 MHz, CDCl$_3$) δ 194.4, 173.2, 162.1, 161.4, 156.0, 143.2, 132.2, 132.2, 131.2, 130.5, 124.3, 114.3, 113.9, 70.67, 70.51, 70.48, 70.37, 70.34, 70.11, 70.04, 69.92, 69.39, 65.95, 62.05, 61.75, 60.15, 55.54, 50.67, 50.38, 40.53, 39.11, 37.83, 29.51, 28.42, 28.18, 28.09, 25.58; LRMS (ESI) m/z 854 (M+H).

Ammonium salt of Benzophenone-Biotin (17). To a CH$_2$Cl$_2$ solution (2 mL) of the Boc-protected benzophenone-biotin (20 mg, 0.028 mmol) was added TFA (0.4 mL) at 0° C. After stirring for 2.5 hours at room temperature, the reaction mixture was concentrated under reduced pressure to afford the crude ammonium trifluoroacetate (17) (16 mg, 72%). The crude ammonium salt was used for the next reaction without further purification. $^1$H-NMR (600 MHz, CD$_3$OD) δ 8.17 (s, 1H), 7.77 (d, 4H, J=8.4 Hz), 7.16 (d, 2H, J=8.4 Hz), 7.08 (d, 2H, J=8.4 Hz), 5.28 (s, 2H), 4.62 (m, 4H), 4.23 (t, 2H, J=6.0 Hz), 3.91 (t, 2H, J=5.0 Hz), 3.65 (m, 2H), 3.59-3.55 (m, 8H), 3.48 (m, 2H), 3.18 (t, 2H, J=7.2 Hz), 3.12-3.01 (m, 2H), 2.20 (m, 4H), 1.89 (m, 2H), 1.66 (m, 4H); LRMS (ESI) m/z 776 (M+Na).

Cremastranone analog-Benzophenone-Biotin (16). To a DMF solution (1 mL) of the carboxylic acid (A) (6.9 mg, 0.016 mmol) were added HBTU (10 mg, 0.026 mmol) and DIPEA (10 μL, 0.057 mmol). After stirring for 30 minutes, a DMF solution (0.5 mL) of the ammonium salt (17) (12 mg, 0.016 mmol) was added to the reaction mixture. After stirring for 24 hours, the reaction mixture was diluted with ethyl acetate, dried over MgSO$_4$ and concentrated under reduced pressure. The residue was purified by flash column chromatography on silica gel (MeOH/CH$_2$Cl$_2$=1:10) to afford the cremastranone-benzophenone-biotin (16) (5.6 mg, 30%). $^1$H-NMR (600 MHz, CDCl$_3$) δ 8.01 (s, 1H), 7.91 (s, 1H), 7.76-7.73 (m, 5H), 7.71 (s, 1H), 7.23 (m, 1H), 7.07 (d, 2H, J=9 Hz), 6.96-6.92 (m, 4H), 6.84 (s, 1H), 6.44 (bs, 1H), 6.25 (s, 1H), 5.60 (bs, 1H), 5.29 (s, 2H), 5.28 (s, 2H), 5.20 (d, 2H, J=1.8 Hz), 4.86 (bs, 1H), 4.60 (t, 2H, J=4.8 Hz), 4.56 (s, 2H), 4.12-4.10 (m, 2H), 3.97 (s,3H), 3.91 (t, 2H, J=4.8 Hz), 3.88 (s, 3H), 3.87 (s, 3H), 3.83 (s, 3H), 3.72-3.67 (m, 8H), 3.54 (m, 2H), 3.17 (m, 6H), 2.95 (s, 2H), 2.88 (s, 2H), 2.20 (m, 2H), 2.11 (m, 2H), 1.48 (m,8H); LRMS (ESI) m/z 1189 (M+Na).

Example 9

In this Example, the effect of synthetic cremastranone (1) and SH-11052 (2) prepared in Examples 1 and 2 on the proliferation of human umbilical vascular endothelial cells (HUVECs) and human retinal microvascular endothelial cells (HRECs) was analyzed.

It has been reported that compound 1 isolated from C. appendiculata showed anti-proliferative effects with a 50% growth inhibitory (GI$_{50}$) concentration value in the low micromolar range in a HUVEC proliferation assay. In order to test if synthetic cremastranone (1) and SH-11052 (2) has similar effects, the proliferation of HUVECs induced by complete medium was monitored in the presence of synthetic cremastranone (1) and SH-11052 (2) in the concentration range of 0.5 nM to 500 μM.

Particularly, in a 96-well clear bottom black plate, cells (2,500 cells per well) were seeded in a total volume of 100 μL, EGM-2. After 24 hours of incubation of the plate at 37° C. and 5% CO$_2$, a DMSO solution of synthetic cremastranone (1) or SH-11052 (2) was added in the concentration range of 0.5 nM to 500 μM (final DMSO concentration=1%). The plate was then further incubated for 48 hours before adding 11.1 μL of ALAMARBLUE® reagent to each well. Four hours after the addition of ALAMARBLUE®, fluorescence readings with excitation and emission wavelengths of 560 nm and 590 nm, respectively, were taken and the data were analyzed in GraphPad Prism software (v. 6.0). Dose response curves were generated and the GI$_{50}$ values were calculated using the following equation:

$$Y=100/(1+10\textasciicircum(X-\text{LogGI}_{50})).$$

As shown in FIGS. 6A-6D, both synthetic cremastranone (1) and SH-11052 (2) demonstrated in vitro anti-proliferative activity in both HUVECs and the more disease-relevant HRECs.

In order to confirm the inhibition of cell proliferation, incorporation of 5-ethynyl-2'-deoxyuridine (EdU) into endothelial cells in the presence of SH-11052 (2) was further monitored. Particularly, cells (25,000 per coverslip) were seeded onto coverslips coated with Attachment Factor (Cell Systems, Kirkland, Wash., USA) placed in a 6-well plate and incubated with the indicated concentrations of SH-11052 (2) in EGM-2 for 24 hours at 37° C. and 5% CO$_2$. The cells were then serum starved for 8 hours and the medium was replaced with EGM-2 containing 10 μM EdU. The plate was further incubated for another 8 hours before processing the cells for detection of labeled DNA (according to the manufacturer's instructions for the Click-iT EdU assay kit). Images were taken using an EVOS fluorescence microscope (AMG, Mill Creek, Wash., USA) and the number of DAPI stained and EdU stained cells were counted in six randomly chosen fields using ImageJ software. DNA synthesis in both HRECs and HUVECs was significantly inhibited in a dose dependent manner by SH-11052 (2) (FIGS. 7A-7D).

Example 10

In this Example, the effect of SH-11052 (2) prepared in Example 2 on the angiogenic ability of human retinal microvascular endothelial cells (HRECs) was evaluated.

Matrigel assays were performed as described in Ponce (2001) In vitro matrigel angiogenesis assays, Methods Mol Med 46: 205-209, with slight modifications for the use of HRECs. Briefly, HRECs were starved overnight at 0.5% FBS in EBM-2 and plated on a 96-well plate at a density of 7,500 cells/well over 50 µL of Matrigel high concentration basement membrane. SH-11052 (2) was added at the indicated concentrations in EBM-2+1% FBS. Cells were observed every 2 hours by bright field microscopy at 40× magnification for tube formation. Closed units (polygons) were manually counted at 8 hours post plating and numbers normalized to the DMSO control. Assays were performed in triplicate.

Figure 8A:
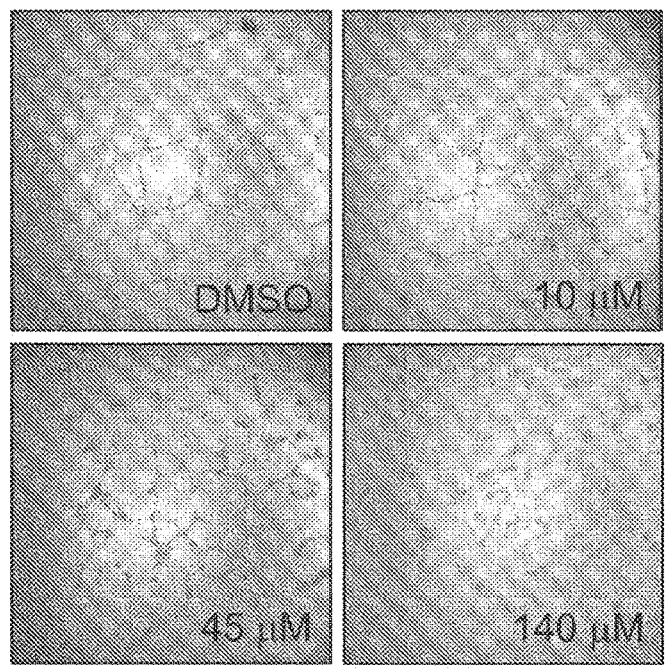
Figure 8B:
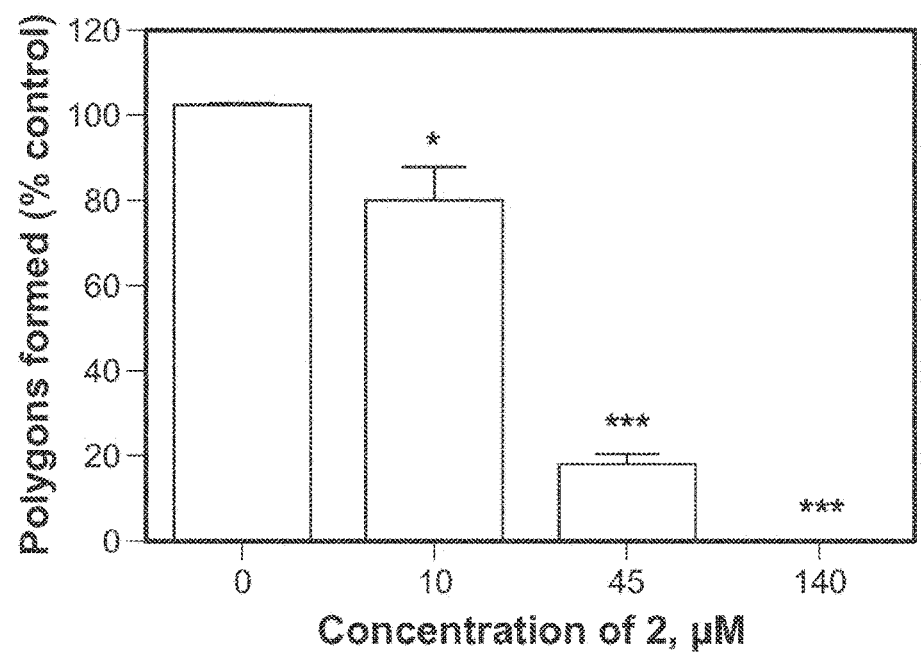

HRECs treated with SH-11052 (2) showed a significant reduction in their tube formation ability as compared to DMSO treated samples (FIG. 8A). In the presence of SH-11052 (2) at the $GI_{50}$ value, there was a significant reduction in tube formation and the network of tubes was disrupted (polygon spaces in FIG. 8A) and at 140 µM the tube formation ability was completely abolished (FIG. 8B).

Further, cells (25,000 per coverslip) were seeded onto coverslips coated with Attachment Factor (Cell Systems, Kirkland, Wash., USA) and incubated at 37° C. and 5% $CO_2$ in EGM-2 until ~80% confluence was achieved. The cells were then incubated for 4 hours with the indicated concentrations of SH-11052 (2). Staurosporine (SP; 1 µM) was used as a positive control. After the incubation, the cells were fixed in 4% paraformaldehyde for 20 minutes at room temperature followed by three quick washes in Tris buffered saline pH 7.4 (TBS). The cells were permeabilized by incubating with 0.5% Triton X-100 for 10 minutes and then blocked in 10% block solution (DAKO, Glostrup, Denmark) in TBS plus 1% bovine serum albumin (BSA) for 1 hour. The cells were then incubated with cleaved caspase-3 (D175) antibody (1:200 dilution) overnight at 4° C. Dylight 555 conjugated goat anti-rabbit secondary antibody (1:400) was used to probe the cleaved caspase-3 antibody. The coverslips were mounted using Vectashield mounting medium containing DAPI (Vector Labs, Burlingame, Calif., USA) for nuclear staining. The cells were imaged using an LSM 700 confocal microscope (Zeiss, Thornwood, N.Y., USA).

Figure 8C:
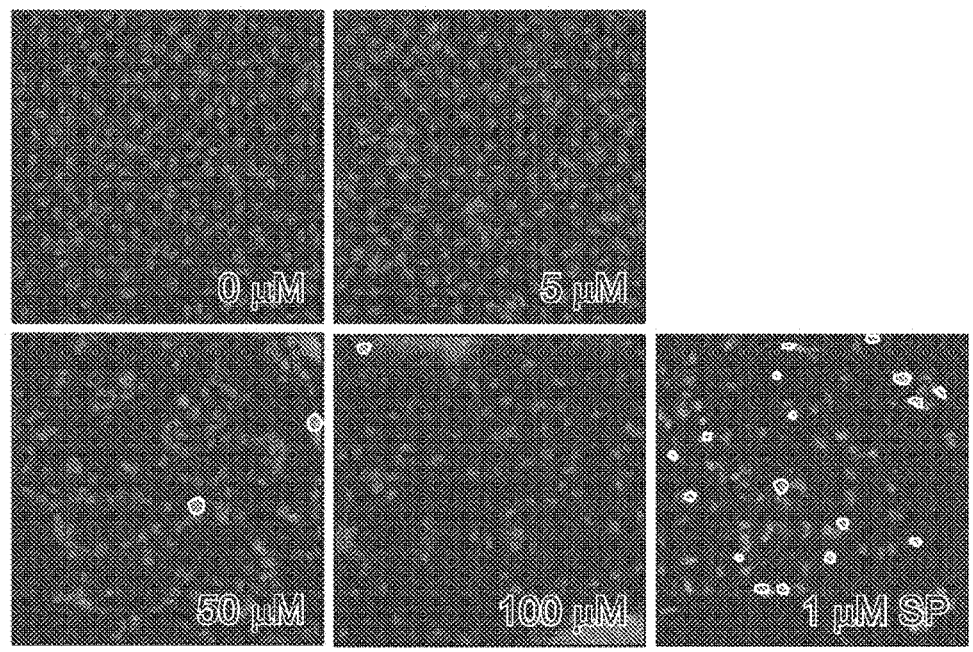
Figure 8D:
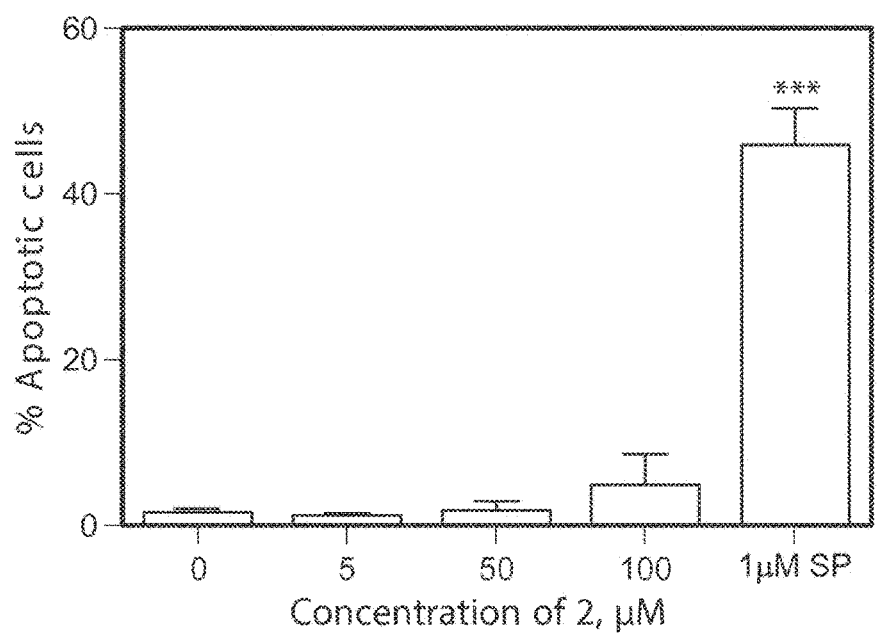

As shown in FIGS. 8C & 8D, even at 100 µM, SH-11052 (2) caused negligible apoptosis of HRECs as determined by cleaved caspase-3 staining Example 11

After establishing the anti-angiogenic activity of SH-11052 (2), the mechanistic details of its activity in HRECs were analyzed. Particularly, as inflammation plays a crucial role in pathological angiogenesis, in this Example, the effect of SH-11052 (2) on inflammatory signaling in endothelial cells was analyzed.

Cells (25,000 per coverslip) were seeded onto coverslips coated with Attachment Factor (Cell Systems, Kirkland, Wash., USA) and incubated at 37° C. and 5% $CO_2$ for 24 hours in EGM-2. The cells were starved in 0.1% serum-EBM-2 for 8 hours followed by 0.1% serum-EBM-2 medium for one hour in the presence of different concentrations of SH-11052 (2). The cells were induced with 10 ng/ml TNF-α, a known pro-inflammatory cytokine and inducer of NF-κB, for 20 minutes and fixed with 4% paraformaldehyde solution for 20 minutes at room temperature. Since NF-κB exerts its transcriptional activity in the nucleus, blockade of stimulus-induced nuclear translocation of NF-κB is an indication of NF-κB pathway inhibition.

Cells were quickly washed three times in TBS and permeabilized by incubating with 0.5% Triton X-100 for 10 minutes. The cells were blocked in 10% block solution (DAKO) in TBS plus 1% BSA followed by incubation with an antibody against NF-κB p65 (1:50 dilution). Dylight 488-conjugated goat anti-mouse secondary antibody (1:200 dilution) was used to probe the NF-κB p65 antibody. The coverslips were mounted using Vectashield mounting medium containing DAPI (Vector Labs) for nuclear staining. The cells were imaged using an LSM 700 confocal microscope (Zeiss).

HRECs were seeded at $10^5$ cells/well in a 6-well plate and after 24 hours of incubation at 37° C., cells were serum starved in 0.1% serum-EBM-2 for 8 hours. Cells were then treated with the indicated concentrations of SH-11052 (2) for one hour before the addition of 20 ng/ml of TNF-α. After 20 minutes, cells were lysed in NP-40 Lysis buffer containing 25 mM HEPES pH 7.4, 1% NP-40, 150 mM NaCl, 10% glycerol, 1 mM sodium orthovanadate, 10 mM sodium fluoride, 1 mM sodium pyrophosphate, 1 mM PMSF, 2.5 mg/ml aprotinin, 1 mM pepstatin, and 1 mM leupeptin. Equal amounts of proteins (80 µg), as measured by a Bradford assay, were run on 10% SDS-PAGE, transferred to PVDF membrane, blocked with 5% BSA in TBS-0.05% Tween-20 and immunoblotted with the indicated primary antibodies (1:1000 in 1% BSA in TBS-0.05% Tween-20) overnight at 4° C. After three washes in TBS-0.05% Tween-20, HRP-conjugated secondary antibodies (1:5000 in 5% BSA in TBS-0.05% Tween-20) were applied for one hour at room temperature. After three washes, the protein bands were detected and densitized using ECL Prime western blot detection reagent (GE Life Sciences, Piscataway, N.J., USA) and an XRS gel documentation system running Quantity One software (Bio-Rad). Target protein band intensity was normalized to housekeeping gene a-tubulin. For phosphoprotein analysis, normalized signal of each phosphoprotein was expressed relative to the normalized total amount of that protein.

Figure 9A:
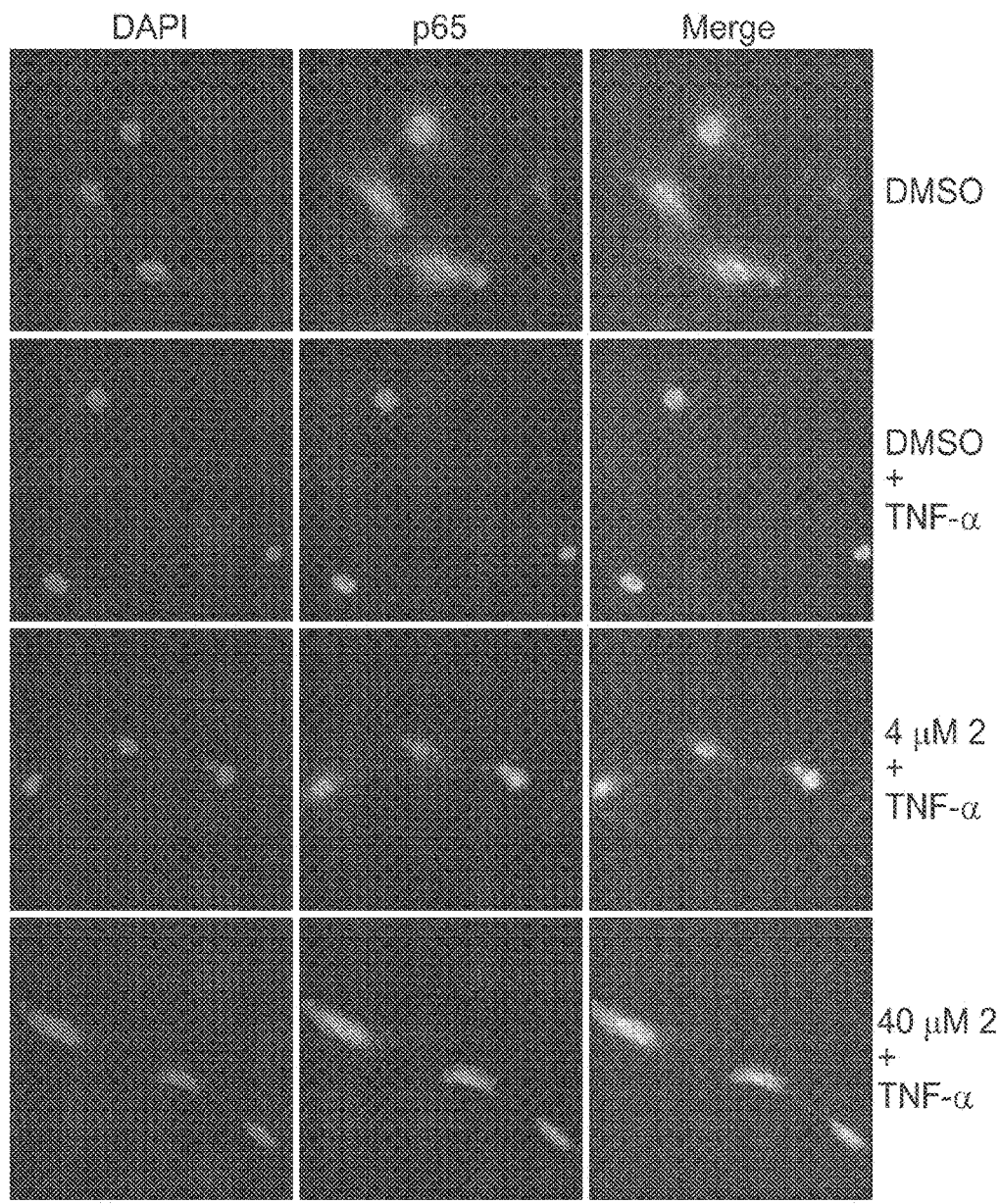
Figure 9B:
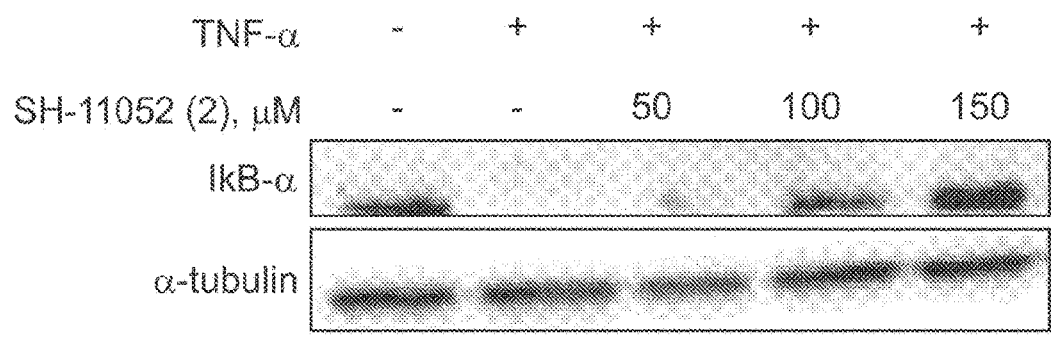
Figure 9C:
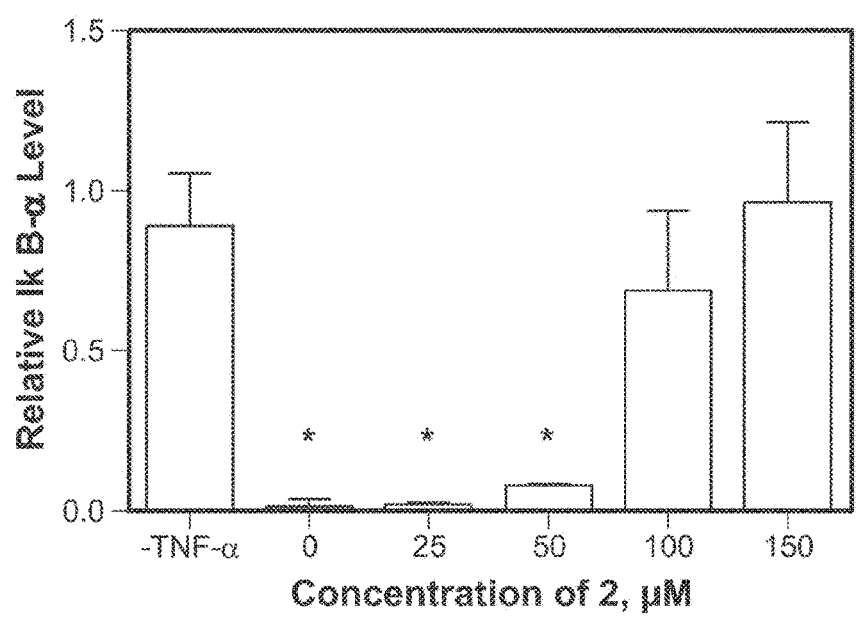

The nuclear translocation of NF-κB upon TNF-α stimulation was inhibited by SH-11052 (2) in a dose dependent manner as monitored by immunofluorescence (FIG. 9A). IκB-α is an inhibitory protein that binds to NF-κB and prevents its nuclear translocation. Upon TNF-α stimulation, IκB-α is phosphorylated and degraded, freeing NF-κB for nuclear translocation. In the presence of SH-11052 (2), the TNF-α-mediated degradation of IκB-α was significantly decreased in a dose dependent manner, further indicating that SH-11052 (2) was inhibiting NF-κB signaling (FIGS. 9B & 9C).

Figure 9D:
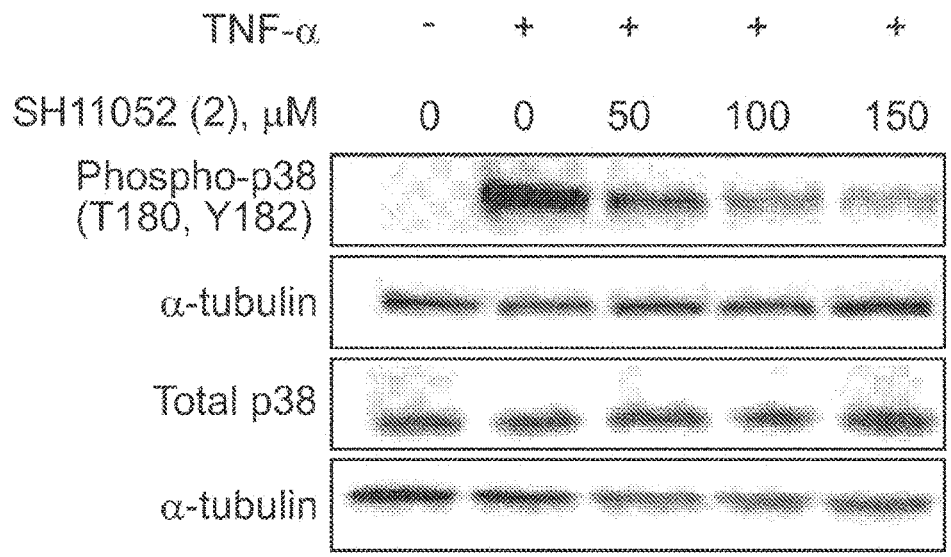
Figure 9E:
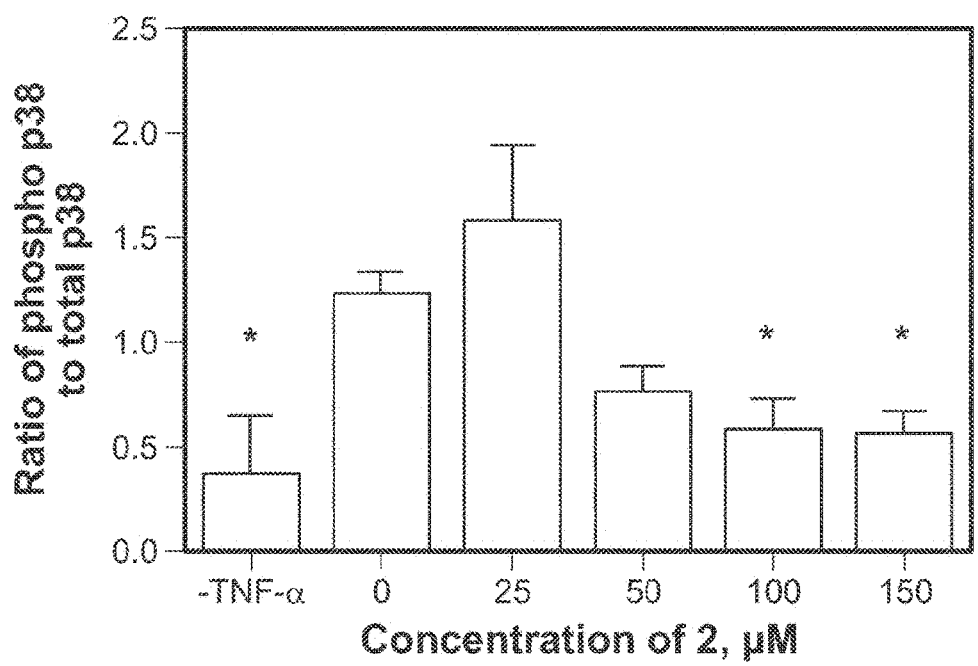

In order to confirm inhibition of the TNF-α pathway, the activating phosphorylation of p38 mitogen activated protein kinase (MAPK), an important downstream target of the TNF-α pathway involved in cytokine induced cell proliferation, was monitored. SH-11052 (2) inhibited phosphorylation of p38 MAPK in a dose dependent manner (FIG. 9D & 9E).

Example 12

In this Example, the expression of NF-κB induced genes in the presence of SH-11052 (2) was analyzed.

Cells (25,000 per coverslip) were seeded onto coverslips coated with Attachment Factor (Cell Systems, Kirkland, Wash., USA) and incubated at 37° C. and 5% $CO_2$ for 24 hours in EGM-2. The cells were starved in 0.1% serum-EBM-2 for 8 hours followed by incubation in 0.1% serum-EBM-2 medium for an hour in the presence of different concentrations of SH-11052 (2). The cells were challenged with 10 ng/ml of TNF-α for 24 hours and fixed with 4% paraformaldehyde solution for 20 minutes at room temperature. The coverslips were quickly washed three times in TBS and blocked using 10% block solution (DAKO) prepared in 1× TBS-1% BSA buffer. The coverslips were incubated with the antibody against VCAM-1 (1:100 dilution), a cell adhesion molecule specifically expressed on endothelial cells, whose expression is induced by NF-κB upon TNF-α signaling, for 16 hours at 4° C. followed by three washes in TBS-0.1% BSA buffer. Dylight 555-conjugated secondary antibody (1:200) was used to probe for the VCAM-1 antibody. After three washes in TBS-0.1% BSA, the coverslips were mounted using Vectashield mounting medium containing DAPI nuclear stain. The cells were imaged using an LSM 700 confocal microscope. The image was analyzed for fluorescence signal intensity using MetaMorph software (Molecular Devices, Sunnyvale, Calif., USA).

There was a significant dose-dependent decrease in VCAM-1 protein expression in the presence of SH-11052 (2) (FIGS. 10A & 10B).

Similarly, the mRNA expression of the pro-inflammatory molecules IL8, PTGS2 (COX2) and CCL2 (MCP-1), inducible by NF-KB, were analyzed in the presence of SH-11052 (2). Cells ($10^5$ per well) were seeded in a 6-well plate and incubated for 24 hours at 37° C. and 5% $CO_2$. The cells were then starved in 0.1% serum-EBM-2 for 12 hours followed by incubation for an hour in the presence of different concentrations of SH-11052 (2). The cells were then challenged for 24 hours with 10 ng/ml TNF-α. Following incubation, cells were lysed and RNA was isolated using Trizol reagent (Life Technologies). cDNA was prepared from 80 ng total RNA using random primers and M-MuLV Reverse Transcriptase (New England Biolabs, Ipswich, Mass., USA). RT-PCR reactions were set up using the TaqMan Fast Gene Expression Assay Kit according to the manufacturer's instructions. FAM-labeled TaqMan probes for PTGS2 (Hs00153133_m1), CCL2 (Hs00234140_m1), IL8 (Hs00174103_m1), and control, TBP (Hs99999910_m1), genes were used to monitor the expression levels of these genes. The qRT-PCR plate was read in a ViiATM 7 qPCR system (Life Technologies) and the data were analyzed using the $\Delta\Delta C_t$ method. The expression levels of genes were normalized to TBP gene expression and calibrated to the DMSO-treated, unstimulated sample. SH-11052 (2) decreased the expression of these pro-inflammatory molecules (FIG. 10C).

Example 13

In this Example, the effect of SH-11052 (2) on VEGF signaling was monitored.

HRECs were seeded at $10^5$ cells/well in a 6-well plate and after 24 hours of incubation at 37° C., cells were serum starved in 0.1% serum-EBM-2 for 8 hours. Cells were then treated with the indicated concentrations of SH-11052 (2) for one hour before the addition of 100 ng/ml VEGF. After 20 minutes, cells were lysed in NP-40 Lysis buffer containing 25 mM HEPES pH 7.4, 1% NP-40, 150 mM NaCl, 10% glycerol, 1 mM sodium orthovanadate, 10 mM sodium fluoride, 1 mM sodium pyrophosphate, 1 mM PMSF, 2.5 mg/ml aprotinin, 1 mM pepstatin, and 1 mM leupeptin. Equal amounts of proteins (80 μg), as measured by a Bradford assay, were run on 10% SDS-PAGE, transferred to PVDF membrane, blocked with 5% BSA in TBS-0.05% Tween-20 and immunoblotted with the indicated primary antibodies (1:1000 in 1% BSA in TBS-0.05% Tween-20) overnight at 4° C. After three washes in TBS-0.05% Tween-20, HRP-conjugated secondary antibodies (1:5000 in 5% BSA in TBS-0.05% Tween-20) were applied for one hour at room temperature. After three washes, the protein bands were detected and densitized using ECL Prime western blot detection reagent (GE Life Sciences, Piscataway, NJ, USA) and an XRS gel documentation system running Quantity One software (Bio-Rad). Target protein band intensity was normalized to housekeeping gene a-tubulin. For phosphoprotein analysis, normalized signal of each phosphoprotein was expressed relative to the normalized total amount of that protein.

As VEGF signaling is a major contributor to angiogenesis, the ability of SH-11052 (2) to inhibit VEGF signaling along with inflammation induced TNF-α signaling was analyzed. Upon VEGF stimulation, VEGF receptor 2 (VEGFR2) autophosphorylates, leading to activation of the PI3K/Akt pathway. SH-11052 (2) did not inhibit phosphorylation of VEGFR2, but inhibited activation of the downstream Akt in HRECs (FIGS. 11A-11D). Since TNF-a signaling also feeds through Akt to IKKα, these results suggest that SH-11052 (2) might act at the level of PI3K or Akt to block both VEGF and TNF-α signaling.

Example 14

In this Example, a novel photoaffinity reagent, cremastranone analog compounds 16 and 17, as prepared in Example 8, was used in a pull-down assay to seek cremastranone target proteins.

Approximately $10^8$ cells were lysed in isotonic buffer (25 mM Tris-Cl pH 7.4, 150 mM NaCl) by dounce homogenization (~50 times). The lysate was centrifuged at 2000×g for 2 minutes. The pellet and supernatant were separated and the pellet (nuclear fraction) was resuspended in lysis buffer (25 mM Tris-Cl pH 7.4, 150 mM NaCl, 1% Triton X-100) and homogenized. The supernatant was centrifuged at 100,000×g for 45 minutes and the resultant pellet P100 and supernatant S100 were collected. P100, S100 and the nuclear fractions were mixed with neutravidin beads conjugated either to analog compounds 16 or 17 (FIG. 12) and incubated at 4° C. for 1 hour followed by irradiation with UV light for 30 minutes at 4° C. The beads were then extensively washed with lysis buffer and the beads were heated to 90° C. in SDS-PAGE loading dye to elute the bound proteins. The eluted proteins were separated by SDS-PAGE and detected by the silver-staining technique. As shown in FIG. 13, a candidate, specific 50 kDa band (arrow) was evident (* indicates non-specific bands).

Example 15

In this Example, synthetic analogs of cremastranone synthesized as in Examples 2-7 were tested in ALAMARBLUE® proliferation assays in HUVECs, HRECs, retinoblastoma and uveal melanoma cell lines (to seek non-specific ocular cytotoxins) and the effect on tube formation of compound SH-11037 (6c) was analyzed.

For proliferation assays, cells (2500 per well) were seeded in a 96-well clear bottom black polystyrene plate in a total volume of 100 μL. HUVECs and HRECs were grown in EGM-2 and CSC+ media respectively, while 92-1 and Y79 cells were maintained in RPMI+10% FBS, penicillin/streptomycin and RB medium (IMDM+10% FBS+ penicillin/streptomycin+10 μg/mL insulin+55 μM β-mercaptoethanol) respectively. After 24 hours of incubation of the plate at 37° C., the compounds were dissolved in DMSO and added in the concentration range of 500 μM to 0.5 nM. The plate was then incubated at 37° C. and 5% $CO_2$ conditions for 48 hours before adding 11.1 µL of alamar blue reagent for each well. Four hours after the addition of ALAMARBLUE® reagent, fluorescence readings with excitation and emission wavelengths of 560 nm and 590 nm respectively were taken and the data was analyzed in GraphPad Prism software. The dose response curves were generated and the $GI_{50}$ values were calculated using the equation:

$$Y=100/(1+10^{(X-LogGI_{50})}) \quad \text{(Table 1)}.$$

For determining the effect of analog compound SH-11037 (6c) on tube formation, HRECs were plated in 100 µL of EGM-2 containing SH-11037 (6c) (0 nM, 50 nM and 200 nM) dissolved in DMSO in 96-well MatriGel-coated plates for one hour. Wells were photographed after 8 hours and number of polygons (enclosed shapes bordered by tubes) manually counted and expressed as a percentage of the DMSO-only control.

To analyze the effect of SH-11037 (6c) on NF-κB signaling, cells (25,000 per coverslip) were seeded onto coverslips and incubated at 37° C. for 24 hours in EGM-2 medium. Then the cells were starved in 0.1% serum-EBM-2 medium for 8 hours followed by complete EGM-2 media for one hour in the presence of 50 µM and 200 µM of SH-11037 (6c). The cells were induced with 10 ng/ml of TNF-α for 20 minutes and fixed with 4% paraformaldehyde solution for 20 minutes at room temperature. Cells were quickly washed three times in 1× Tris buffered saline pH 7.4 (TBS) and were permeabilized by incubating with 0.5% Triton X-100 for 10 minutes. The cells were blocked in 10% DAKO block solution in TBS plus 1% BSA followed by incubation with an antibody against NF-κB p65 (1:50 dilution). Dylight 488-conjugated goat anti-mouse secondary antibody (1:200 dilution) was used to probe the NF-κB p65 antibody. The coverslips were mounted using Vectashield mounting media containing DAPI for nuclear staining. The cells were imaged using an LSM 700 confocal microscope from Carl Zeiss. Cells were stained with DAPI to visualize nuclei.

As shown in FIG. 14, SH-11037 (6c) blocked growth with HREC $GI_{50}$=150 nM and HUVEC $GI_{50}$=1 µM (not shown). Further, treatment with 500 nM SH-11037 (6c) profoundly (88%) blocked HREC tube formation (FIGS. 15A-15B), but was non-toxic to a uveal melanoma cell line and only toxic at $GI_{50}$=12 µM to a retinoblastoma cell line (Table 1), suggesting a specific antiproliferative effect on endothelial cells. Although SH-11037 (6c) blocked migration of HRECs, SH-11037 (6c) did not promote apoptosis of these cells (FIGS. 16A-16B). Further, surprisingly, SH-11037 (6c) did not share cremastranone's gene expression effects on p21, CDK1, IL-6 and IL-8 (data not shown), nor did it block p65 translocation at effective concentrations (FIG. 17). These results indicated that SH-11037 (6c) and other molecules, such as 11k, provide novel anti-angiogenic compounds for treatment of ocular and other neovascular disorders.

Example 16

In this Example, the effect of SH-11037 (6c) to block oxygen-induced retinopathy (OIR) in vivo was analyzed.

Particularly, neonatal C57BL/6 mice (n=3-4 pups per group) were exposed to 75% oxygen from postnatal day 7 (P7) until P12 and brought to room air to cause ischemia and extensive neovessel formation at P17. The hyperoxia obliterates the normal retinal vasculature, prompting aberrant overgrowth including intravitreal vascular tufts, once returned to normoxia. Further, mice were injected with PBS alone (vehicle) or PBS containing SH-11037 (6c) to give the estimated intravitreal concentrations of 1.0 µM using a 33G needle, under isoflurane anesthesia at the time of return to room air on P12. At P17, the mice were euthanized, eyes fixed, and retinal wholemounts were prepared.

Wholemounts were stained with AlexaFluor488-isolectin B4 and imaged on a Zeiss LSM700 confocal microscope. Neovascular area, as a percentage of total retinal area, was calculated using ImageJ with the SWIFT_NV plugin. Results are shown in FIGS. 18A & 18B. As shown, a single intravitreal dose of 1 µM SH-11037 (6c) significantly decreased neovascular area in the OIR mouse model.

TABLE 1

Anti-proliferative effects of synthetic cremastranone analogs on HRECs, HUVECs, Y-79 retinoblastoma cells and 92-1 uveal melanoma cells. 50% growth inhibitory ($GI_{50}$) concentrations are given in µM.

| Compound No. | Structure | GI50 HUVEC | GI50 HREC | GI50 Y-79 | GI50 92-1 |
|---|---|---|---|---|---|
| 1 (cremastranone) | | 0.377 | 0.217 | 47 | 9.8 |
| 2 (SH-11052) | | 18 | 43 | 87 | 6 |
| 3a | | 94 | >100 | >100 | >100 |
| 3b | 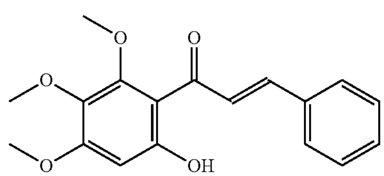 [SMILES: COc1cc(O)c(C(=O)/C=C/c2ccccc2)c(OC)c1OC] | >100 | >100 | >100 | >100 |
| 4a | 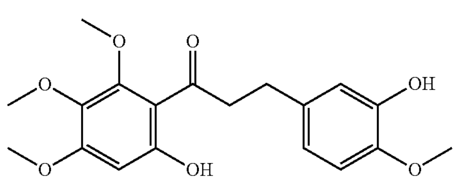 | 102 | 68 | 68 | >100 |

TABLE 1-continued

Anti-proliferative effects of synthetic cremastranone analogs on HRECs, HUVECs, Y-79 retinoblastoma cells and 92-1 uveal melanoma cells. 50% growth inhibitory (GI$_{50}$) concentrations are given in μM.

| Compound No. | Structure | GI50 HUVEC | GI50 HREC | GI50 Y-79 | GI50 92-1 |
|---|---|---|---|---|---|
| 4b | 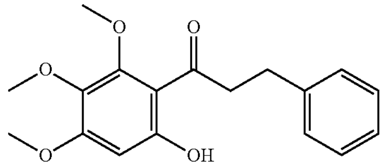 [SMILES: COc1cc(O)c(C(=O)CCc2ccccc2)c(OC)c1OC] | 104 | >100 | >100 | >100 |
| 4c | 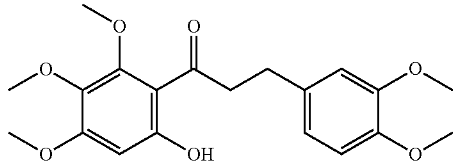 | 74 | 123 | >100 | >100 |
| 5 | 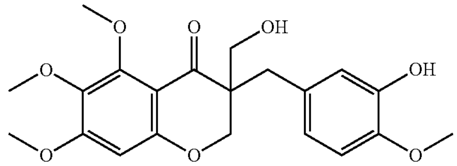 | >100 | >100 | >100 | >100 |
| 6a | 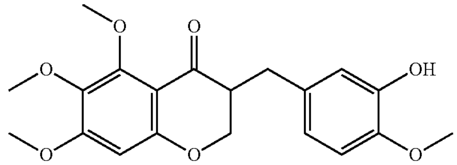 | >100 | >100 | >100 | >100 |
| 6b | 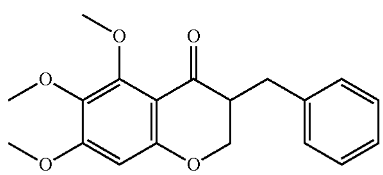 [SMILES: COc1cc2c(c(OC)c1OC)C(=O)C(Cc1ccccc1)CO2] | >100 | >100 | >100 | >100 |
| 6c (SH-11037) | 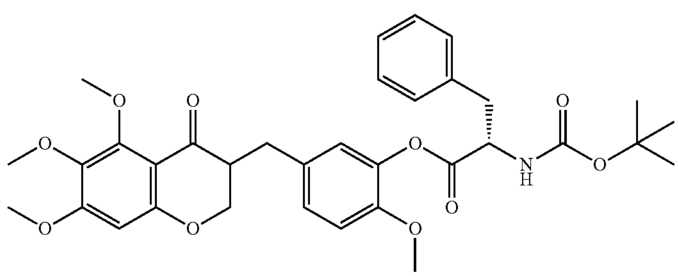 [SMILES: COc1ccc(CC2COc3cc(OC)c(OC)c(OC)c3C2=O)cc1OC(=O)[C@H](Cc1ccccc1)NC(=O)OC(C)(C)C] | 0.746 | 0.087 | 12 | 400 |
| 6d | 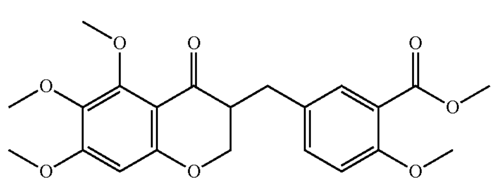 | 27 | 13 | 40 | >250 |
| 6e | 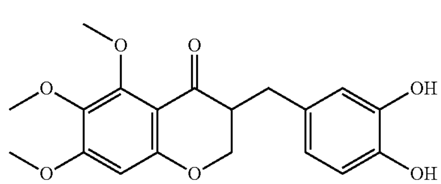 [SMILES: COc1cc2c(c(OC)c1OC)C(=O)C(Cc1ccc(O)c(O)c1)CO2] | 77 | >250 | 98 | >250 |

TABLE 1-continued

Anti-proliferative effects of synthetic cremastranone analogs on HRECs, HUVECs, Y-79 retinoblastoma cells and 92-1 uveal melanoma cells. 50% growth inhibitory (GI$_{50}$) concentrations are given in μM.

| Compound No. | Structure | GI50 HUVEC | GI50 HREC | GI50 Y-79 | GI50 92-1 |
|---|---|---|---|---|---|
| 6f | 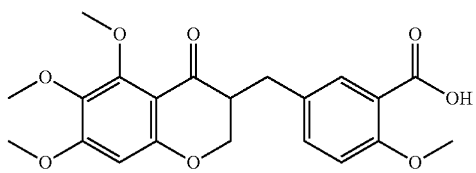 | 92 | 131 | >250 | >250 |
| 7 | 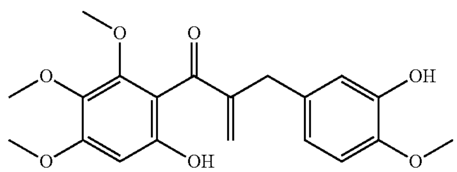 | 1.4 | 10 | 8 | 17 |
| 8a | 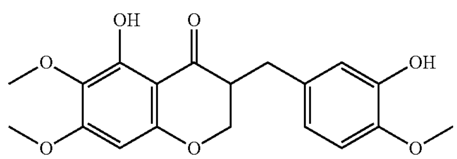 | 44 | >100 | >100 | >100 |
| 8b | 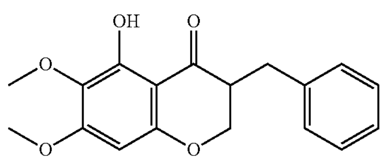 [SMILES: COc1cc2c(c(O)c1OC)C(=O)C(Cc1ccccc1)CO2] | 40 | >100 | >100 | >100 |
| 8c | 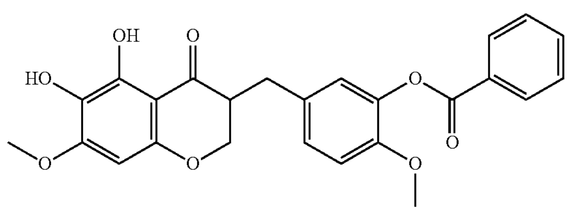 [SMILES: COc1ccc(CC2COc3cc(OC)c(O)c(O)c3C2=O)cc1OC(=O)c1ccccc1] | >100 | >100 | >50 | 51 |
| 8d | 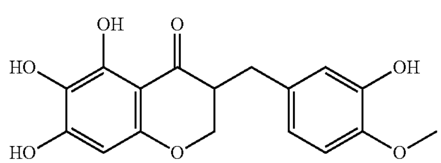 [SMILES: COc1ccc(CC2COc3cc(O)c(O)c(O)c3C2=O)cc1O] | 124 | 135 | >500 | >500 |
| 9a | 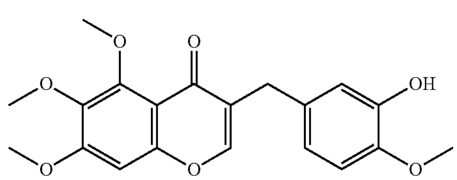 | >100 | >100 | >100 | >100 |
| 9b | 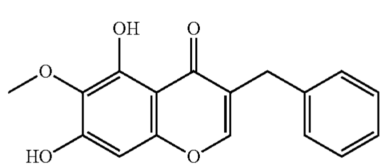 [SMILES: COc1c(O)cc2occ(Cc3ccccc3)c(=O)c2c1O] | >100 | >100 | >100 | >100 |

TABLE 1-continued

Anti-proliferative effects of synthetic cremastranone analogs on HRECs, HUVECs, Y-79 retinoblastoma cells and 92-1 uveal melanoma cells. 50% growth inhibitory ($GI_{50}$) concentrations are given in μM.

| Compound No. | Structure | GI50 HUVEC | GI50 HREC | GI50 Y-79 | GI50 92-1 |
|---|---|---|---|---|---|
| 10a | 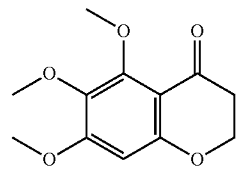 [SMILES: COc1cc2c(c(OC)c1OC)C(=O)CCO2] | >100 | >100 | >500 | >500 |
| 10b | 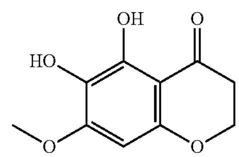 | >100 | >100 | >500 | 18 |
| 11a | 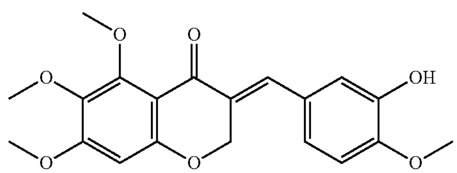 | 8 | 46 | 44 | 0.22 |
| 11b | 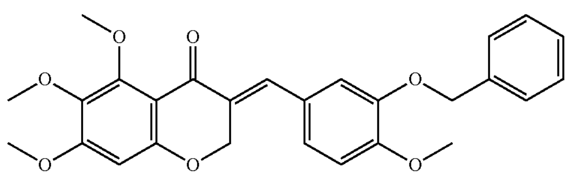 [SMILES: COc1ccc(/C=C2\COc3cc(OC)c(OC)c(OC)c3C2=O)cc1OCc1ccccc1] | 4 | 6 | 15 | — |
| 11c | 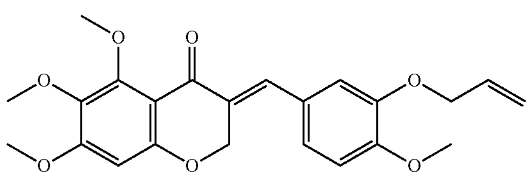 [SMILES: C=CCOc1cc(/C=C2\COc3cc(OC)c(OC)c(OC)c3C2=O)ccc1OC] | 11 | 4 | 3 | 3.2 |
| 11d | 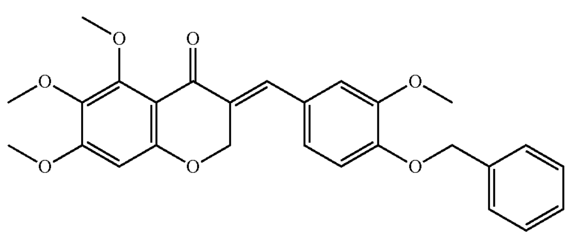 [SMILES: COc1cc(/C=C2\COc3cc(OC)c(OC)c(OC)c3C2=O)ccc1OCc1ccccc1] | 114 | 53 | 39 | 23 |
| 11e | 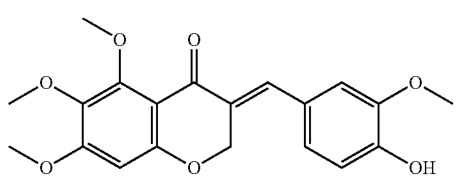 | 6 | 4 | 23 | 55 |
| 11f | 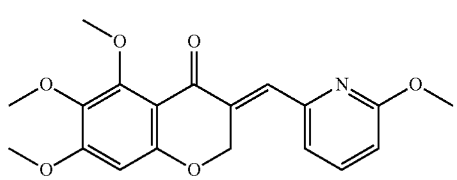 | 16 | 17 | 25 | 25 |

TABLE 1-continued

Anti-proliferative effects of synthetic cremastranone analogs on HRECs, HUVECs, Y-79 retinoblastoma cells and 92-1 uveal melanoma cells. 50% growth inhibitory ($GI_{50}$) concentrations are given in μM.

| Compound No. | Structure | GI50 HUVEC | GI50 HREC | GI50 Y-79 | GI50 92-1 |
|---|---|---|---|---|---|
| 11g | 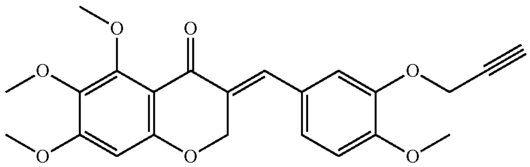 [SMILES: C#CCOc1cc(/C=C2\COc3cc(OC)c(OC)c(OC)c3C2=O)ccc1OC] | 21 | 39 | 32 | 310 |
| 11h | 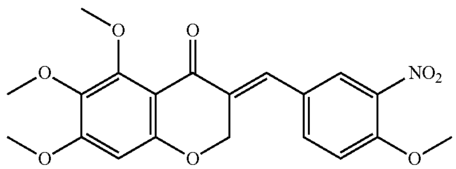 | 11 | 4 | 44 | 13 |
| 11i | 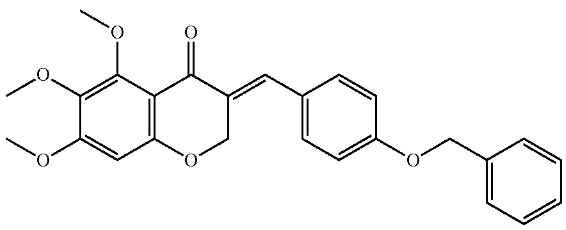 [SMILES: COc1cc2c(c(OC)c1OC)C(=O)/C(=C/c1ccc(OCc3ccccc3)cc1)CO2] | 284 | >500 | 465 | 152 |
| 11j | 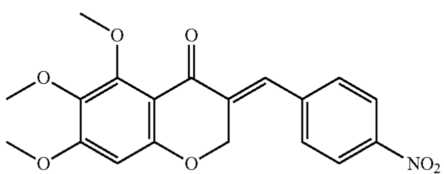 [SMILES: COc1cc2c(c(OC)c1OC)C(=O)/C(=C/c1ccc([N+](=O)[O-])cc1)CO2] | 6 | 14 | 9 | 23 |
| 11k | 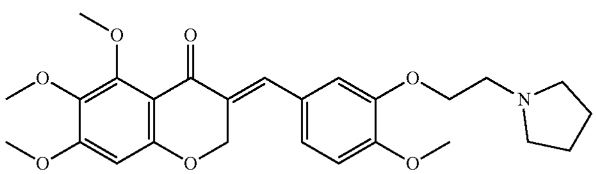 [SMILES: COc1ccc(/C=C2\COc3cc(OC)c(OC)c(OC)c3C2=O)cc1OCCN1CCCC1] | 3.5 | 0.185 | 3.2 | 6 |
| 11l | 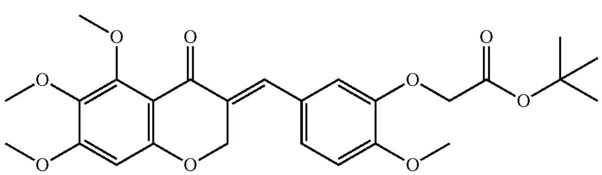 [SMILES: COc1ccc(/C=C2\COc3cc(OC)c(OC)c(OC)c3C2=O)cc1OCC(=O)OC(C)(C)C] | 27 | >500 | 21 | >500 |
| 11m | 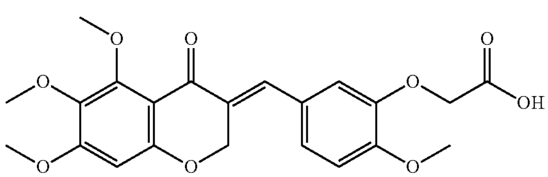 [SMILES: COc1ccc(/C=C2\COc3cc(OC)c(OC)c(OC)c3C2=O)cc1OCC(=O)O] | >500 | >500 | >500 | >500 |
| 11n | 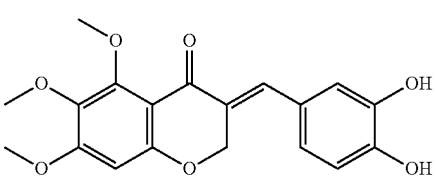 [SMILES: COc1cc2c(c(OC)c1OC)C(=O)/C(=C/c1ccc(O)c(O)c1)CO2] | 4.1 | 6.4 | 13 | 13.7 |

TABLE 1-continued

Anti-proliferative effects of synthetic cremastranone analogs on HRECs, HUVECs, Y-79 retinoblastoma cells and 92-1 uveal melanoma cells. 50% growth inhibitory (GI$_{50}$) concentrations are given in μM.

| Compound No. | Structure | GI50 HUVEC | GI50 HREC | GI50 Y-79 | GI50 92-1 |
|---|---|---|---|---|---|
| 11o | 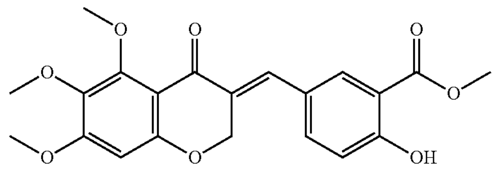 | 2 | 4.7 | 2.3 | 8.2 |
| 11p | 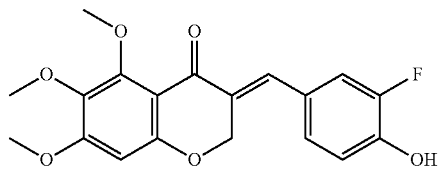 [SMILES: COc1cc2c(c(OC)c1OC)C(=O)/C(=C/c1ccc(O)c(F)c1)CO2] | 9 | 19 | 22 | 30 |
| 11q | 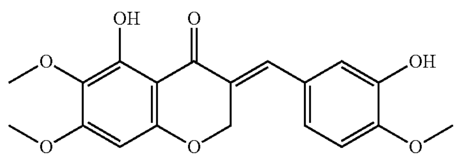 | 5.4 | 7 | 6 | 11 |
| 11r | 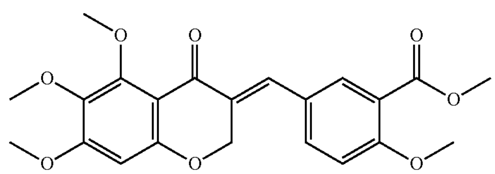 | 3.2 | 5.5 | 6 | >100 |
| 11s | 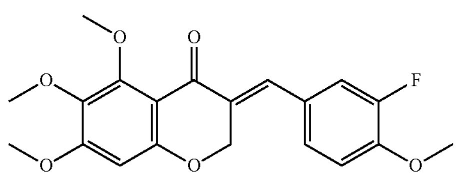 | 7.6 | 3.2 | 10 | 7 |
| 11t | 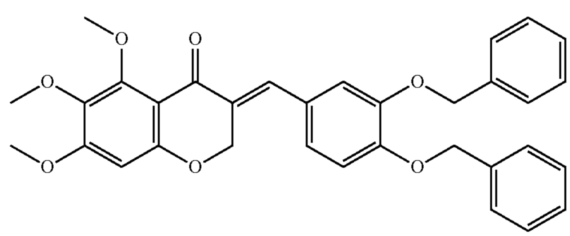 [SMILES: COc1cc2c(c(OC)c1OC)C(=O)/C(=C/c1ccc(OCc3ccccc3)c(OCc3ccccc3)c1)CO2] | 64 | 160 | 109 | >250 |
| 11u | 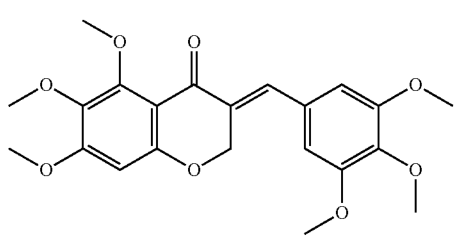 | 10.4 | 16.6 | 9 | >250 |
| 11v | 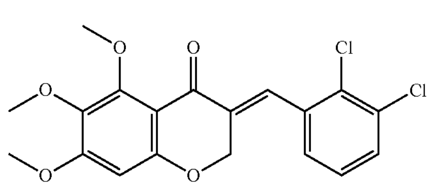 [SMILES: COc1cc2c(c(OC)c1OC)C(=O)/C(=C/c1cccc(Cl)c1Cl)CO2] | 10.4 | 25.6 | 18 | 31 |

TABLE 1-continued

Anti-proliferative effects of synthetic cremastranone analogs on HRECs, HUVECs, Y-79 retinoblastoma cells and 92-1 uveal melanoma cells. 50% growth inhibitory ($GI_{50}$) concentrations are given in μM.

| Compound No. | Structure | $GI_{50}$ HUVEC | $GI_{50}$ HREC | $GI_{50}$ Y-79 | $GI_{50}$ 92-1 |
|---|---|---|---|---|---|
| 11w | 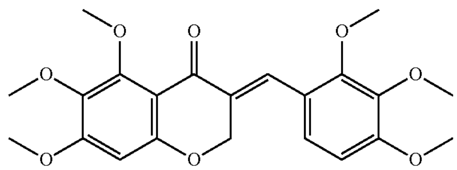 | 45 | 91 | 154 | >250 |
| 11x | 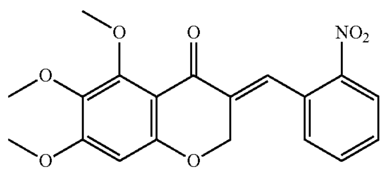 [SMILES: COc1cc2c(c(OC)c1OC)C(=O)/C(=C/c1ccccc1[N+](=O)[O-])CO2] | 9 | 8.6 | 8 | 29 |
| 12 | 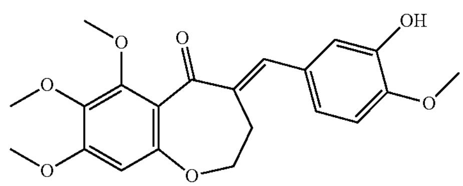 | 30 | 35 | 33 | 145 |
| 13 | 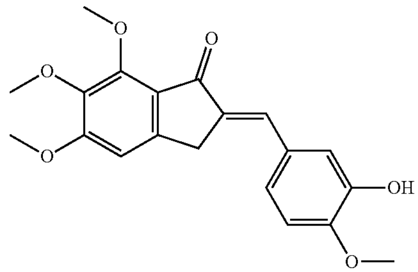 | 19 | 30 | 49 | 80 |
| 14 | 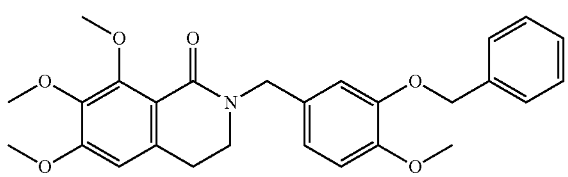 [SMILES: COc1ccc(CN2CCc3cc(OC)c(OC)c(OC)c3C2=O)cc1OCc1ccccc1] | 71 | 103 | >500 | 6 |
| 15a | 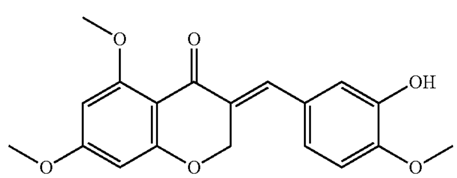 | 17.7 | 37 | 13.5 | 78.5 |
| 15b | 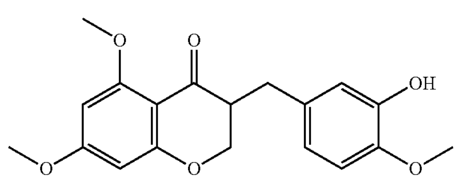 | 6.8 | 1.6 | 4.2 | >250 |

As shown in Table 1, while several compounds had no growth-inhibitory activity or cytotoxicity only at very high (500 μM) concentrations, a number had $GI_{50}$ values ranging from 0.087 to 100 μM. From these analyses, it was determined that the fused ring system is likely important in cremastranone isomer 2 and its analogs (3a vs. 11b), the benzyl group is essential (10a vs. 11a; 10b vs. 2), and small substitutions on the A ring are tolerated (2 vs. 1) (see FIG.

1 for atom and ring numbering). Important trends were noted such as the improvement of activity with unsaturation at C-3(9) (11a) as well as limited effects of C-ring size (12, 13), and the possibility of some tolerance for modifications on the B-ring (11b) including introduction of a heteroatom (11f). Notably, some synthetic modifications at C-3' (6c, 11k) increased potency while promoting >100-fold selectivity for HRECs over ocular tumor cell lines (Table 1).

Example 17

In this Example, the effects of SH-11037 (6c) on the growth of retinoblastoma tumors were evaluated. Since SH-11037 (6c) was not cytotoxic to retinoblastoma cells (Table 1), this Example offers evidence that the antiangiogenic mechanism of SH-11037 (6c) is capable of reducing retinoblastoma tumor growth.

Tag-RB retinoblastoma mice (a commonly used mouse model of this cancer) were intravitreally injected with SH-11037 (6c) or vehicle to a final vitreous concentration of 10 µM weekly starting at 7 or 8 weeks of age with sacrifice and enucleation at 10 or 11 weeks. Tumor progression was followed by optical coherence tomography in vivo and histopathological analysis post-mortem. Percent tumor burden in each eye was compared between cohorts and treatments by two-way ANOVA.

As shown in Table 1, SH-11037 (6c) did not block the growth of retinoblastoma or retinal pigment epithelial cells in culture, suggesting a lack of toxicity. However, as shown in FIGS. 19A-19E, in transgenic mice with retinoblastoma , SH-11037 (6c) significantly reduced tumor burden over vehicle (up to 26% reduction, p=0.022). No adverse effects were observed with weekly compound injections.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of treating retinoblastoma in a subject in need thereof, the method comprising administering an effective amount of the compound of formula (I)

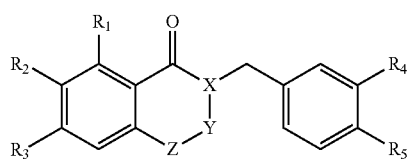

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen.

2. The method as set forth in claim 1, wherein $R_1$, $R_2$, $R_3$ are independently selected from the group consisting of hydroxyl and alkoxy.

3. The method as set forth in claim 1, wherein $R_1$, $R_2$, and $R_3$ are independently methoxy.

4. The method as set forth in claim 1, wherein $R_4$ and $R_5$ are independently selected from the group consisting of hydroxyl, alkoxy and substituted alkoxy.

5. The method as set forth in claim 4, wherein $R_4$ and $R_5$ are independently a substituted alkoxy having substitutions selected from linear alkyl, branched alkyl, and aryl.

6. The method as set forth in claim 1, wherein the compound is SH-11037 (6c).

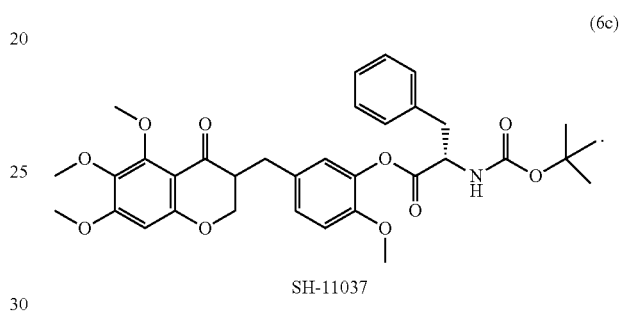

7. The method as set forth in claim 1 further comprising administering a pharmaceutically acceptable carrier with the compound.

8. The method as set forth in claim 6, wherein SH-11037 (6c) is administered via intravitreal injection.

9. The method as set forth in claim 8, wherein SH-11037 (6c) is administered in amounts ranging from about 0.1 µM to about 100 µM final intravitreal concentration.

10. A method of treating retinoblastoma in a subject in need thereof, the method comprising administering an effective amount of the compound of formula (VI)

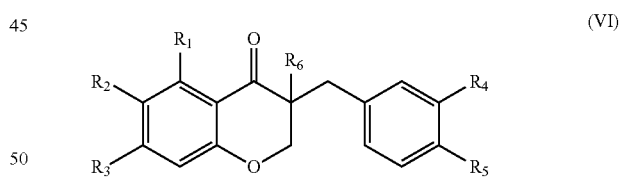

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl, and a pharmaceutically acceptable carrier.

11. The method as set forth in claim 10, wherein $R_6$ is selected from the group consisting of hydrogen and a hydroxylmethyl.

* * * * *